(12) United States Patent
Claremon et al.

(10) Patent No.: US 8,383,629 B2
(45) Date of Patent: Feb. 26, 2013

(54) INHIBITORS OF 11β-HYDROXYSTEROID DEHYDROGENASE TYPE 1

(75) Inventors: David A. Claremon, Maple Glen, PA (US); Colin M. Tice, Ambler, PA (US); Yuanjie Ye, Ambler, PA (US); Suresh B. Singh, Kendall Park, NJ (US); Wei He, Audubon, PA (US); Wei Zhao, Eagleville, PA (US); Robert D. Simpson, Wilmington, DE (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 12/919,370

(22) PCT Filed: Feb. 26, 2009

(86) PCT No.: PCT/US2009/001215
§ 371 (c)(1),
(2), (4) Date: Nov. 30, 2010

(87) PCT Pub. No.: WO2009/108332
PCT Pub. Date: Sep. 3, 2009

(65) Prior Publication Data
US 2011/0136821 A1 Jun. 9, 2011

Related U.S. Application Data

(60) Provisional application No. 61/031,975, filed on Feb. 27, 2008.

(51) Int. Cl.
*A61K 31/497* (2006.01)
*A61K 31/44* (2006.01)
*C07D 241/04* (2006.01)
*C07D 401/04* (2006.01)

(52) U.S. Cl. .......... 514/253.03; 514/278; 544/230; 546/17; 546/18

(58) Field of Classification Search .......... 514/253.03, 514/278; 544/230; 546/17, 18
See application file for complete search history.

(56) References Cited

U.S. PATENT DOCUMENTS

| | | | |
|---|---|---|---|
| 5,206,240 | A | 4/1993 | Baldwin et al. |
| 5,869,496 | A | 2/1999 | Hale et al. |
| 5,962,462 | A | 10/1999 | Mills et al. |
| 6,013,652 | A | 1/2000 | Maccoss et al. |
| 6,828,440 | B2 | 12/2004 | Goehring et al. |
| 6,943,199 | B2 | 9/2005 | De Lombaert et al. |
| 2004/0259890 | A1 | 12/2004 | Fukami et al. |
| 2006/0270653 | A1 | 11/2006 | Drutu et al. |
| 2007/0129345 | A1 | 6/2007 | Zhuo et al. |
| 2007/0210948 | A1 | 9/2007 | Wang et al. |
| 2007/0213311 | A1 | 9/2007 | Li et al. |
| 2008/0070902 | A1* | 3/2008 | Kimura et al. ........ 514/217.09 |
| 2011/0136821 | A1* | 6/2011 | Claremon et al. ........ 514/253.03 |

FOREIGN PATENT DOCUMENTS

| | | |
|---|---|---|
| EP | 0 444 945 | 2/1991 |
| WO | WO 98/25605 | 6/1998 |
| WO | WO 2006/002349 | 1/2006 |
| WO | WO 2006/122769 | 11/2006 |
| WO | WO 2007/028638 | 3/2007 |
| WO | WO 2007/084314 | 7/2007 |
| WO | WO 2007/101270 | 9/2007 |
| WO | WO 2009/108332 | 9/2009 |

OTHER PUBLICATIONS

International Search Report for PCT/US2009/001215, mailed Jun. 9, 2009.
Solly et al., "High-Throughput Screening of 11β-Hydroxysteroid Dehydrogenase Type 1 in Scintillation Proximity Assay Format," *ASSAY and Drug Development Technologies*, vol. 3(4), pp. 377-384 (2005).
Cheng et al., "Novel Radical Synthesis of Morphine Fragments Spiro[benzofuran-3(2H),4'-piperdine] and Octahydro-1H-benzofuro[3,2-3]isoquinoline," *Tetrahedron*, vol. 52(33) pp. 10935-10944 (1996).
International Preliminary Report on Patentability for PCT/US2009/001215, mailed Aug. 31, 2010.
Written Opinion of the International Searching Authority for PCT/US2009/001215, mailed Aug. 27, 2010.

* cited by examiner

*Primary Examiner* — James O Wilson
*Assistant Examiner* — Ebenezer O Sackey
(74) *Attorney, Agent, or Firm* — McCarter & English LLP; Steven G. Davis; Michael J. DeGrazia

(57) ABSTRACT

This invention relates to novel compounds of the Formulae I or II and pharmaceutically acceptable salts thereof, and pharmaceutical compositions thereof which are useful for the therapeutic treatment of diseases associated with the modulation or inhibition of 11 β-HSD 1 in mammals. Formula (I).

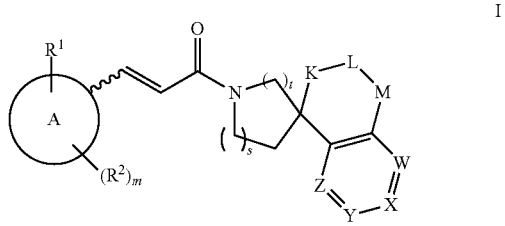

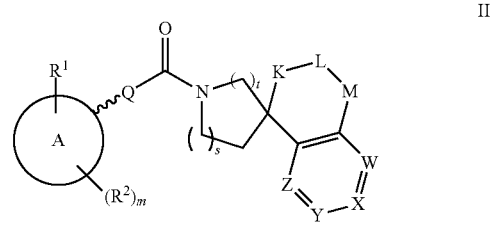

27 Claims, No Drawings

INHIBITORS OF 11β-HYDROXYSTEROID DEHYDROGENASE TYPE 1

RELATED APPLICATIONS

This application is the U.S. National Phase of PCT/US2009/001215, filed Feb. 26, 2009, which claims the benefit of U.S. Provisional Application No. 61/031,975, filed Feb. 27, 2008, the entire teachings of which are incorporated herein by reference.

FIELD OF THE INVENTION

The present invention relates to inhibitors of 11β-hydroxy steroid dehydrogenase type 1 (β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggests that inhibition of 11β-HSD1 may cause a drop in intraocular pressure in patients with intraocular hypertension (Kotelevtsev, et al., (1997), Proc. Nat'l Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low, et al., (1994) J. Mol. Endocrin. 13: 167-174). In contrast, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston, et al., (1994) Mol. Cell. Endocrin. 105: R11-R17), and has been shown to protect the MR from glucocorticoid excess (e.g., high levels of receptor-active cortisol) (Blum, et al., (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as "SAME") characterized by hypertension, hypokalemia, and sodium retention (Edwards, et al., (1988) Lancet 2: 986-989; Wilson, et al., (1998) Proc. Nat'l Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper, et al., (2003) Nat. Genet. 34: 434-439).

Notably, disruption of homeostasis in the HPA axis by either deficient or excess secretion or action results in Cushing's syndrome or Addison's disease, respectively (Miller & Chrousos, *Endocrinology and Metabolism* (Felig & Frohman eds., McGraw-Hill: New York, $4^{th}$ Ed. (2001)) 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven, (1993) Ann. Rev. Med. 44, 121-131). Although the role of glucocorticoids in human obesity is not fully characterized, there is mounting evidence that 11β-HSD1 activity plays an important role in obesity and metabolic syndrome (Bujalska, et al., (1997) Lancet 349: 1210-1213); (Livingstone, et al., (2000) Endocrinology 131, 560-563; Rask, et al., (2001) J. Clin. Endocrinol. Metab. 86, 1418-1421; Lindsay, et al., (2003) J. Clin. Endocrinol. Metab. 88: 2738-2744; Wake, et al., (2003) J. Clin. Endocrinol. Metab. 88, 3983-3988).

Data from studies in mouse transgenic models supports the hypothesis that adipocyte 11β-HSD1 activity plays a central role in visceral obesity and metabolic syndrome (Alberts, et al., (2002) Diabetologia. 45(11), 1526-32). Over-expression in adipose tissue of 11β-HSD1 under the control of the aP2 promoter in transgenic mice produced a phenotype remarkably similar to human metabolic syndrome (Masuzaki, et al., (2001) Science 294, 2166-2170; Masuzaki, et al., (2003) J. Clinical Invest. 112, 83-90). Moreover, the increased activity of 11β-HSD1 in these mice is very similar to that observed in human obesity (Rask, et al., (2001) J. Clin. Endocrinol. Metab. 86, 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev, et al., (1997) Proc. Nat'l Acad. Sci. 94: 14924-

14929; Morton, et al., (2001) J. Biol. Chem. 276, 41293-41300; Morton, et al., (2004) Diabetes 53, 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or other aspects of the metabolic syndrome cluster, including glucose intolerance, insulin resistance, hyperglycemia, hypertension, and/or hyperlipidemia (Kotelevstev, et al., (1997) Proc. Nat'l Acad. Sci. 94, 14924-14929; Morton, et al., (2001) J. Biol. Chem. 276, 41293-41300; Morton, et al., (2004) Diabetes 53, 931-938). In addition, inhibition of 11β-HSD1 activity may have beneficial effects on the pancreas, including the enhancement of glucose-stimulated insulin release (Billaudel & Sutter, (1979) Horm. Metab. Res. 11, 555-560; Ogawa, et al., (1992) J. Clin. Invest. 90, 497-504; Davani, et al., (2000) J. Biol. Chem. 275, 34841-34844). Inter-individual differences in general cognitive function has been linked to variability in the long-term exposure to glucocorticoids (Lupien, et al., (1998) Nat. Neurosci. 1: 69-73) and dysregulation of the HPA axis. Such chronic exposure to glucocorticoid excess in certain brain subregions has been theorized to contribute to the decline of cognitive function (McEwen & Sapolsky (1995) Curr. Opin. Neurobiol. 5, 205-216). Therefore, inhibition of 11β-HSD1 may reduce exposure to glucocorticoids in the brain and thereby protect against deleterious glucocorticoid effects on neuronal function, including cognitive impairment, dementia, and/or depression.

There is also evidence that glucocorticoids and 11β-HSD1 play a role in regulation of in intra-ocular pressure (IOP) (Stokes, et al., (2000) Invest. Ophthalmol. Vis. Sci. 41: 1629-1683; Rauz, et al., (2001) Invest. Ophthalmol. Vis. Sci. 42: 2037-2042). If left untreated, elevated IOP can lead to partial visual field loss and eventually blindness. Thus, inhibition of 11β-HSD1 in the eye could reduce local glucocorticoid concentrations and IOP, and hence could be used to treat or prevent glaucoma and other visual disorders.

Transgenic aP2-11β-HSD1 mice exhibit high arterial blood pressure and have increased sensitivity to dietary salt. Additionally, plasma angiotensinogen levels are elevated in the transgenic mice, as are angiotensin II and aldosterone. Treatment of the mice with an angiotensin II antagonist alleviates the hypertension (Masuzaki, et al., (2003) J. Clinical Invest. 112, 83-90). This suggests that hypertension may be caused or exacerbated by 11β-HSD1 activity. Thus, 11β-HSD1 inhibitors may be useful for treatment of hypertension and hypertension-related cardiovascular disorders.

Glucocorticoids can have adverse effects on skeletal tissues, and prolonged exposure to even moderate glucocorticoid doses can result in osteoporosis (Cannalis, (1996) J. Clin. Endocrinol. Metab. 81, 3441-3447). In addition, 11β-HSD1 has been shown to be present in cultures of human primary osteoblasts as well as cells from adult bone (Cooper, et al., (2000) Bone 27: 375-381), and the 11β-HSD1 inhibitor carbenoxolone has been shown to attenuate the negative effects of glucocorticoids on bone nodule formation (Bellows, et al., (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

As evidenced herein, there is a continuing need for new and improved drugs that inhibit 11β-HSD1. The novel compounds of the present invention are effective inhibitors of 11β-HSD1.

SUMMARY OF THE INVENTION

The present invention provides compounds of Formula I:

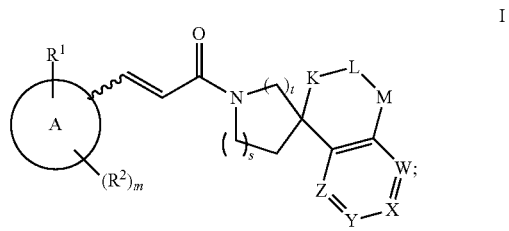

or a pharmaceutically acceptable salt thereof, wherein:

A is a monocyclic heteroaromatic group or a phenyl group;
$R^1$ is independently halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, halo$(C_1-C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, $NR^{11}SO_2R^{13}$, or HetCy; or a $(C_1-C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

each $R^2$ is independently hydrogen, halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, halo$(C_1-C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1-C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

m is an integer from 0-3;
p is 0, 1 or 2;
s is 1 or 2;
t is 1 or 2;
K, L and M are independently selected from O, $NR^4$, $CR^{4a}R^{4b}$ or CO; provided: i) that no more than one of K, L and M is CO; ii) that K-L and L-M are not —O—O—; and iii) that K-L-M- is not —O—$NR^4$—O— or —$NR^4$—$NR^4$—$NR^4$—;

each $R^4$ is independently hydrogen, $(C_1-C_6)$alkyl, $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, $SO_2NR^{14}R^{15}$, Ar or HetAr; or $(C_1-C_6)$alkyl substituted with OH, $NR^{14}R^{15}$, $C(O)R^{14}$, $C(S)R^{14}$, $COOR^{14}$, $C(S)OR^{14}$, $C(O)NR^{14}R^{15}$, $C(S)NR^{14}R^{15}$, $NR^{14}C(O)NR^{14}R^{15}$, $NR^{14}C(S)NR^{14}R^{15}$, $OC(O)NR^{14}R^{15}$, $OC(S)$ $NR^{14}R^{15}$, $NR^{14}C(O)OR^{14}$, $NR^{14}C(S)OR^{14}$, $SO_2R^{14}$, $NR^{14}SO_2R^{14}$, $SO_2NR^{14}R^{15}$, $NR^{14}SO_2NR^{14}R^{15}$, Ar or HetAr;

each $R^{4a}$ and each $R^{4b}$ is independently selected from hydrogen, $OR^{14}$, $NR^{14}R^{15}$, $C(O)R^{14}$, $C(S)R^{14}$, $COOR^{14}$, $C(S)OR^{14}$, $C(O)NHSO_2R^{14}$, $C(S)NHSO_2R^{14}$, $C(O)NR^{14}R^{15}$, $C(S)NR^{14}R^{15}$, $NR^{11}C(O)R^{14}$, $NR^{11}C(S)R^{14}$, $NR^{11}C(O)NR^{14}R^{15}$, $NR^{11}C(S)NR^{14}R^{15}$, $NR^{11}C(O)NHSO_2R^{14}$, $NR^{11}C(S)NHSO_2R^{14}$, $OC(O)R^{14}$, $OC(S)R^{14}$, $OC(O)NR^{14}R^{15}$, $OC(S)NR^{14}R^{15}$, $OC(O)NHSO_2R^{14}$, $OC(S)NHSO_2R^{14}$, $NR^{11}C(O)OR^{14}$, $NR^{11}C(S)OR^{14}$, $SO_2R^{14}$, $NR^{11}SO_2R^{14}$, $SO_2NR^{14}R^{15}$, $NR^{11}SO_2NR^{14}R^{15}$, Ar, HetAr, or HetCy; or $(C_1-C_6)$alkyl optionally substituted with OH, $NR^{14}R^{15}$, $C(O)R^{14}$, $C(S)R^{14}$, $C(O)NHSO_2R^{14}$, $C(S)NHSO_2R^{14}$, $COOR^{14}$, $C(S)OR^{14}$, $C(O)NR^{14}R^{15}$, $C(S)NR^{14}R^{15}$, $NR^{11}C(O)NR^{14}R^{15}$, $NR^{11}C(S)NR^{14}R^{15}$, $OC(O)NR^{14}R^{15}$, $OC(S)NR^{14}R^{15}$, $NR^{11}C(O)OR^{14}$, $NR^{11}C(S)OR^{14}$, $SO_2R^{14}$, $NR^{11}SO_2R^{14}$, $SO_2NR^{14}R^{15}$, Ar, HetAr, or HetCy;

W, X, Y and Z are independently selected from N, $CR^5$, provided that no more than two of W, X, Y and Z are N;

each $R^5$ is independently selected from hydrogen, halo, $OR^{11}$, $S(O)_pR^{11}$, CN, $NO_2$, $COR^{11}$, $CSR^{11}$, $CO_2R^{11}$, CHO, $(C_1-C_6)$alkyl, halo$(C_1-C_6)$alkyl, halo$(C_1-C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1-C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

each $R^{11}$ and each $R^{12}$ is independently selected from hydrogen, $(C_1-C_6)$alkyl or $(C_1-C_6)$hydroxyalkyl;

$R^{13}$ is $(C_1-C_6)$alkyl or $(C_1-C_6)$hydroxyalkyl;

each $R^{14}$ and each $R^{15}$ is independently hydrogen or $(C_1-C_6)$alkyl, optionally substituted with $OR^{11}$, $NR^{11}R^{12}$, $C(O)R^{11}$, $C(S)R^{11}$, $COOR^{11}$, $C(S)OR^{11}$, $C(O)NR^{11}R^{12}$, $C(S)NR^{11}R^{12}$, $NR^{11}C(O)R^{11}$, $NR^{11}C(S)R^{11}$, $NR^{11}C(O)NR^{11}R^{12}$, $NR^{11}C(S)NR^{11}R^{12}$, $NR^{11}C(O)NHSO_2R^{11}$, $NR^{11}C(S)NHSO_2R^{11}$, $OC(O)R^{11}$, $OC(S)R^{11}$, $OC(O)NR^{11}R^{12}$, $OC(S)NR^{11}R^{12}$, $OC(O)NHSO_2R^{11}$, $OC(S)NHSO_2R^{11}$, $NR^{11}C(O)OR^{11}$, $NR^{11}C(S)OR^{11}$, $SO_2R^{11}$, $NR^{11}SO_2R^{11}$, $SO_2NR^{11}R^{12}$, $NR^{11}SO_2NR^{11}R^{12}$, Ar, HetAr, or HetCy;

or $NR^{14}R^{15}$ taken together forms a 4, 5, 6- or 7-membered heterocyclic group containing 1 or 2 nitrogen atoms, 0 or 1 oxygen atoms and 0 or 1 sulfur atoms, said ring being optionally substituted at any one or more substitutable ring carbon with oxo, hydroxy, or $(C_1-C_3)$alkyl, and optionally substituted at any one or more substitutable ring nitrogen with $(C_1-C_3)$alkyl, $C(O)R^{11}$, $C(O)OR^{11}$ or $C(O)NR^{11}R^{12}$;

each Ar is aryl optionally substituted with halogen, $(C_1-C_6)$alkyl, hydroxy, $(C_1-C_6)$alkoxy, $(C_1-C_6)$alkylamino, di$(C_1-C_6)$alkylamino, $NO_2$, CN, $CONH_2$, $(C_1-C_6)$haloakyl or $(C_1-C_6)$haloalkoxy;

each HetAr is heteroaryl optionally substituted with halogen, $(C_1-C_6)$alkyl, hydroxy, $(C_1-C_6)$alkoxy, $(C_1-C_6)$alkylamino, di$(C_1-C_6)$alkylamino, $NO_2$, CN, $CONH_2$, $(C_1-C_6)$haloakyl or $(C_1-C_6)$haloalkoxy; and each HetCy is a monocyclic heterocyclic group containing at least one ring atom selected from nitrogen, oxygen or sulfur, said ring being optionally substituted at any one or more substitutable ring carbon with oxo, hydroxy, or $(C_1-C_3)$ alkyl, and optionally substituted at any one or more substitutable ring nitrogen with $(C_1-C_3)$alkyl, $C(O)R^{11}$, $C(O)OR^{11}$ or $C(O)NR^{11}R^{12}$.

The present invention also provides a pharmaceutical composition comprising a disclosed 11β-HSD1 inhibitor, including a compound of Formula I, and a pharmaceutically acceptable carrier or diluent, wherein the values for the variables are as described above for the compounds of Formula I.

The present invention further provides a method of inhibiting 11β-HSD1, comprising administering to a mammal in need thereof an effective amount of a disclosed 11β-HSD1 inhibitor, including a compound of Formula I, wherein the values for the variables are as described above for the compounds of Formula I.

The present invention further provides a method of inhibiting 11β-HSD1, comprising administering to a mammal in need thereof an effective amount of a compound of Formula II:

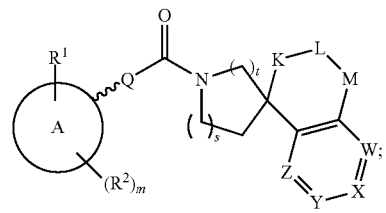

II or a pharmaceutically acceptable salt thereof, wherein:

A is a monocyclic heteroaromatic group or a phenyl group;

$R^1$ and each $R^2$ is each independently hydrogen, halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, halo$(C_1-C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, $NR^{11}SO_2R^{13}$, or HetCy; or a $(C_1-C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

Q is $CH_2$, $CH_2CH_2$, CH=CH, $CH_2O$ (wherein O is connected to the carbonyl carbon), $OCH_2$, $CH_2NR^3$ (wherein $NR^3$ is connected to the carbonyl carbon), or $NR^3CH_2$, provided that Q is CH=CH when K is CO and L is $NR^4$;

$R^3$ is hydrogen, $(C_1-C_6)$alkyl, halo$(C_1-C_6)$alkyl or hydroxy$(C_1-C_6)$alkyl;

m is an integer from 0-3;

p is 0, 1 or 2;

s is 1 or 2;

t is 1 or 2;

K, L and M are independently selected from O, $NR^4$, $CR^{4a}R^{4b}$ or CO; provided: i) that no more than one of K, L and M is CO; ii) that K-L and L-M are not —O—O—; and iii) that K-L-M- is not —O—$NR^4$—O— or —$NR^4$—$NR^4$—$NR^4$—;

each $R^4$ is independently hydrogen, $(C_1-C_6)$alkyl, $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, $SO_2NR^{14}R^{15}$, Ar or HetAr; or $(C_1-C_6)$ alkyl substituted with OH, $NR^{14}R^{15}$, $C(O)R^{14}$, $C(S)R^{14}$, $COOR^{14}$, $C(S)OR^{14}$, $C(O)NR^{14}R^{15}$, $C(S)NR^{14}R^{15}$, $NR^{14}C(O)NR^{14}R^{15}$, $NR^{14}C(S)NR^{14}R^{15}$, $OC(O)NR^{14}R^{15}$, $OC(S)$ $NR^{14}R^{15}$, $NR^{14}C(O)OR^{14}$, $NR^{14}C(S)OR^{14}$, $SO_2R^{14}$, $NR^{14}SO_2R^{14}$, $SO_2NR^{14}R^{15}$, $NR^{14}SO_2NR^{14}R^{15}$, Ar or HetAr;

each $R^{4a}$ and each $R^{4b}$ is independently selected from hydrogen, $OR^{14}$, $NR^{14}R^{15}$, $C(O)R^{14}$, $C(S)R^{14}$, $COOR^{14}$, $C(S)OR^{14}$, $C(O)NHSO_2R^{14}$, $C(S)NHSO_2R^{14}$, $C(O)NR^{14}R^{15}$, $C(S)NR^{14}R^{15}$, $NR^{11}C(O)R^{14}$, $NR^{11}C(S)R^{14}$, $NR^{11}C(O)NR^{14}R^{15}$, $NR^{11}C(S)NR^{14}R^{15}$, $NR^{11}C(O)NHSO_2R^{14}$, $NR^{11}C(S)NHSO_2R^{14}$, $OC(O)R^{14}$, $OC(S)R^{14}$, $OC(O)NR^{14}R^{15}$, $OC(S)NR^{14}R^{15}$, $OC(O)NHSO_2R^{14}$, $OC(S)NHSO_2R^{14}$, $NR^{11}C(O)OR^{14}$, $NR^{11}C(S)OR^{14}$, $SO_2R^{14}$, $NR^{11}SO_2R^{14}$, $SO_2NR^{14}R^{15}$, $NR^{11}SO_2NR^{14}R^{15}$, Ar, HetAr, or HetCy; or $(C_1-C_6)$alkyl optionally substituted with OH, $NR^{14}R^{15}$, $C(O)R^{14}$, $C(S)R^{14}$, $C(O)NHSO_2R^{14}$, $C(S)NHSO_2R^{14}$, $COOR^{14}$, $C(S)OR^{14}$, $C(O)NR^{14}R^{15}$, $C(S)NR^{14}R^{15}$, $NR^{11}C(O)NR^{14}R^{15}$, $NR^{11}C(S)NR^{14}R^{15}$, $OC(O)NR^{14}R^{15}$, $OC(S)NR^{14}R^{15}$, $NR^{11}C(O)OR^{14}$, $NR^{11}C(S)OR^{14}$, $SO_2R^{14}$, $NR^{11}SO_2R^{14}$, $SO_2NR^{14}R^{15}$, Ar, HetAr, or HetCy;

W, X, Y and Z are independently selected from N, $CR^5$, provided that no more than two of W, X, Y and Z are N;

each $R^5$ is independently selected from hydrogen, halo, $OR^{11}$, $S(O)_pR^{11}$, CN, $NO_2$, $COR^{11}$, $CSR^{11}$, $CO_2R^{11}$, CHO, $(C_1-C_6)$alkyl, halo$(C_1-C_6)$alkyl, halo$(C_1-C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1-C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

each $R^{11}$ and $R^{12}$ is independently selected from hydrogen, $(C_1-C_6)$alkyl or $(C_1-C_6)$hydroxyalkyl;

$R^{13}$ is $(C_1-C_6)$alkyl or $(C_1-C_6)$hydroxyalkyl;

each $R^{14}$ and each $R^{15}$ is independently hydrogen or $(C_1-C_6)$alkyl, optionally substituted with $OR^{11}$, $NR^{11}R^{12}$, $C(O)R^{11}$, $C(S)R^{11}$, $COOR^{11}$, $C(S)OR^{11}$, $C(O)NR^{11}R^{12}$, $C(S)NR^{11}R^{12}$, $NR^{11}C(O)R^{11}$, $NR^{11}C(S)R^{11}$, $NR^{11}C(O)NR^{11}R^{12}$, $NR^{11}C(S)NR^{11}R^{12}$, $NR^{11}C(O)NHSO_2R^{11}$, $NR^{11}C(S)NHSO_2R^{11}$, $OC(O)R^{11}$, $OC(S)R^{11}$, $OC(O)NR^{11}R^{12}$, $OC(S)NR^{11}R^{12}$, $OC(O)NHSO_2R^{11}$, $OC(S)NHSO_2R^{11}$, $NR^{11}C(O)OR^{11}$, $NR^{11}C(S)OR^{11}$, $SO_2R^{11}$, $NR^{11}SO_2R^{11}$, $SO_2NR^{11}R^{12}$, $NR^{11}SO_2NR^{11}R^{12}$, Ar, HetAr, or HetCy;

or $NR^{14}R^{15}$ taken together forms a 4, 5, 6- or 7-membered heterocyclic group containing 1 or 2 nitrogen atoms, 0 or 1 oxygen atoms and 0 or 1 sulfur atoms, said ring being optionally substituted at any one or more substitutable ring carbon with oxo, hydroxy, or $(C_1-C_3)$alkyl, and optionally substituted at any one or more substitutable ring nitrogen with $(C_1-C_3)$alkyl, $C(O)R^{11}$, $C(O)OR^{11}$ or $C(O)NR^{11}R^{12}$;

each Ar is aryl optionally substituted with $(C_1-C_6)$alkyl, hydroxy, $(C_1-C_6)$alkoxy, $(C_1-C_6)$alkylamino, di$(C_1-C_6)$alkylamino, $NO_2$, CN, $(C_1-C_6)$haloalkyl or $(C_1-C_6)$haloalkoxy;

each HetAr is heteroaryl optionally substituted with $(C_1-C_6)$alkyl, hydroxy, $(C_1-C_6)$alkoxy, $(C_1-C_6)$alkylamino, di$(C_1-C_6)$alkylamino, $NO_2$, CN, $(C_1-C_6)$haloalkyl or $(C_1-C_6)$haloalkoxy; and each HetCy is a monocyclic heterocyclic group containing at least one ring atom selected from nitrogen, oxygen or sulfur, said ring being optionally substituted at any one or more substitutable ring carbon with oxo, hydroxy, or $(C_1-C_3)$alkyl, and optionally substituted at any one or more substitutable ring nitrogen with $(C_1-C_3)$alkyl, $C(O)R^{11}$, $C(O)OR^{11}$ or $C(O)NR^{11}R^{12}$.

Also included in the present invention is a method of treating a disease or disorder associated with activity or expression of 11β-HSD1, comprising administering to a mammal in need thereof an effective amount of a disclosed 11β-HSD1 inhibitor, including a compound of Formula I or II, or a pharmaceutically acceptable salt thereof.

Also included in the present invention is the use of a disclosed 11β-HSD1 inhibitor, including a compound of Formula I or II, or a pharmaceutically acceptable salt thereof, for the manufacture of a medicament for inhibiting 11β-HSD1 activity in a mammal in need of such treatment.

Also included in the present invention is the use of a disclosed 11β-HSD1 inhibitor, including a compound of Formula I or II, or a pharmaceutically acceptable salt thereof, for the manufacture of a medicament for treating a disease or disorder related to the activity or expression of 11β-HSD1, inhibiting the conversion of cortisone to cortisol in a cell, inhibiting production of cortisol in a cell, increasing insulin sensitivity in a mammal in need thereof, modulating 11β-HSD1 activity in a mammal in need thereof, and/or inhibiting 11β-HSD1 in a mammal in need thereof.

Also included in the present invention is a disclosed 11β-HSD1 inhibitor, including a compound of Formula I or II, or a pharmaceutically acceptable salt thereof, for use in inhibiting 11β-HSD1 activity in a mammal in need of such treatment.

Also included in the present invention is a disclosed 11β-HSD1 inhibitor, including a compound of Formula I or II, or a pharmaceutically acceptable salt thereof, for use in therapy, e.g., treating a disease or disorder associated with activity or expression of 11β-HSD1 in a subject.

Also included in the present invention is a pharmaceutical composition comprising a disclosed 11β-HSD1 inhibitor, including a compound of Formula I or II, or a pharmaceutically acceptable salt thereof, and a pharmaceutically acceptable carrier or diluent.

DETAILED DESCRIPTION OF THE INVENTION

In one embodiment, the 11β-HSD1 inhibitors of the invention are represented by Structural Formula I or II. Pharmaceutically acceptable salts of the 11β-HSD1 inhibitors disclosed herein (including those represented by Structural Formulae I or II) are also included in the invention. Values and alternative values for the variables in Structural Formulae I and II are provided in the following paragraphs:

A is a monocyclic heteroaromatic group or a phenyl group. Alternatively, A is a phenyl group.

Q is $CH_2$, $CH_2CH_2$, CH=CH, $CH_2O$ (wherein O is connected to the carbonyl carbon), $OCH_2$, $CH_2NR^3$ (wherein $NR^3$ is connected to the carbonyl carbon), or $NR^3CH_2$, provided that Q is CH=CH when K is CO and L is $NR^4$. Alternatively, Q is CH=CH.

$R^1$ is independently halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, halo$(C_1-C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, $NR^{11}SO_2R^{13}$ or HetCy; or a $(C_1-C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1-C_6)$alkyl, halo$(C_1-C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$.

Alternatively, $R^1$ is halo, $(C_1\text{-}C_3)$alkyl, $(C_1\text{-}C_3)$haloalkyl, $(C_1\text{-}C_3)$alkoxy, or $(C_1\text{-}C_3)$haloalkoxy.

Each $R^2$ is independently hydrogen, halo, $OR^{11}$, $S(O)_pR^{11}$, CN, $NO_2$, $C(O)R^{11}$, $C(S)R^{11}$, $CO_2R^{11}$, CHO, $(C_1\text{-}C_6)$alkyl, halo$(C_1\text{-}C_6)$alkyl, halo$(C_1\text{-}C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1\text{-}C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1\text{-}C_6)$alkyl, halo$(C_1\text{-}C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$.

Alternatively, each $R^2$ is independently hydrogen, halo, $(C_1\text{-}C_3)$alkyl, hydroxy, $COO(C_1\text{-}C_3)$alkyl, $(C_1\text{-}C_3)$alkoxy, $(C_1\text{-}C_3)$alkylamino, di$(C_1\text{-}C_3)$alkylamino, $NO_2$, CN, $(C_1\text{-}C_3)$haloalkyl or $(C_1\text{-}C_3)$haloalkoxy.

$R^3$ is hydrogen, $(C_1\text{-}C_6)$alkyl, halo$(C_1\text{-}C_6)$alkyl or hydroxy$(C_1\text{-}C_6)$alkyl.

Alternatively, $R^3$ is hydrogen or methyl.

m is an integer from 0-3. Alternatively, m=0. Alternatively, m=1.

p is 0, 1 or 2.

s is 1 or 2. Alternatively, s is 1. t is 1 or 2. Alternatively, t is 2. Alternatively, s is 1 and t is 2.

K, L and M are independently selected from O, $NR^4$, $CR^{4a}R^{4b}$ or CO; provided: i) that no more than one of K, L and M is CO; ii) that K-L and L-M are not —O—O—; and iii) that K-L-M- is not —O—$NR^4$—O— or —$NR^4$—$NR^4$—$NR^4$—.

Each $R^4$ is independently hydrogen, $(C_1\text{-}C_6)$alkyl, $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, $SO_2NR^{14}R^{15}$, Ar or HetAr; or $(C_1\text{-}C_6)$alkyl substituted with OH, $NR^{14}R^{15}$, $C(O)R^{14}$, $C(S)R^{14}$, $COOR^{14}$, $C(S)OR^{14}$, $C(O)NR^{14}R^{15}$, $C(S)NR^{14}R^{15}$, $NR^{14}C(O)NR^{14}R^{15}$, $NR^{14}C(S)NR^{14}R^{15}$, $OC(O)NR^{14}R^{15}$, $OC(S)NR^{14}R^{15}$, $NR^{14}C(O)OR^{14}$, $NR^{14}C(S)OR^{14}$, $SO_2R^{14}$, $NR^{14}SO_2R^{14}$, $SO_2NR^{14}R^{15}$, $NR^{14}SO_2NR^{14}R^{15}$, Ar or HetAr.

Alternatively, each $R^4$ is independently hydrogen, $(C_1\text{-}C_6)$alkyl, $C(O)R^{14}$, $COOR^{14}$, or $SO_2R^{14}$.

Alternatively, each $R^4$ is independently $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, or $SO_2NR^{14}R^{15}$.

Each $R^{4a}$ and each $R^{4b}$ is independently selected from hydrogen, $OR^{14}$, $NR^{14}R^{15}$, $C(O)R^{14}$, $C(S)R^{14}$, $COOR^{14}$, $C(S)OR^{14}$, $C(O)NHSO_2R^{14}$, $C(S)NHSO_2R^{14}$, $C(O)NR^{14}R^{15}$, $C(S)NR^{14}R^{15}$, $NR^{11}C(O)R^{14}$, $NR^{11}C(S)R^{14}$, $NR^{11}C(O)NR^{14}R^{15}$, $NR^{11}C(S)NR^{14}R^{15}$, $NR^{11}C(O)NHSO_2R^{14}$, $NR^{11}C(S)NHSO_2R^{14}$, $OC(O)R^{14}$, $OC(S)R^{14}$, $OC(O)NR^{14}R^{15}$, $OC(S)NR^{14}R^{15}$, $OC(O)NHSO_2R^{14}$, $OC(S)NHSO_2R^{14}$, $NR^{11}C(O)OR^{14}$, $NR^{11}C(S)OR^{14}$, $SO_2R^{14}$, $NR^{11}SO_2R^{14}$, $SO_2NR^{14}R^{15}$, $NR^{11}SO_2NR^{14}R^{15}$, Ar, HetAr, or HetCy; or $(C_1\text{-}C_6)$alkyl optionally substituted with OH, $NR^{14}R^{15}$, $C(O)R^{14}$, $C(S)R^{14}$, $C(O)NHSO_2R^{14}$, $C(S)NHSO_2R^{14}$, $COOR^{14}$, $C(S)OR^{14}$, $C(O)NR^{14}R^{15}$, $C(S)NR^{14}R^{15}$, $NR^{11}C(O)NR^{14}R^{15}$, $NR^{11}C(S)NR^{14}R^{15}$, $OC(O)NR^{14}R^{15}$, $OC(S)NR^{14}R^{15}$, $NR^{11}C(O)OR^{14}$, $NR^{11}C(S)OR^{14}$, $SO_2R^{14}$, $NR^{11}SO_2R^{14}$, $SO_2NR^{14}R^{15}$, Ar, HetAr, or HetCy.

Alternatively, each $R^{4a}$ and each $R^{4b}$ is independently selected from hydrogen, $OR^{14}$, $NR^{14}R^{15}$, $C(O)NR^{14}R^{15}$, $NR^{11}C(O)R^{14}$, $NR^{11}C(O)NHSO_2R^{14}$, $NR^{11}C(O)NR^{14}R^{15}$, $OC(O)R^{14}$, $OC(O)NR^{14}R^{15}$, $OC(O)NHSO_2R^{14}$, HetCy, $(C_1\text{-}C_3)$alkyl, or $(C_1\text{-}C_3)$alkyl substituted with $NR^{14}R^{15}$, $COOR^{14}$, $C(O)NHSO_2R^{14}$, or $C(O)NR^{14}R^{15}$ (e.g., each $R^{4a}$ and each $R^{4b}$ is independently hydrogen, methyl, $CH_2NH_2$, $CH_2N(CH_3)_2$, $CH_2C(O)NHSO_2CH_3$, $NH_2$, $NHCH_3$, $N(CH_3)_2$,

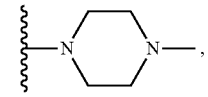

$NHCH_2COOH$, $NHC(O)CH_3$, $NHC(O)CH_2CH_2COOH$, $NHC(O)NHSO_2CH_3$, OH, $OCH_2COOH$, $OCH_2COOCH_2CH_3$

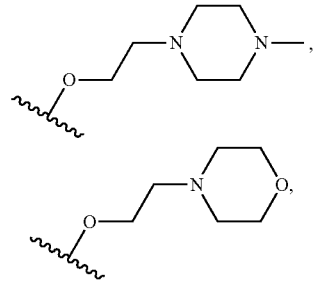

$OC(O)CH_3$, $OC(O)CH_2NH_2$, $OC(O)CH_2CH_2COOH$, $OC(O)N(CH_3)_2$,

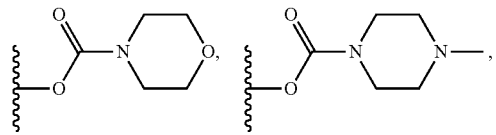

or $OC(O)NHSO_2CH_3$).

W, X, Y and Z are independently selected from N, $CR^5$, provided that no more than two of W, X, Y and Z are N. Alternatively, all of W, X, Y and Z are carbon.

each $R^5$ is independently selected from hydrogen, halo, $OR^{11}$, $S(O)_pR^{11}$, CN, $NO_2$, $COR^{11}$, $CSR^{11}$, $CO_2R^{11}$, CHO, $(C_1\text{-}C_6)$alkyl, halo$(C_1\text{-}C_6)$alkyl, halo$(C_1\text{-}C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1\text{-}C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1\text{-}C_6)$alkyl, halo$(C_1\text{-}C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

Alternatively, each $R^5$ is independently hydrogen, halo, $(C_1\text{-}C_3)$alkyl, $(C_1\text{-}C_3)$alkoxy, hydroxy, C(O)OH, $C(O)O(C_1\text{-}C_3)$alkyl, $C(O)NH_2$, $C(O)NH(C_1\text{-}C_3)$alkyl, $C(O)N((C_1\text{-}C_3)$alkyl$)_2$, $(C_1\text{-}C_3)$alkylamino, di$(C_1\text{-}C_3)$alkylamino, $NO_2$, CN, $(C_1\text{-}C_3)$haloalkyl or $(C_1\text{-}C_3)$haloalkoxy.

Each $R^{11}$ and each $R^{12}$ is independently selected from hydrogen, $(C_1\text{-}C_6)$alkyl or $(C_1\text{-}C_6)$hydroxyalkyl.

$R^{13}$ is $(C_1\text{-}C_6)$alkyl or $(C_1\text{-}C_6)$hydroxyalkyl.

Each $R^{14}$ and each $R^{15}$ is independently hydrogen or ($C_1$-$C_6$)alkyl, optionally substituted with $OR^{11}$, $NR^{11}R^{12}$, $C(O)R^{11}$, $C(S)R^{11}$, $COOR^{11}$, $C(S)OR^{11}$, $C(O)NR^{11}R^{12}$, $C(S)NR^{11}R^{12}$, $NR^{11}C(O)R^{11}$, $NR^{11}C(S)R^{11}$, $NR^{11}C(O)NR^{11}R^{12}$, $NR^{11}C(S)NR^{11}R^{12}$, $NR^{11}C(O)NHSO_2R^{11}$, $NR^{11}C(S)NHSO_2R^{11}$, $OC(O)R^{11}$, $OC(S)R^{11}$, $OC(O)NR^{11}R^{12}$, $OC(S)NR^{11}R^{12}$, $OC(O)NHSO_2R^{11}$, $OC(S)NHSO_2R^{11}$, $NR^{11}C(O)OR^{11}$, $NR^{11}C(S)OR^{11}$, $SO_2R^{11}$, $NR^{11}SO_2R^{11}$, $SO_2NR^{11}R^{12}$, $NR^{11}SO_2NR^{11}R^{12}$, Ar, HetAr, or HetCy.

Alternatively, $NR^{14}R^{15}$ taken together forms a 4, 5, 6- or 7-membered heterocyclic group containing 1 or 2 nitrogen atoms, 0 or 1 oxygen atoms and 0 or 1 sulfur atoms, said ring being optionally substituted at any one or more substitutable ring carbon with oxo, hydroxy, or ($C_1$-$C_3$)alkyl, and optionally substituted at any one or more substitutable ring nitrogen with ($C_1$-$C_3$)alkyl, $C(O)R^{11}$, $C(O)OR^{11}$ or $C(O)NR^{11}R^{12}$.

Each Ar is aryl optionally substituted with halogen, ($C_1$-$C_6$)alkyl, hydroxy, ($C_1$-$C_6$)alkoxy, ($C_1$-$C_6$)alkylamino, di($C_1$-$C_6$)alkylamino, $NO_2$, CN, $CONH_2$, ($C_1$-$C_6$)haloalkyl or ($C_1$-$C_6$)haloalkoxy.

Each HetAr is heteroaryl optionally substituted with halogen, ($C_1$-$C_6$)alkyl, hydroxy, ($C_1$-$C_6$)alkoxy, ($C_1$-$C_6$)alkylamino, di($C_1$-$C_6$)alkylamino, $NO_2$, CN, $CONH_2$, ($C_1$-$C_6$)haloalkyl or ($C_1$-$C_6$)haloalkoxy.

Each HetCy is a monocyclic heterocyclic group containing at least one ring atom selected from nitrogen, oxygen or sulfur, said ring being optionally substituted at any one or more substitutable ring carbon with oxo, hydroxy, or ($C_1$-$C_3$)alkyl, and optionally substituted at any one or more substitutable ring nitrogen with ($C_1$-$C_3$)alkyl, $C(O)R^{11}$, $C(O)OR^{11}$ or $C(O)NR^{11}R^{12}$.

In a second embodiment, the 11β-HSD1 inhibitors of the invention are represented by a structural formula selected from any one of Structural Formulae III-XX:

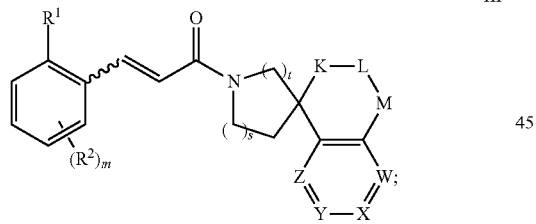

III

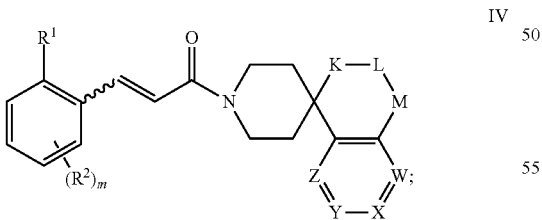

IV

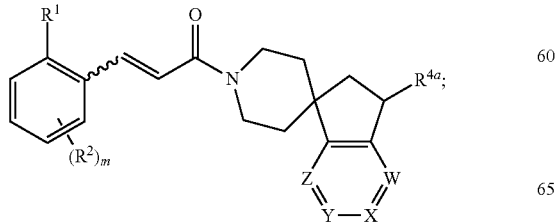

V

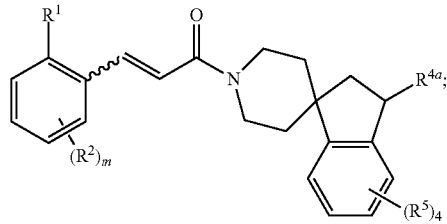

VI

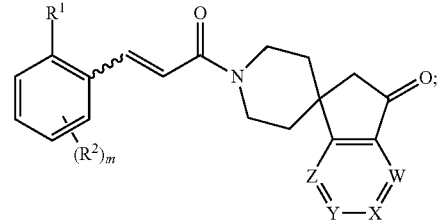

VII

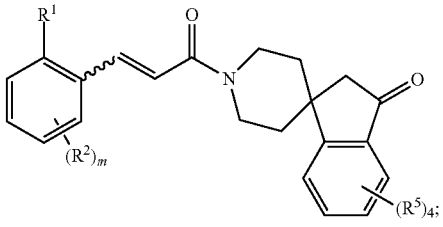

VIII

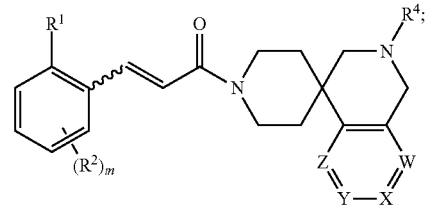

IX

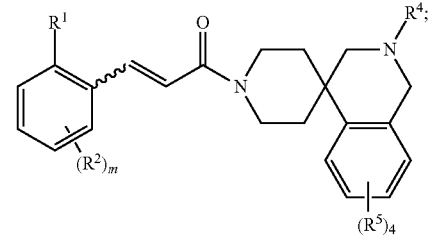

X

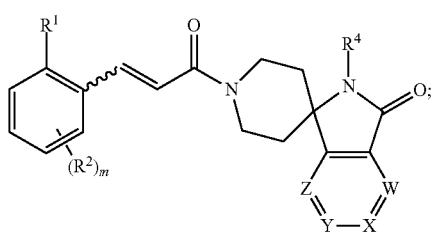

XI

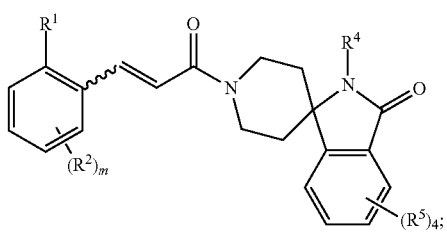

XII

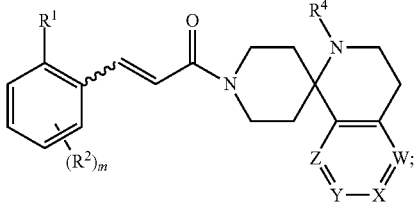

XIII

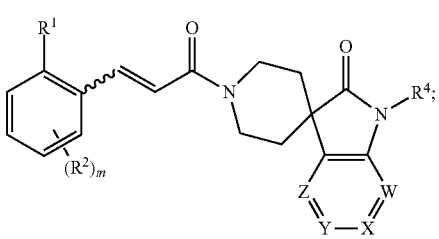

XIV

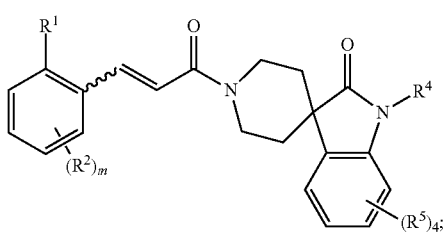

XV

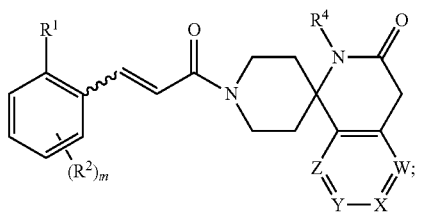

XVI

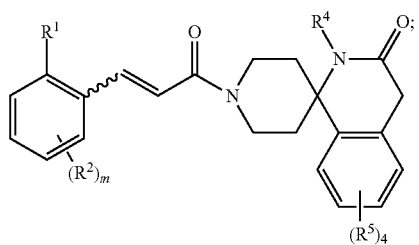

XVII

XVIII

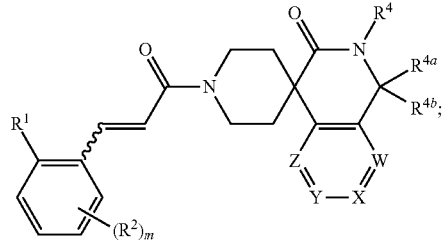

XIX

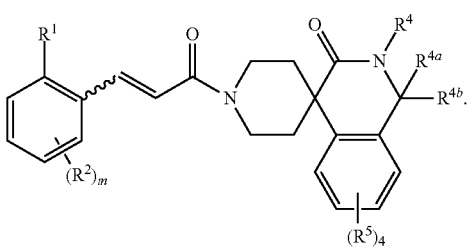

XX

Pharmaceutically acceptable salts of the 11β-HSD1 inhibitors disclosed herein (including those represented by any one of Structural Formulae III-XX) are also included in the invention. Values and alternative values for the variables in Structural Formulae III-XX are as described above for Structural Formulae I and II.

In a third embodiment, the 11β-HSD1 inhibitors of the invention are represented by a structural formula selected from any one of Structural Formulae I-XX, wherein the values for each of the variables in the structural formulae are defined below:

$R^1$ is halo, $(C_1-C_3)$alkyl, $(C_1-C_3)$haloalkyl, $(C_1-C_3)$alkoxy, or $(C_1-C_3)$haloalkoxy; and each $R^2$ is independently hydrogen, halo, $(C_1-C_3)$alkyl, hydroxy, hydroxy$(C_1-C_3)$alkyl, COO$(C_1-C_3)$alkyl, CONH$_2$, $(C_1-C_3)$alkoxy, $(C_1-C_3)$alkylamino, di$(C_1-C_3)$alkylamino, NO$_2$, CN, $(C_1-C_3)$haloalkyl or $(C_1-C_3)$haloalkoxy.

Values and alternative values for the remainder of the variables in Structural Formulae I-XX are as described for Structural Formulae I and II.

In a fourth embodiment, the 11β-HSD1 inhibitors of the invention are represented by a structural formula selected from any one of Structural Formulae I-XX, wherein the values for each of the variables in the structural formulae are defined below:

$R^1$ is halo, $(C_1-C_3)$alkyl, $(C_1-C_3)$haloalkyl, $(C_1-C_3)$alkoxy, or $(C_1-C_3)$haloalkoxy; each $R^2$ is independently hydrogen, halo, $(C_1-C_3)$alkyl, hydroxy, hydroxy$(C_1-C_3)$alkyl, COO$(C_1-C_3)$alkyl, CONH$_2$, $(C_1-C_3)$alkoxy, $(C_1-C_3)$alkylamino, di$(C_1-C_3)$alkylamino, NO$_2$, CN, $(C_1-C_3)$haloalkyl or $(C_1-C_3)$haloalkoxy; and $R^4$ is independently hydrogen, $(C_1-C_6)$alkyl, C(O)$R^{14}$, COOR$^{14}$, or SO$_2$R$^{14}$.

Values and alternative values for the remainder of the variables in Structural Formulae I-XX are as described for Structural Formulae I and II.

In a fifth embodiment, the 11β-HSD1 inhibitors of the invention are represented by a structural formula selected from any one of Structural Formulae I-XX, wherein the values for each of the variables in the structural formulae are defined below:

$R^1$ is halo, $(C_1-C_3)$alkyl, $(C_1-C_3)$haloalkyl, $(C_1-C_3)$alkoxy, or $(C_1-C_3)$haloalkoxy; each $R^2$ is independently hydrogen, halo, $(C_1-C_3)$alkyl, hydroxy, hydroxy$(C_1-C_3)$alkyl, COO$(C_1-C_3)$alkyl, CONH$_2$, $(C_1-C_3)$alkoxy, $(C_1-C_3)$alkylamino, di($C_1$-$C_3$)alkylamino, $NO_2$, CN, ($C_1$-$C_3$)haloalkyl or ($C_1$-$C_3$)haloalkoxy; and $R^4$ is independently $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, or $SO_2NR^{14}R^{15}$.

Values and alternative values for the remainder of the variables in Structural Formulae I-XX are as described for Structural Formulae I and II.

In a sixth embodiment, the 11β-HSD1 inhibitors of the invention are represented by a structural formula selected from any one of Structural Formulae I-XX, wherein the values for each of the variables in the structural formulae are defined below:

$R^1$ is halo, ($C_1$-$C_3$)alkyl, ($C_1$-$C_3$)haloalkyl, ($C_1$-$C_3$)alkoxy, or ($C_1$-$C_3$)haloalkoxy; each $R^2$ is independently hydrogen, halo, ($C_1$-$C_3$)alkyl, hydroxy, hydroxy($C_1$-$C_3$)alkyl, $COO(C_1$-$C_3)$alkyl, $CONH_2$, ($C_1$-$C_3$)alkoxy, ($C_1$-$C_3$)alkylamino, di($C_1$-$C_3$)alkylamino, $NO_2$, CN, ($C_1$-$C_3$)haloalkyl or ($C_1$-$C_3$)haloalkoxy; $R^4$ is independently hydrogen, ($C_1$-$C_6$)alkyl, $C(O)R^{14}$, $COOR^{14}$, or $SO_2R^{14}$; and each $R^{4a}$ and each $R^{41}$) is independently selected from hydrogen, $OR^{14}$, $NR^{14}R^{15}$, $C(O)NR^{14}R^{15}$, $NR^{11}C(O)R^{14}$, $NR^{11}C(O)NHSO_2R^{14}$, $NR^{11}C(O)NR^{14}R^{15}$, $OC(O)R^{14}$, $OC(O)NR^{14}R^{15}$, $OC(O)NHSO_2R^{14}$, HetCy, ($C_1$-$C_3$)alkyl, or ($C_1$-$C_3$)alkyl substituted with $NR^{14}R^{15}$, $COOR^{14}$, $C(O)NHSO_2R^{14}$, or $C(O)NR^{14}R^{15}$ (e.g., each $R^{4a}$ and each $R^{4b}$ is independently hydrogen, methyl, $CH_2NH_2$, $CH_2N(CH_3)_2$, $CH_2C(O)NHSO_2CH_3$, $NH_2$, $NHCH_3$, $N(CH_3)2$,

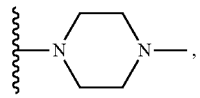

$NHCH_2COOH$, $NHC(O)CH_3$, $NHC(O)CH_2CH_2COOH$, $NHC(O)NHSO_2CH_3$, OH, $OCH_2COOH$, $OCH_2COOCH_2CH_3$,

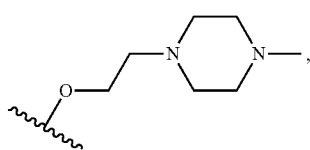

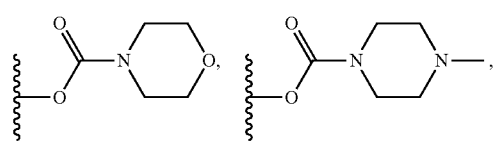

$OC(O)CH_3$, $OC(O)CH_2NH_2$, $OC(O)CH_2CH_2COOH$, $OC(O)N(CH_3)_2$, or $OC(O)NHSO_2CH_3$).

Values and alternative values for the remainder of the variables in Structural Formulae I-XX are as described for Structural Formulae I and II.

In a seventh embodiment, the 11β-HSD1 inhibitors of the invention are represented by a structural formula selected from any one of Structural Formulae I-XX, wherein the values for each of the variables in the structural formulae are defined below:

$R^1$ is halo, ($C_1$-$C_3$)alkyl, ($C_1$-$C_3$)haloalkyl, ($C_1$-$C_3$)alkoxy, or ($C_1$-$C_3$)haloalkoxy; each $R^2$ is independently hydrogen, halo, ($C_1$-$C_3$)alkyl, hydroxy, hydroxy($C_1$-$C_3$)alkyl, $COO(C_1$-$C_3)$alkyl, $CONH_2$, ($C_1$-$C_3$)alkoxy, ($C_1$-$C_3$)alkylamino, di($C_1$-$C_3$)alkylamino, $NO_2$, CN, ($C_1$-$C_3$)haloalkyl or ($C_1$-$C_3$)haloalkoxy; $R^4$ is independently $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, or $SO_2NR^{14}R^{15}$; and each $R^{4a}$ and each $R^{4b}$ is independently selected from hydrogen, $OR^{14}$, $NR^{14}R^{15}$, $C(O)NR^{14}R^{15}$, $NR^{11}C(O)R^{14}$, $NR^{11}C(O)NHSO_2R^{14}$, $NR^{11}C(O)NR^{14}R^{15}$, $OC(O)R^{14}$, $OC(O)NR^{14}R^{15}$, $OC(O)NHSO_2R^{14}$, HetCy, ($C_1$-$C_3$)alkyl, or ($C_1$-$C_3$)alkyl substituted with $NR^{14}R^{15}$, $COOR^{14}$, $C(O)NHSO_2R^{14}$, or $C(O)NR^{14}R^{15}$ (e.g., each $R^{4a}$ and each $R^{4b}$ is independently hydrogen, methyl, $CH_2NH_2$, $CH_2N(CH_3)_2$, $CH_2C(O)NHSO_2CH_3$, $NH_2$, $NHCH_3$, $N(CH_3)2$,

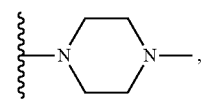

$NHCH_2COOH$, $NHC(O)CH_3$, $NHC(O)CH_2CH_2COOH$, $NHC(O)NHSO_2CH_3$, OH, $OCH_2COOH$, $OCH_2COOCH_2CH_3$,

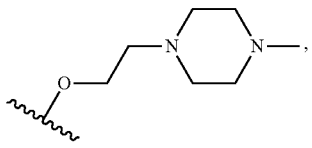

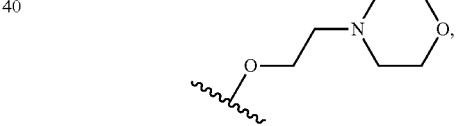

$OC(O)CH_3$, $OC(O)CH_2NH_2$, $OC(O)CH_2CH_2COOH$, $OC(O)N(CH_3)_2$,

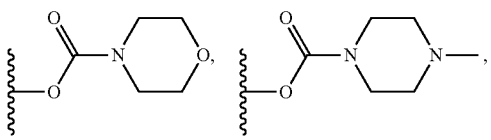

or $OC(O)NHSO_2CH_3$).

Values and alternative values for the remainder of the variables in Structural Formulae I-XX are as described for Structural Formulae I and II.

In an eighth embodiment, the 11β-HSD1 inhibitors of the invention are represented by a structural formula selected from any one of Structural Formulae I-XX, wherein the values for each of the variables in the structural formulae are defined below:

$R^1$ is halo, ($C_1$-$C_3$)alkyl, ($C_1$-$C_3$)haloalkyl, ($C_1$-$C_3$)alkoxy, or ($C_1$-$C_3$)haloalkoxy; each $R^2$ is independently hydrogen, halo, $(C_1-C_3)$alkyl, hydroxy, hydroxy$(C_1-C_3)$alkyl, COO$(C_1-C_3)$alkyl, CONH$_2$, $(C_1-C_3)$alkoxy, $(C_1-C_3)$alkylamino, di$(C_1-C_3)$alkylamino, NO$_2$, CN, $(C_1-C_3)$haloalkyl or $(C_1-C_3)$haloalkoxy; $R^4$ is independently hydrogen, $(C_1-C_6)$alkyl, C(O)$R^{14}$, COO$R^{14}$, or SO$_2R^{14}$; each $R^{4a}$ and each $R^{4b}$ is independently selected from hydrogen, O$R^{14}$, N$R^{14}R^{15}$, C(O)N$R^{14}R^{15}$, N$R^{11}$C(O)$R^{14}$, N$R^{11}$C(O)NHSO$_2R^{14}$, N$R^{11}$C(O)N$R^{14}R^{15}$, OC(O)$R^{14}$, OC(O)N$R^{14}R^{15}$, OC(O)NHSO$_2R^{14}$, HetCy, $(C_1-C_3)$alkyl, or $(C_1-C_3)$alkyl substituted with N$R^{14}R^{15}$, COO$R^{14}$, C(O)NHSO$_2R^{14}$, or C(O)N$R^{14}R^{15}$ (e.g., each $R^{4a}$ and each $R^{4b}$ is independently hydrogen, methyl, CH$_2$NH$_2$, CH$_2$N(CH$_3$)$_2$, CH$_2$C(O)NHSO$_2$CH$_3$, NH$_2$, NHCH$_3$, N(CH$_3$)2,

NHCH$_2$COOH, NHC(O)CH$_3$, NHC(O)CH$_2$CH$_2$COOH, NHC(O)NHSO$_2$CH$_3$, OH, OCH$_2$COOH, OCH$_2$COOCH$_2$CH$_3$,

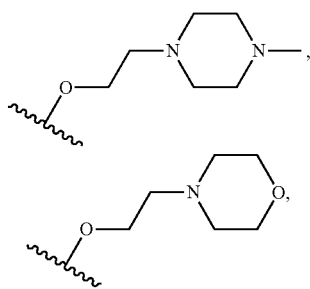

OC(O)CH$_3$, OC(O)CH$_2$NH$_2$, OC(O)CH$_2$CH$_2$COOH, OC(O)N(CH$_3$)$_2$,

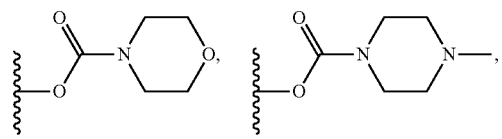 [SMILES: *OC(=O)N1CCOCC1 ; *OC(=O)N1CCN(C)CC1]

or OC(O)NHSO$_2$CH$_3$); and $R^5$ is independently hydrogen, halo, $(C_1-C_3)$alkyl, $(C_1-C_3)$alkoxy, hydroxy, C(O)OH, C(O)O$(C_1-C_3)$alkyl, C(O)NH$_2$, C(O)NH$(C_1-C_3)$alkyl, C(O)N$((C_1-C_3)$alkyl$)_2$, $(C_1-C_3)$alkylamino, di$(C_1-C_3)$alkylamino, NO$_2$, CN, $(C_1-C_3)$haloakyl or $(C_1-C_3)$haloalkoxy.

Values and alternative values for the remainder of the variables in Structural Formulae I-XX are as described for Structural Formulae I and II.

In a ninth embodiment, the 11β-HSD1 inhibitors of the invention are represented by a structural formula selected from any one of Structural Formulae I-XX, wherein the values for each of the variables in the structural formulae are defined below:

$R^1$ is halo, $(C_1-C_3)$alkyl, $(C_1-C_3)$haloalkyl, $(C_1-C_3)$alkoxy, or $(C_1-C_3)$haloalkoxy; each $R^2$ is independently hydrogen, halo, $(C_1-C_3)$alkyl, hydroxy, hydroxy$(C_1-C_3)$alkyl, COO$(C_1-C_3)$alkyl, CONH$_2$, $(C_1-C_3)$alkoxy, $(C_1-C_3)$alkylamino, di$(C_1-C_3)$alkylamino, NO$_2$, CN, $(C_1-C_3)$haloalkyl or $(C_1-C_3)$haloalkoxy; $R^4$ is independently C(O)$R^{14}$, C(S)$R^{14}$, COO$R^{14}$, C(S)O$R^{14}$, C(O)N$R^{14}R^{15}$, C(S)N$R^{14}R^{15}$, SO$_2R^{14}$, or SO$_2$N$R^{14}R^{15}$; each $R^{4a}$ and each $R^{4b}$ is independently selected from hydrogen, O$R^{14}$, N$R^{14}R^{15}$, C(O)N$R^{14}R^{15}$, N$R^{11}$C(O)$R^{14}$, N$R^{11}$C(O)NHSO$_2R^{14}$, N$R^{11}$C(O)N$R^{14}R^{15}$, OC(O)$R^{14}$, OC(O)N$R^{14}R^{15}$, OC(O)NHSO$_2R^{14}$, HetCy, $(C_1-C_3)$alkyl, or $(C_1-C_3)$alkyl substituted with N$R^{14}R^{15}$, COO$R^{14}$, C(O)NHSO$_2R^{14}$, or C(O)N$R^{14}R^{15}$ (e.g., each $R^{4a}$ and each $R^{4b}$ is independently hydrogen, methyl, CH$_2$NH$_2$, CH$_2$N(CH$_3$)$_2$, CH$_2$C(O)NHSO$_2$CH$_3$, NH$_2$, NHCH$_3$, N(CH$_3$)2,

NHCH$_2$COOH, NHC(O)CH$_3$, NHC(O)CH$_2$CH$_2$COOH, NHC(O)NHSO$_2$CH$_3$, OH, OCH$_2$COOH, OCH$_2$COOCH$_2$CH$_3$,

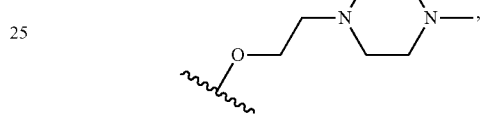

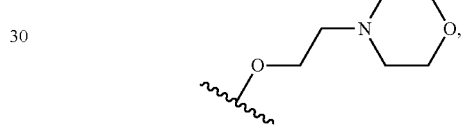

OC(O)CH$_3$, OC(O)CH$_2$NH$_2$, OC(O)CH$_2$CH$_2$COOH, OC(O)N(CH$_3$)$_2$,

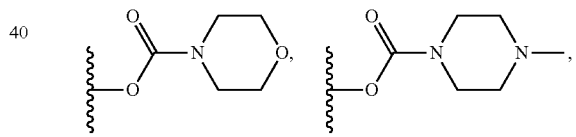

or OC(O)NHSO$_2$CH$_3$); and $R^5$ is independently hydrogen, halo, $(C_1-C_3)$alkyl, $(C_1-C_3)$alkoxy, hydroxy, C(O)OH, C(O)O$(C_1-C_3)$alkyl, C(O)NH$_2$, C(O)NH$(C_1-C_3)$alkyl, C(O)N$((C_1-C_3)$alkyl$)_2$, $(C_1-C_3)$alkylamino, di$(C_1-C_3)$alkylamino, NO$_2$, CN, $(C_1-C_3)$haloakyl or $(C_1-C_3)$haloalkoxy.

Values and alternative values for the remainder of the variables in Structural Formulae I-XX are as described for Structural Formulae I and II.

In a tenth embodiment, the 11β-HSD1 inhibitors of the invention are represented by a structural formula selected from any one of Structural Formulae I-XX, wherein the values for each of the variables in the structural formulae are defined below:

$R^1$ is halo, $(C_1-C_3)$alkyl, $(C_1-C_3)$haloalkyl, $(C_1-C_3)$alkoxy, or $(C_1-C_3)$haloalkoxy; each $R^2$ is independently hydrogen, halo, $(C_1-C_3)$alkyl, hydroxy, hydroxy$(C_1-C_3)$alkyl, COO$(C_1-C_3)$alkyl, CONH$_2$, $(C_1-C_3)$alkoxy, $(C_1-C_3)$alkylamino, di$(C_1-C_3)$alkylamino, NO$_2$, CN, $(C_1-C_3)$haloalkyl or $(C_1-C_3)$haloalkoxy; $R^4$ is independently hydrogen, $(C_1-C_6)$alkyl, C(O)$R^{14}$, COO$R^{14}$, or SO$_2R^{14}$; each $R^{4a}$ and each $R^{4b}$ is independently selected from hydrogen, O$R^{14}$, N$R^{14}R^{15}$, C(O)N$R^{14}R^{15}$, N$R^{11}$C(O)$R^{14}$, N$R^{11}$C(O)NHSO$_2R^{14}$, NR$^{11}$C(O)NR$^{14}$R$^{15}$, OC(O)R$^{14}$, OC(O)NR$^{14}$R$^{15}$, OC(O)NHSO$_2$R$^{14}$, HetCy, (C$_1$-C$_3$)alkyl, or (C$_1$-C$_3$)alkyl substituted with NR$^{14}$R$^{15}$, COOR$^{14}$, C(O)NHSO$_2$R$^{14}$, or C(O)NR$^{14}$R$^{15}$ (e.g., each R$^{4a}$ and each R$^{4b}$ is independently hydrogen, methyl, CH$_2$NH$_2$, CH$_2$N(CH$_3$)$_2$, CH$_2$C(O)NHSO$_2$CH$_3$, NH$_2$, NHCH$_3$, N(CH$_3$)2,

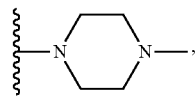

NHCH$_2$COOH, NHC(O)CH$_3$, NHC(O)CH$_2$CH$_2$COOH, NHC(O)NHSO$_2$CH$_3$, OH, OCH$_2$COOH, OCH$_2$COOCH$_2$CH$_3$,

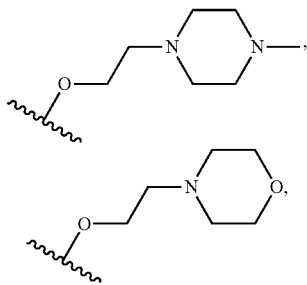

OC(O)CH$_3$, OC(O)CH$_2$NH$_2$, OC(O)CH$_2$CH$_2$COOH, OC(O)N(CH$_3$)$_2$,

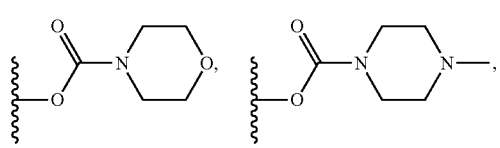 [SMILES: *OC(=O)N1CCOCC1 ; *OC(=O)N1CCN(C)CC1]

or OC(O)NHSO$_2$CH$_3$); R$^5$ is independently hydrogen, halo, (C$_1$-C$_3$)alkyl, (C$_1$-C$_3$)alkoxy, hydroxy, C(O)OH, C(O)O(C$_1$-C$_3$)alkyl, C(O)NH$_2$, C(O)NH(C$_1$-C$_3$)alkyl, C(O)N((C$_1$-C$_3$)alkyl)$_2$, (C$_1$-C$_3$)alkylamino, di(C$_1$-C$_3$)alkylamino, NO$_2$, CN, (C$_1$-C$_3$)haloakyl or (C$_1$-C$_3$)haloalkoxy; and R$^{14}$ is hydrogen and R$^{15}$ is independently hydrogen, (C$_1$-C$_3$)alkyl, hydroxy (C$_1$-C$_3$)alkyl, amino(C$_1$-C$_3$)alkyl, (C$_1$-C$_3$)alkylamino(C$_1$-C$_3$)alkyl, or di-(C$_1$-C$_3$)alkylamino(C$_1$-C$_3$)alkyl.

Values and alternative values for the remainder of the variables in Structural Formulae I-XX are as described for Structural Formulae I and II.

In an eleventh embodiment, the 11β-HSD1 inhibitors of the invention are represented by a structural formula selected from any one of Structural Formulae I-XX, wherein the values for each of the variables in the structural formulae are defined below:

R$^1$ is halo, (C$_1$-C$_3$)alkyl, (C$_1$-C$_3$)haloalkyl, (C$_1$-C$_3$)alkoxy, or (C$_1$-C$_3$)haloalkoxy; each R$^2$ is independently hydrogen, halo, (C$_1$-C$_3$)alkyl, hydroxy, hydroxy(C$_1$-C$_3$)alkyl, COO(C$_1$-C$_3$)alkyl, CONH$_2$, (C$_1$-C$_3$)alkoxy, (C$_1$-C$_3$)alkylamino, di(C$_1$-C$_3$)alkylamino, NO$_2$, CN, (C$_1$-C$_3$)haloalkyl or (C$_1$-C$_3$)haloalkoxy; R$^4$ is independently hydrogen, (C$_1$-C$_6$)alkyl, C(O)R$^{14}$, COOR$^{14}$, or SO$_2$R$^{14}$; each R$^{4a}$ and each R$^{4b}$ is independently selected from hydrogen, OR$^{14}$, NR$^{14}$R$^{15}$, C(O)NR$^{14}$R$^{15}$, NR$^{11}$C(O)R$^{14}$, NR$^{11}$C(O)NHSO$_2$R$^{14}$, NR$^{11}$C(O)NR$^{14}$R$^{15}$, OC(O)R$^{14}$, OC(O)NR$^{14}$R$^{15}$, OC(O)NHSO$_2$R$^{14}$, HetCy, (C$_1$-C$_3$)alkyl, or (C$_1$-C$_3$)alkyl substituted with NR$^{14}$R$^{15}$, COOR$^{14}$, C(O)NHSO$_2$R$^{14}$, or C(O)NR$^{14}$R$^{15}$ (e.g., each R$^{4a}$ and each R$^{4b}$ is independently hydrogen, methyl, CH$_2$NH$_2$, CH$_2$N(CH$_3$)$_2$, CH$_2$C(O)NHSO$_2$CH$_3$, NH$_2$, NHCH$_3$, N(CH$_3$)2,

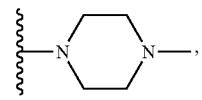

NHCH$_2$COOH, NHC(O)CH$_3$, NHC(O)CH$_2$CH$_2$COOH, NHC(O)NHSO$_2$CH$_3$, OH, OCH$_2$COOH, OCH$_2$COOCH$_2$CH$_3$,

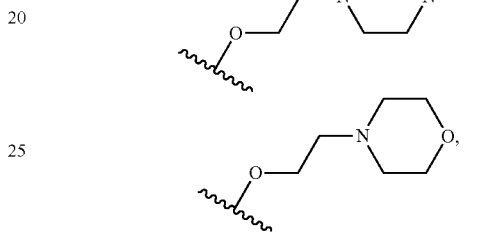

OC(O)CH$_3$, OC(O)CH$_2$NH$_2$, OC(O)CH$_2$CH$_2$COOH, OC(O)N(CH$_3$)$_2$,

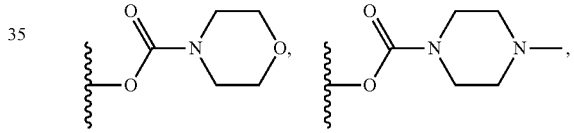

or OC(O)NHSO$_2$CH$_3$); R$^5$ is independently hydrogen, halo, (C$_1$-C$_3$)alkyl, (C$_1$-C$_3$)alkoxy, hydroxy, C(O)OH, C(O)O(C$_1$-C$_3$)alkyl, C(O)NH$_2$, C(O)NH(C$_1$-C$_3$)alkyl, C(O)N((C$_1$-C$_3$)alkyl)$_2$, (C$_1$-C$_3$)alkylamino, di(C$_1$-C$_3$)alkylamino, NO$_2$, CN, (C$_1$-C$_3$)haloakyl or (C$_1$-C$_3$)haloalkoxy; and NR$^{14}$R$^{15}$ taken together forms a 5- or 6-membered heterocyclic group containing 1 or 2 nitrogen atoms, 0 or 1 oxygen atoms and 0 or 1 sulfur atoms, said ring being optionally substituted at any one or more substitutable ring carbon with oxo, hydroxy, or (C$_1$-C$_3$)alkyl, and optionally substituted at any one or more substitutable ring nitrogen with (C$_1$-C$_3$)alkyl, C(O)R$^{11}$, C(O)OR$^{11}$ or C(O)NR$^{11}$R$^{12}$.

Values and alternative values for the remainder of the variables in Structural is Formulae I-XX are as described for Structural Formulae I and II.

In a twelfth embodiment, the 11β-HSD1 inhibitors of the invention are represented by a structural formula selected from any one of Structural Formulae I-XX, wherein the values for each of the variables in the structural formulae are defined below:

R$^1$ is halo, (C$_1$-C$_3$)alkyl, (C$_1$-C$_3$)haloalkyl, (C$_1$-C$_3$)alkoxy, or (C$_1$-C$_3$)haloalkoxy; each R$^2$ is independently hydrogen, halo, (C$_1$-C$_3$)alkyl, hydroxy, hydroxy(C$_1$-C$_3$)alkyl, COO(C$_1$-C$_3$)alkyl, CONH$_2$, (C$_1$-C$_3$)alkoxy, (C$_1$-C$_3$)alkylamino, di(C$_1$-C$_3$)alkylamino, NO$_2$, CN, (C$_1$-C$_3$)haloalkyl or (C$_1$-C$_3$)haloalkoxy; R$^4$ is independently C(O)R$^{14}$, C(S)R$^{14}$, COOR$^{14}$, C(S)OR$^{14}$, C(O)NR$^{14}$R$^{15}$, C(S)NR$^{14}$R$^{15}$, SO$_2$R$^{14}$, or $SO_2NR^{14}R^{15}$; each $R^{4a}$ and each $R^{4b}$ is independently selected from hydrogen, $OR^{14}$, $NR^{14}R^{15}$, $C(O)NR^{14}R^{15}$, $NR^{11}C(O)R^{14}$, $NR^{11}C(O)NHSO_2R^{14}$, $NR^{11}C(O)NR^{14}R^{15}$, $OC(O)R^{14}$, $OC(O)NR^{14}R^{15}$, $OC(O)NHSO_2R^{14}$, HetCy, $(C_1-C_3)$alkyl, or $(C_1-C_3)$alkyl substituted with $NR^{14}R^{15}$, $COOR^{14}$, $C(O)NHSO_2R^{14}$, or $C(O)NR^{14}R^{15}$ (e.g., each $R^{4a}$ and each $R^{4b}$ is independently hydrogen, methyl, $CH_2NH_2$, $CH_2N(CH_3)_2$, $CH_2C(O)NHSO_2CH_3$, $NH_2$, $NHCH_3$, $N(CH_3)_2$,

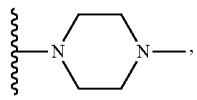

$NHCH_2COOH$, $NHC(O)CH_3$, $NHC(O)CH_2CH_2COOH$, $NHC(O)NHSO_2CH_3$, $OH$, $OCH_2COOH$, $OCH_2COOCH_2CH_3$,

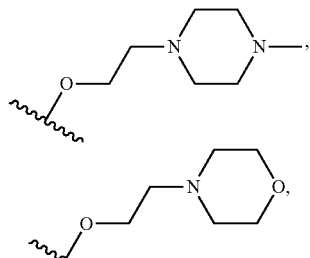

$OC(O)CH_3$, $OC(O)CH_2NH_2$, $OC(O)CH_2CH_2COOH$, $OC(O)N(CH_3)_2$,

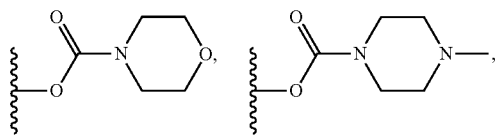 [SMILES: *OC(=O)N1CCOCC1 ; *OC(=O)N1CCN(C)CC1]

or $OC(O)NHSO_2CH_3$); $R^5$ is independently hydrogen, halo, $(C_1-C_3)$alkyl, $(C_1-C_3)$alkoxy, hydroxy, $C(O)OH$, $C(O)O(C_1-C_3)$alkyl, $C(O)NH_2$, $C(O)NH(C_1-C_3)$alkyl, $C(O)N((C_1-C_3)$alkyl$)_2$, $(C_1-C_3)$alkylamino, di$(C_1-C_3)$alkylamino, $NO_2$, $CN$, $(C_1-C_3)$haloakyl or $(C_1-C_3)$haloalkoxy; and $R^{14}$ is hydrogen and $R^{15}$ is independently hydrogen, $(C_1-C_3)$alkyl, hydroxy$(C_1-C_3)$alkyl, amino$(C_1-C_3)$alkyl, $(C_1-C_3)$alkylamino$(C_1-C_3)$alkyl, or di-$(C_1-C_3)$alkylamino$(C_1-C_3)$alkyl.

Values and alternative values for the remainder of the variables in Structural Formulae I-XX are as described for Structural Formulae I and II.

In a thirteenth embodiment, the 11β-HSD1 inhibitors of the invention are represented by a structural formula selected from any one of Structural Formulae I-XX, wherein the values for each of the variables in the structural formulae are defined below:

$R^1$ is halo, $(C_1-C_3)$alkyl, $(C_1-C_3)$haloalkyl, $(C_1-C_3)$alkoxy, or $(C_1-C_3)$haloalkoxy; each $R^2$ is independently hydrogen, halo, $(C_1-C_3)$alkyl, hydroxy, hydroxy$(C_1-C_3)$alkyl, $COO(C_1-C_3)$alkyl, $CONH_2$, $(C_1-C_3)$alkoxy, $(C_1-C_3)$alkylamino, di$(C_1-C_3)$alkylamino, $NO_2$, $CN$, $(C_1-C_3)$haloalkyl or $(C_1-C_3)$haloalkoxy; $R^4$ is independently $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, or $SO_2NR^{14}R^{15}$; each $R^{4a}$ and each $R^{41i}$ is independently selected from hydrogen, $OR^{14}$, $NR^{14}R^{15}$, $C(O)NR^{14}R^{15}$, $NR^{11}C(O)R^{14}$, $NR^{11}C(O)NHSO_2R^{14}$, $NR^{11}C(O)NR^{14}R^{15}$, $OC(O)R^{14}$, $OC(O)NR^{14}R^{15}$, $OC(O)NHSO_2R^{14}$, HetCy, $(C_1-C_3)$alkyl, or $(C_1-C_3)$alkyl substituted with $NR^{14}R^{15}$, $COOR^{14}$, $C(O)NHSO_2R^{14}$, or $C(O)NR^{14}R^{15}$ (e.g., each $R^{4a}$ and each $R^{4b}$ is independently hydrogen, methyl, $CH_2NH_2$, $CH_2N(CH_3)_2$, $CH_2C(O)NHSO_2CH_3$, $NH_2$, $NHCH_3$, $N(CH_3)_2$,

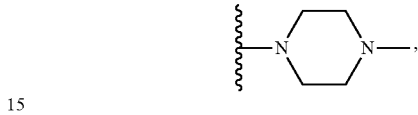

$NHCH_2COOH$, $NHC(O)CH_3$, $NHC(O)CH_2CH_2COOH$, $NHC(O)NHSO_2CH_3$, $OH$, $OCH_2COOH$, $OCH_2COOCH_2CH_3$,

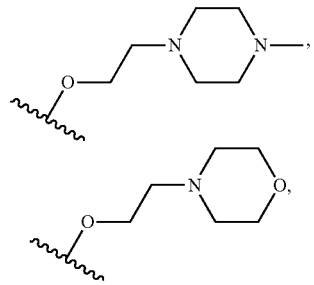

$OC(O)CH_3$, $OC(O)CH_2NH_2$, $OC(O)CH_2CH_2COOH$, $OC(O)N(CH_3)_2$,

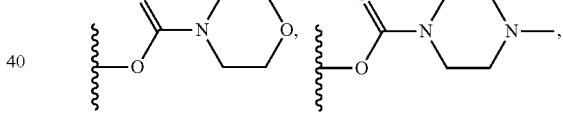

or $OC(O)NHSO_2CH_3$); $R^5$ is independently hydrogen, halo, $(C_1-C_3)$alkyl, $(C_1-C_3)$alkoxy, hydroxy, $C(O)OH$, $C(O)O(C_1-C_3)$alkyl, $C(O)NH_2$, $C(O)NH(C_1-C_3)$alkyl, $C(O)N((C_1-C_3)$alkyl$)_2$, $(C_1-C_3)$alkylamino, di$(C_1-C_3)$alkylamino, $NO_2$, $CN$, $(C_1-C_3)$haloakyl or $(C_1-C_3)$haloalkoxy; and $NR^{14}R^{15}$ taken together forms a 5- or 6-membered heterocyclic group containing 1 or 2 nitrogen atoms, 0 or 1 oxygen atoms and 0 or 1 sulfur atoms, said ring being optionally substituted at any one or more substitutable ring carbon with oxo, hydroxy, or $(C_1-C_3)$alkyl, and optionally substituted at any one or more substitutable ring nitrogen with $(C_1-C_3)$alkyl, $C(O)R^{11}$, $C(O)OR^{11}$ or $C(O)NR^{11}R^{12}$.

Values and alternative values for the remainder of the variables in Structural Formulae I-XX are as described for Structural Formulae I and II.

Specific 11β-HSD1 inhibitors of the invention and pharmaceutically acceptable salts thereof are provided in Examples 1-105 and Prophetic Examples 1-34 below.

Specific examples of compounds of Formulae I-XX may exist in various stereoisomeric or tautomeric forms. The invention encompasses all such forms, including active compounds in the form of essentially pure enantiomers, racemic mixtures, and tautomers, including forms those not depicted structurally.

When any variable (e.g., aryl, heterocyclyl, $R^1$, $R^2$, etc.) occurs more than once in a compound, its definition on each occurrence is independent of any other occurrence.

The term "alkyl", used alone or as part of a larger moiety such as "alkoxy", "hydroxyalkyl", "alkoxyalkyl", "alkylamine", "dialkyamine", "alkoxycarbonyl" or "alkylaminocarbonyl", means a saturated straight or branched hydrocarbon radical having (unless otherwise specified) 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a saturated hydrocarbon ring having 3-8 carbon atoms and includes, for example, cyclopropyl, cyclobutyl, cyclopentyl, cyclohexyl, cycloheptyl, cyclooctyl, and the like.

The term "aryl" means a 6-10 membered carbocyclic aromatic monocyclic or polycyclic ring system, such as phenyl or naphthyl. The term "aryl" may be used interchangeably with the terms "aryl ring" "aromatic ring", "aryl group" and "aromatic group".

"Heteroaromatic group", used alone or as part of a larger moiety as in "heteroaralkyl" or "heteroarylalkoxy", means a 5-10 membered monovalent monocyclic and polycyclic aromatic group radical containing 1 to 4 heteroatoms independently selected from N, O, and S. Heteroaryl groups include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, quinazolinyl, benzothienyl, benzofuranyl, 2,3-dihydrobenzofuranyl, benzodioxolyl, benzimidazolyl, indazolyl, benzisoxazolyl, benzoxazolyl, benzothiazolyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl. The terms "heteroaryl", "heteroaromatic", "heteroaryl ring", "heteroaryl group" and "heteroaromatic group" are used interchangeably herein.

The term "heterocyclic group" means a 4-, 5-, 6- and 7-membered saturated or partially unsaturated heterocyclic ring containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide. The terms "heterocyclyl", "heterocycle", "heterocyclic group" and "heterocyclic ring" are used interchangeably herein.

The term "ring atom" is an atom such as C, N, O or S that is in the ring of an aryl group, heteroaryl group, cycloalkyl group or heterocyclic group. A "substitutable ring atom" in an aryl, heteroaryl cycloalkyl or heterocyclic is a carbon or nitrogen atom in the aryl, heteroaryl, cycloalkyl or heterocyclic group that is bonded to at least one hydrogen atom. The hydrogen(s) can be optionally replaced with a suitable substituent group. Thus, the term "substitutable ring atom" does not include ring carbon or nitrogen atoms when the structure depicts that they are not attached to any hydrogen atoms. For example, the carbon atom in the phenyl ring that is attached to the double bond in Structural Formulas (III)-(XX) is not a substitutable ring carbon atom.

Suitable substituents for an alkyl, aryl, heteroaryl and heterocyclic group are those which do not significantly reduce the ability of the compound to inhibit the activity of 11β-HSD1. Unless otherwise specified, suitable substituents for an alkyl, aryl, heteroaryl and heterocyclyl include halo, $OR^{11}$, $S(O)_pR^{11}$, CN, $NO_2$, $C(O)R^{11}$, $C(S)R^{11}$, $CO_2R^{11}$, CHO, ($C_1$-$C_6$)alkyl, halo($C_1$-$C_6$)alkyl, halo($C_1$-$C_6$)alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a ($C_1$-$C_6$)alkyl substituted with halo, $OR^{11}$, $S(O)_pR^{11}$, CN, $NO_2$, $C(O)R^{11}$, $C(S)R^{11}$, $CO_2R^{11}$, CHO, ($C_1$-$C_6$)alkyl, halo($C_1$-$C_6$)alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$, wherein $R^{11-13}$ are as described above. Preferred substituents an alkyl, aryl, heteroaryl and heterocyclyl include, unless otherwise specified, halogen, ($C_1$-$C_6$)alkyl, hydroxy, ($C_1$-$C_6$)alkoxy, ($C_1$-$C_6$)alkylamino, di($C_1$-$C_6$)alkylamino, $NO_2$, CN, $CONH_2$, ($C_1$-$C_6$)haloakyl or ($C_1$-$C_6$)haloalkoxy.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the disclosed 11β-HSD1 inhibitors containing an acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'- bisdehydroabietylamine, glucamine, N-methylglucamine, collidine, quinine, quinoline, and basic amino acids such as lysine and arginine.

When a disclosed compound or its pharmaceutically acceptable salt is named or depicted by structure, it is to be understood that solvates or hydrates of the compound or its pharmaceutically acceptable salts are included as well as anhydrous forms of the compound and forms without solvent. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include stoichiometric hydrates as well as compositions containing variable amounts of water.

When a disclosed compound or its pharmaceutically acceptable salt is named or depicted by structure, it is to be understood that the compound, including solvates thereof, may exist in crystalline forms, non-crystalline forms or a mixture thereof. The compound or its pharmaceutically acceptable salts or solvates may also exhibit polymorphism (i.e. the capacity to occur in different crystalline forms). These different crystalline forms are typically known as "polymorphs." It is to be understood that when named or depicted by structure, the disclosed compound and its pharmaceutically acceptable salts, solvates or hydrates also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

The invention also includes various isomers and mixtures thereof "Isomer" refers to compounds that have the same composition and molecular weight but differ in physical and/or chemical properties. The structural difference may be in constitution (geometric isomers) or in the ability to rotate the plane of polarized light (stereoisomers).

Certain of the disclosed 11β-HSD1 inhibitors may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

Many of the disclosed 11β-HSD-1 inhibitors have a double bond(s). When the bonding of a group to the double bond is represented with a ' ' the configuration about the double bond can be Z, E or a mixture thereof.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When a disclosed compound is named or depicted by structure without indicating the stereochemistry, and the compound has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When the stereochemistry of a disclosed compound is named or depicted by structure, the named or depicted stereoisomer is at least 60%, 70%, 80%, 90%, 95%, 98%, 99% or 99.9% by weight pure relative to the other stereoisomers. When a single enantiomer is named or depicted by structure, the depicted or named enantiomer is at least 60%, 70%, 80%, 90%, 95%, 98%, 99% or 99.9% by weight optically pure. Percent optical purity by weight is the ratio of the weight of the enantiomer over the weight of the enantiomer plus the weight of its optical isomer. When a single geometric isomer, e.g., a geometric isomer with a double bond, is depicted by name or structure and the stereochemistry about the double is indicated, the compound is considered to be at least 60%, 70%, 80%, 90%, 95%, 98%, 99% or 99.9% stereochemically pure by weight. Percent stereochemically purity by weight is the ratio of the weight of the geometric isomer over the weight of the both geometric isomers. For example, 99% stereochemically pure means that at least 99% by weight of the compound is the indicated stereoisomer.

A pharmaceutical composition of the invention may, alternatively or in addition to a compound of Formulae I-XX, comprise a pharmaceutically acceptable salt of a compound of Formulae I-XX, or a prodrug or pharmaceutically active metabolite of such a compound or salt and one or more pharmaceutically acceptable carriers therefor.

"Effective amount" means that amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 10 mg/kg/day, preferably from about 0.5 mg/kg/day to 5 mg/kg/day.

"Inhibiting 11β-HSD1" means to decrease the activity of the 11β-HSD1 enzyme.

"Modulating 11β-HSD1" means to impact the activity of the 11β-HSD1 enzyme by altering its natural activity. Modulation can be analogous to inhibition when a disease or disorder relating to the activity 11β-HSD1 would be effectively treated by suppressing the activity of the enzyme.

"Pharmaceutically acceptable carrier" means compounds and compositions that are of sufficient purity and quality for use in the formulation of a composition of the invention and that, when appropriately administered to an animal or human, do not produce an adverse reaction.

"Treatment" or "treating", as used herein, includes prophylactic and therapeutic treatment. "Therapeutic treatment" includes partially or totally inhibiting, delaying, or reducing the severity of the disease or disorder related to 11β-HSD1. "Prophylactic treatment" encompasses administration of a compound of the invention to a subject susceptible to a disease or disorder related to the activity or expression of 11β-HSD1 in an effort to reduce the likelihood of a subject developing the disease or disorder, or slowing or preventing progression of the disease. Prophylactic treatment includes suppression (partially or completely) of the disease or disorder, and further includes reducing the severity of the disease or disorder, if onset occurs. Prophylactic treatment is particularly advantageous for administration to mammals at risk for developing a disease or disorder related to 11β-HSD1.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally.

It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersable granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Tablets, powders, cachets, lozenges, fast-melt strips, capsules and pills can be used as solid dosage forms containing the active ingredient suitable for oral administration.

For preparing suppositories, a low melting wax, such as a mixture of fatty acid glycerides or cocoa butter, is first melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethyl cellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, metabolic syndrome, insulin resistance, cardiovascular disease, dyslipidemia, atherosclerosis, lipodystrophy, osteoporosis, glaucoma, Cushing's syndrome, depression, anxiety and Alzheimer's disease, cognitive decline (including age-related cognitive decline), polycystic ovarian syndrome and infertility. In addition, compounds modulate the function of B and T cells of the immune system.

A pharmaceutical composition of the invention may, alternatively or in addition to a compound of Formulae I-XX, comprise a pharmaceutically acceptable salt of a compound of Formulae I-XX, or a prodrug or pharmaceutically active metabolite of such a compound or salt and one or more pharmaceutically acceptable carriers therefor.

The invention includes a therapeutic method for treating or ameliorating an 11β-HSD1 mediated disorder in a mammal in need thereof comprising administering to a subject in need thereof an effective amount of a compound of Formulae I-XX, or the enantiomers, diastereomers, or salts thereof or composition thereof.

The compounds of the invention are useful for ameliorating or treating disorders or diseases in which decreasing the level of cortisol is effective in treating a disease state. Thus, the compounds of the invention can be used in the treatment or prevention of diabetes mellitus, obesity, symptoms of metabolic syndrome, glucose intolerance, hyperglycemia, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X.

The term "mammal" is preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The disclosed 11β-HSD1 inhibitors can be used alone or in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitazone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs; GLP-1 analogs; DPP-IV inhibitors, such as Januvia® (sitagliptin, Merck); PTB-1B inhibitors; protein kinase inhibitors (including AMP-activated protein kinase inhibitors); glucagon antagonists; glycogen synthase kinase-3 beta inhibitors; glucose-6-phosphatase inhibitors; glycogen phosphorylase inhibitors; sodium glucose co-transporter inhibitors, and α-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates and ezetimibe. Agents for the treatment of hypertension include α-blockers, β-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of any one of Structural Formulae I-XX or composition thereof in a combination therapy with one or more other 11β-HSD1 inhibitors (whether such inhibitors are also compounds of any one of Structural Formulae I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); Janumet® (sitagliptin and metformin, Merck) and Glucovance® (glyburide and metformin HCl, Bristol Myers Squibb).

The following abbreviations have the indicated meanings:

| Abbreviation | Meaning |
|---|---|
| Boc | tert-butoxy carbonyl or t-butoxy carbonyl |
| (Boc)$_2$O | di-tert-butyl dicarbonate |
| BOP | (Benzotriazole-1-yl-oxy-tris-(dimethylamino)-phosphonium hexafluorophosphate) |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC, EDC•HCl, EDCI | 1-[3-(dimethylamino)propyl]-3-ethylcarbodiimide hydrochloride |
| Equiv | equivalents |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |

| Abbreviation | Meaning |
|---|---|
| TFA | trifluoroacetic acid |
| Tlc, TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthetic Methods

Compounds of Formulae I or II can be prepared by several processes. In the discussion below, $R^1$, $R^2$, $R^3$, $R^4$, $R^{4a}$, $R^{4b}$, $R^5$, K, L, M, W, X, Y, Z, m, n and p have the meanings indicated above unless otherwise noted. In cases where the synthetic intermediates and final products of Formulae I or II described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process, a compound of Formula XXI, can be prepared by reaction of a cinnamic acid derivative of Formula XXII, wherein $R^a$ is a leaving group such as chloride, 1-imidazolyl, methanesulfonyloxy or 1-succinimidyloxy, with a spirocyclic amine of Formula XXIII. Alternatively a cinnamic acid of Formula XXII, wherein $R^a$ is OH, may be activated in situ by use of a peptide coupling reagent such as EDCI in the presence of HOBt, HATU, HBTU or BOP

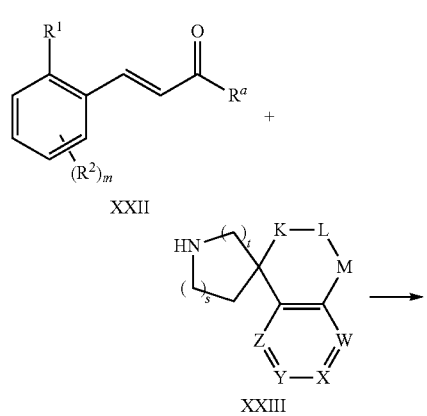

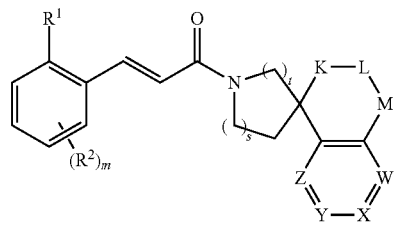

Many cinnamic acids of Formula XXII can be purchased. Cinnamic acids of Formula XXII, wherein $R^a$ is OH, can be prepared by reaction of benzaldehydes of Formula XXIV and malonic acid (Formula XXV) under Knoevenagel conditions.

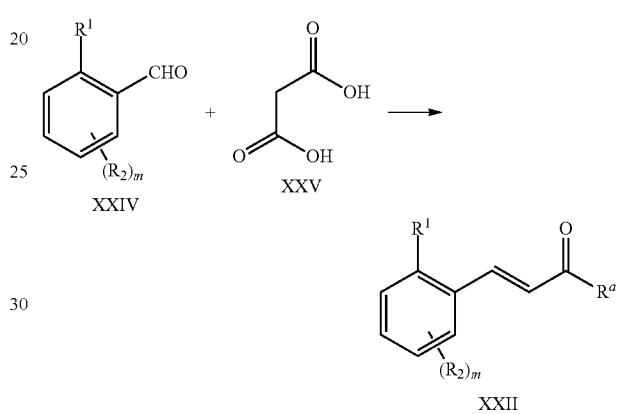

Cinnamic esters of Formula XXII, wherein $R^a$ is lower alkoxy, can be prepared by reaction of bromo or iodobenzenes of Formula XXVI, wherein X=Br or I respectively, with acrylate esters of Formula XXVII, wherein $R^a$ is lower alkoxy, in the presence of a palladium catalyst under Heck reaction conditions.

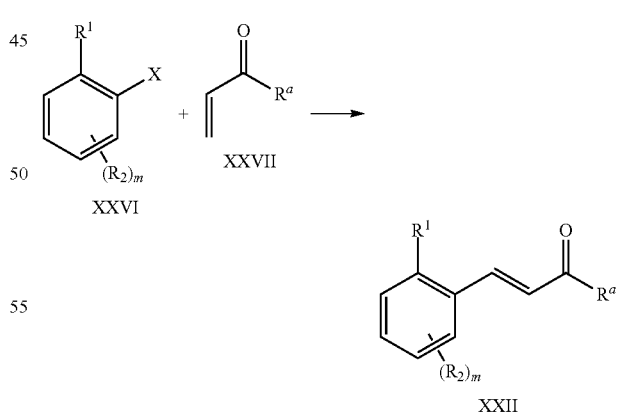

Many spirocyclic amines of Formula XXIII can be prepared by previously described routes or can be purchased.

The following substituted (±)-2-(2,3-dihydrospiro[indene-1,4'-piperidine]-3-yl)acetic acid were purchased from WuXi Pharmatech (Shanghai, China) as their N-Boc or ethyl ester derivatives:

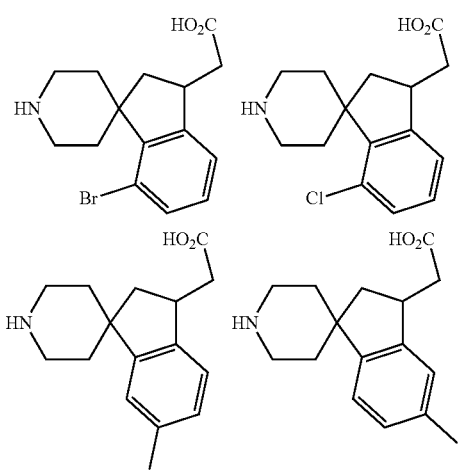

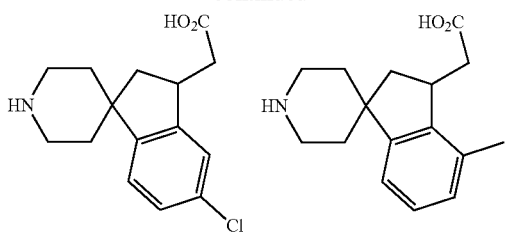

The two enantiomers of tert-butyl 7-bromo-3-(2-ethoxy-2-oxoethyl)-2,3-dihydrospiro[indene-1,4'-piperidine]-1'-carboxylate were also obtained from WuXi Pharmatech (Shanghai, China).

(±)-2-(2,3-Dihydrospiro[indene-1,4'-piperidine]-3-yl)acetic acid can be prepared by deprotection of 2-(1'-(tert-butoxycarbonyl)-2,3-dihydrospiro[indene-1,4'-piperidine]-3-yl)acetic acid as disclosed in Example 98 (Steps A and B) of U.S. Pat. No. 5,578,593, which is hereby incorporated by reference. It, and the following substituted analogs, can also be purchased from WuXi Pharmatech (Shanghai, China).

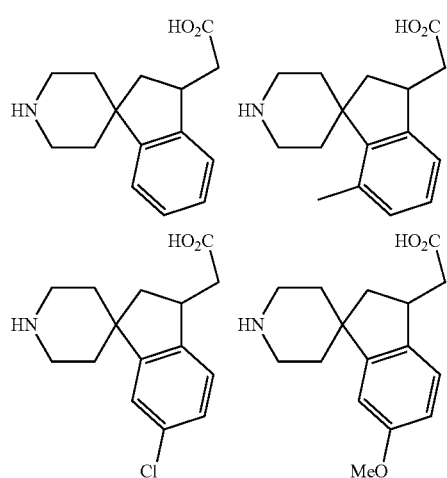

tert-Butyl 7-bromo-3-oxo-2,3-dihydrospiro[indene-1,4'-piperidine]-1'-carboxylate was purchased from WuXi Pharmatech (Shanghai, China):

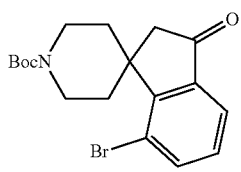

tert-Butyl 1H-spiro[isoquinoline-4,4'-piperidine]-2(3H)-carboxylate was purchased from WuXi Pharmatech (Shanghai, China):

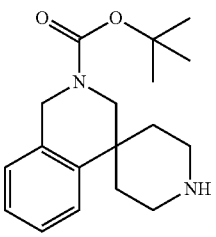 [SMILES: CC(C)(C)OC(=O)N1Cc2ccccc2C2(CCNCC2)C1]

6-Methoxy-3,4-dihydro-2H-spiro[isoquinoline-1,4'-piperidine] was prepared as disclosed in Procedure A in U.S. Pat. No. 7,109,207 (Column 25, Line 5), which is hereby incorporated by reference.

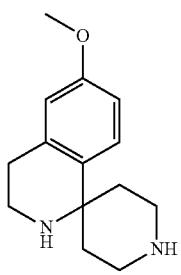 [SMILES: COc1ccc2c(c1)CCNC21CCNCC1]

1'-(tert-butoxycarbonyl)-1,2-dihydrospiro[indole-3,4'-piperidine]-5-carboxylic acid was purchased from WuXi Pharmatech (Shanghai, China).

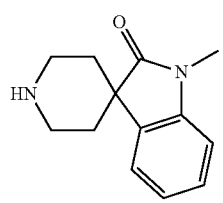 [SMILES: CN1C(=O)C2(CCNCC2)c2ccccc21]

1'-tert-butyl 5-methyl 2-oxospiro[indoline-3,4'-piperidine]-1',5-dicarboxylate was purchased from WuXi Pharmatech (Shanghai, China).

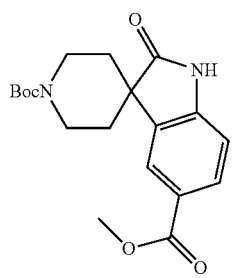 [SMILES: COC(=O)c1ccc2c(c1)C1(CCN(C(=O)OC(C)(C)C)CC1)C(=O)N2]

tert-Butyl 5-fluoro-2-oxospiro[indoline-3,4'-piperidine]-1'-carboxylate was prepared as disclosed in U.S. Pat. No. 7,279,486 Example 6 Step 1), which is hereby incorporated by reference.

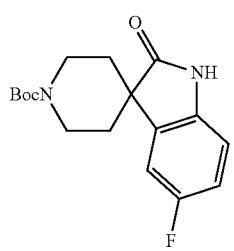 [SMILES: CC(C)(C)OC(=O)N1CCC2(CC1)C(=O)Nc1ccc(F)cc12]

tert-Butyl spiro[indoline-3,4'-piperidine]-1-carboxylate (Formula XXII wherein K, L, Y=C; X=N; $R^1$, K, L and $R^2$ form a fused benzene ring; n=0; s=1; t=2; $R^4$=$CO_2$t-Bu; $R^5$=H; $R^3$ absent; single bonds from L to X and X to Y):

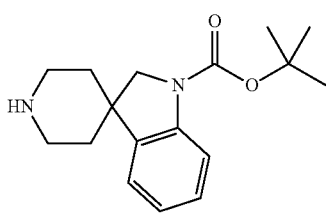 [SMILES: CC(C)(C)OC(=O)N1CC2(CCNCC2)c2ccccc21]

can be prepared from benzyl spiro[indoline-3,4'-piperidine]-1'-carboxylate as disclosed in Example 21 of U.S. Pat. No. 7,045,527, which is hereby incorporated by reference.

The following substituted tert-butyl spiro[indoline-3,4'-piperidine]-1-carboxylate can be purchased from WuXi Pharmatech (Shanghai, China):

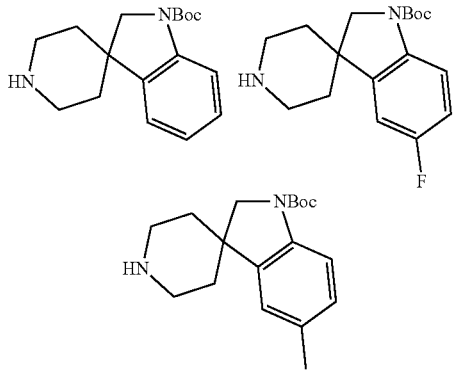

2,3-Dihydrospiro[indene-1,4'-piperidine] can be prepared from indene using the procedures disclosed by Chambers, M. S., et al., *J. Med. Chem.* 1992, 35, 2033-2039, Scheme II, and can be purchased from WuXi Pharmatech (Shanghai, China).

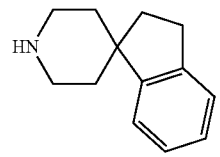

(±)-2,3-Dihydrospiro[indene-1,4'-piperidine]-3-carboxylic acid can be prepared by deprotection of 1'-(tert-butoxycarbonyl)-2,3-dihydrospiro[indene-1,4'-piperidine]-3-carboxylic acid which can be prepared from tert-butyl 3-oxo-2,3-dihydrospiro[indene-1,4'-piperidine]-1'-carboxylate as disclosed in Example 1 (Steps A-D) of U.S. Pat. No. 5,965,565, which is hereby incorporated by reference. This compound was purchased from WuXi Pharmatech (Shanghai, China).

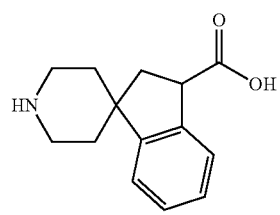 [SMILES: O=C(O)C1CC2(CCNCC2)c2ccccc21]

3H-spiro[isobenzofuran-1,4'-piperidine] can be prepared as described in Cheng, C. Y., et al., *Tetrahedron* 1996, 52, 10935. 3H-spiro[isobenzofuran-1,4'-piperidine] can also be purchased from J & W PharmLab LLC (Morrisville, Pa., USA).

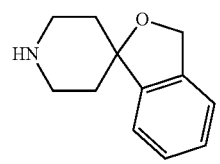

2H-spiro[benzofuran-3,4'-piperidine] can be prepared as described in Parham, W. E., et al., *J. Org. Chem.* 1976, 41, 2628.

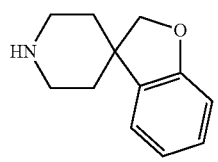 [SMILES: c1ccc2c(c1)OCC21CCNCC1]

3,4-dihydro-2H-spiro[naphthalene-1,4'-piperidine] can be purchased from WuXi Pharmatech (Shanghai, China):

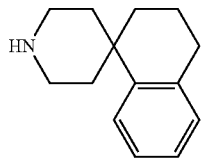 [SMILES: c1ccc2c(c1)CCCC21CCNCC1]

Spiro[benzo[d][1,3]oxazine-4,4'-piperidin]-2(1H)-one can be prepared as described in Clark, R. D. et al *J. Med. Chem.* 1983, 26, 657, which is hereby incorporated by reference.

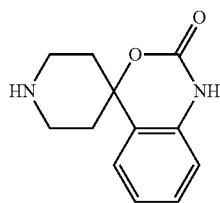 [SMILES: O=C1Nc2ccccc2C2(CCNCC2)O1]

1'H-spiro[piperidine-4,4'-quinazolin]-2'(3'H)-one can be prepared as described in US Patent application 2005/215576 pages 19 and 20, which is hereby incorporated by reference.

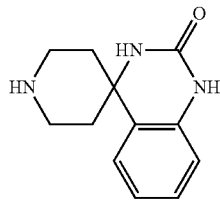 [SMILES: O=C1Nc2ccccc2C2(CCNCC2)N1]

Spiro[piperidine-4,3'-pyrrolo[2,3-b]pyridin]-2'(1'H)-one can be prepared as described in WO 2006/041830 pp 53-55, which is hereby incorporated by reference.

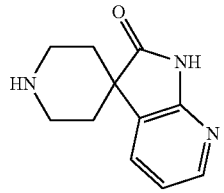 [SMILES: O=C1Nc2ncccc2C12CCNCC2]

In a second process, a compound of Formula I can be prepared from another compound of Formula I. For example:
(1) A compound of Formula I, wherein $R^2$ is bromine or iodine, can be converted to a compound of Formula I wherein $R^2$ is cyano by reaction with Cu(I)CN or with $Zn(CN)_2$ in the presence of a palladium catalyst.

(2) A compound of Formula I, wherein $R^2$ is bromine or iodine, can be converted to a compound of Formula I wherein $R^2$ is $(C_1-C_6)$alkoxycarbonyl by reaction with carbon monoxide and a $(C_1-C_6)$alkyl alcohol in the presence of a palladium catalyst.

(3) A compound of Formula I, wherein $R^2$ is $(C_1-C_6)$alkoxycarbonyl, can be converted to a compound of Formula I wherein $R^2$ is $CONH_2$ by reaction with an alkali metal hydroxide to give a compound of Formula I, wherein $R^2$ is $CO_2H$, followed by coupling with ammonia using EDC in the presence of HOBt.

(4) A compound of Formula I, wherein $R^2$ is $(C_1-C_6)$alkoxycarbonyl, can be converted to a compound of Formula I wherein $R^2$ is $CH_2OH$ by treatment with a reducing agent such as $LiBH_4$.

(5) A compound of Formula I, wherein $R^2$ is $(C_1-C_6)$alkoxycarbonyl, can be converted to a compound of Formula I wherein $R^2$ is $C(Me_2)OH$ by reaction with at least 2 equivalents of methylmagnesium halide or methyl lithium.

(6) A compound of Formula I wherein K is C=O, L is NH and M is a single bond can be converted to a compound of Formula I, wherein K is C=O, L is $NR^4$, M is a single bond and $R^4$ is $(C_1-C_6)$alkyl, by treatment with a base such as NaH and a $(C_1-C_6)$alkyl halide in a solvent such as THF or DMF.

(7) A compound of Formula I, wherein $R^{4a}$ is $CH_2CO_2H$, can be converted to a compound of Formula I, wherein $R^{4a}$ is $CH_2CONHMe$ or $CH_2CONMe_2$, by reaction with methylamine or dimethylamine respectively and a peptide coupling reagent such as EDC, DIC or HATU.

(8) A compound of Formula I, wherein $R^{4a}$ is $CO_2H$ or $CH_2CO_2H$, can be reduced to a compound of Formula I, wherein $R^{4a}$ is $CH_2OH$ or $CH_2CH_2OH$ by reduction with borane in THF.

(9) A compound of Formula I, wherein $R^{4a}$ is $CO_2Me$ or $CH_2CO_2Me$, can be converted to a compound of Formula I, wherein $R^{4a}$ is $CMe_2OH$ or $CH_2CMe_2OH$, by reaction with at least 2 equivalents of methylmagnesium halide or methyllithium.

(10) A compound of Formula I, wherein $R^{4a}$ is OH, can be converted to a compound of Formula I, wherein $R^{4a}$ is chloride, by reaction with thionyl chloride, followed by treatment with a cyclic amine such N-methylpiperazine or morpholine, to give a compound of Formula I, wherein $R^{4a}$ is 1-methyl-4-piperazino or 4-morpholino.

(11) A compound of Formula I, wherein $R^{4a}$ is $NH_2$ can be converted to a compound of Formula I wherein $R^{4a}$ is $NMe_2$ by treatment with formaldehyde and formic acid under Eschweiler-Clark conditions.

(12) A compound of Formula I, wherein $R^{4a}$ is OH can be converted to a compound of Formula I, wherein $R^{4a}$ is

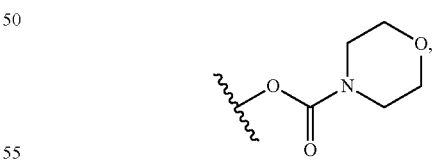

by reaction with carbonyl diimidazole followed by morpholine.

(13) A compound of Formula I, wherein K is $CH_2$, L is CO and M is a single bond, can be converted to a compound of Formula I, wherein K is $CH_2$, L is $CR^{4a}R^{4b}$, M is a single bond, $R^{4a}$ is OH and $R^{4b}$ is Me, by reaction with methylmagnesium halide or methyllithium.

(14) A compound of Formula I, wherein $R^{4a}$ is $CO_2H$ or $CH_2CO_2H$, can be converted to a compound of Formula I, wherein $R^{4a}$ is C(=O)$NHSO_2Me$ or $CH_2C$(=O)$NHSO_3Me$ by treatment with methanesulfonamide and EDC.

(15) A compound of Formula I, wherein $R^{4a}$ is $CH_2CO_2H$, can be converted to a compound of Formula I, wherein $R^{4a}$ is $CH_2NH_2$ by treatment with diphenylphosphoryl azide followed by water.

(16) A compound of Formula I, wherein $R^{4a}$ is $CH_2NH_2$ can be converted to a compound of Formula I wherein $R^{4a}$ is $CH_2NMe_2$ by treatment with formaldehyde and formic acid under Eschweiler-Clark conditions.

(17) A compound of Formula I, wherein $R^{4a}$ is OH can be converted to a compound of Formula I, wherein $R^{4a}$ is $OC(=O)NMe_2$, by reaction with carbonyl diimidazole followed by dimethylamine.

(18) A compound of Formula I, wherein $R^{4a}$ is OH can be converted to a compound of Formula I, wherein $R^{4a}$ is $OC(=O)NHSO_2Me$, by reaction with carbonyl diimidazole followed by methanesulfonamide.

(19) A compound of Formula I, wherein $R^{4a}$ is $CH_2NH_2$ can be converted to a compound of Formula I, wherein $R^{4a}$ is $CH_2NHMe$, by sequential reaction with (i) di-tert-butyldicarbonate (ii) NaH, MeI and (iii) TFA, $CH_2Cl_2$.

(20) A compound of Formula I, wherein $R^{4a}$ is OH can be converted to a compound of Formula I, wherein $R^{4a}$ is

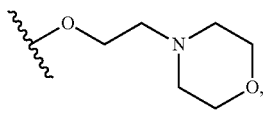 [SMILES: *OCCN1CCOCC1]

by reaction with NaH and 4-(2-chloroethyl)morpholine.

(21) A compound of Formula I, wherein $R^{4a}$ is $CH_2CO_2H$ can be converted to a compound of Formula I, wherein $R^{4a}$ is

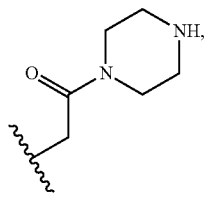 [SMILES: *CC(=O)N1CCNCC1]

by sequential reaction with (i) tert-butyl piperazine-1-carboxylate in the presence of EDC or HATU and 4-(2-chloroethyl)morpholine and (ii) TFA in $CH_2Cl_2$.

(22) A compound of Formula I, wherein $R^{4a}$ is OH can be converted to a compound of Formula I, wherein $R^{4a}$ is

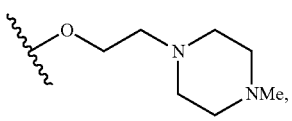 [SMILES: *OCCN1CCN(C)CC1]

by reaction with NaH and 1-(2-chloroethyl)-4-methylpiperazine.

(23) A compound of Formula I, wherein K is $CH_2$, L is CO and M is a single bond, can be converted to a compound of Formula I, wherein K is $CH_2$, L is CO and M is NH, by treatment with hydroxylamine to give a compound of Formula I, wherein K is $CH_2$, L is C=NOH and M is a single bond, followed by treatment with a strong acid under Beckmann rearrangement conditions.

(24) A compound of Formula I, wherein X is $CR^5$ and $R^5$ is Br or I, can be converted to a compound of Formula I wherein X is $CR^5$ and $R^5$ is $(C_1-C_6)$alkoxycarbonyl by reaction with carbon monoxide and a $(C_1-C_6)$alkyl alcohol in the presence of a palladium catalyst.

(25) A compound of Formula I, wherein X is $CR^5$ and $R^5$ is $(C_1-C_6)$alkoxycarbonyl-C, can be converted to a compound of Formula I wherein X is $CR^5$ and $R^5$ is $CONH_2$ by reaction with an alkali metal hydroxide to give a compound of Formula I, wherein X is $CR^5$ and $R^5$ is $CO_2H$, followed by coupling with ammonia using EDC in the presence of HOBt.

(26) A compound of Formula I, wherein X is $CR^5$ and $R^5$ is $(C_1-C_6)$alkoxycarbonyl, can be converted to a compound of Formula I wherein X is $CR^5$ and $R^5$ is $CH_2OH$ by treatment with a reducing agent such as $LiBH_4$.

(27) A compound of Formula I, wherein X is $CR^5$ and $R^5$ is $(C_1-C_6)$alkoxycarbonyl, can be converted to a compound of Formula I wherein X is $CR^5$ and $R^5$ is $C(Me_2)OH$ by reaction with at least 2 equivalents of methylmagnesium halide or methyl lithium.

LC-MS Methods

Method 1 [LC-MS (3 min)]
Column: Chromolith SpeedRod, RP-18e, 50×4.6 mm; Mobil phase: A: 0.01% TFA/water, B: 0.01% $TFA/CH_3CN$; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

Method 2 (10-80)

| Column | YMC-PACK ODS-AQ, 50 × 2.0 mm 5 μm | | |
|---|---|---|---|
| Mobile Phase | A: water (4 L) + TFA (1.5 mL)) | | |
| | B: acetonitrile (4 L) + TFA (0.75 mL)) | | |
| | TIME (min) | A % | B % |
| | 0 | 90 | 10 |
| | 2.2 | 20 | 80 |
| | 2.5 | 20 | 80 |
| Flow Rate | 1 mL/min | | |
| Wavelength | UV 220 nm | | |
| Oven Temp | 50° C. | | |
| MS ionization | ESI | | |

Method 3 (30-90)

| Column | YMC-PACK ODS-AQ, 50 × 2.0 mm 5 μm | | |
|---|---|---|---|
| Mobile Phase | A: water (4 L) + TFA (1.5 mL)) | | |
| | B: acetonitrile (4 L) + TFA (0.75 mL)) | | |
| | TIME (min) | A % | B % |
| | 0 | 70 | 30 |
| | 2.2 | 10 | 90 |
| | 2.5 | 10 | 90 |
| Flow Rate | 1 mL/min | | |
| Wavelength | UV220 | | |
| Oven Temp | 50° C. | | |
| MS ionization | ESI | | |

Intermediate Preparations

Preparation 1

7-bromospiro[isoindoline-1,4'-piperidin]-3-one

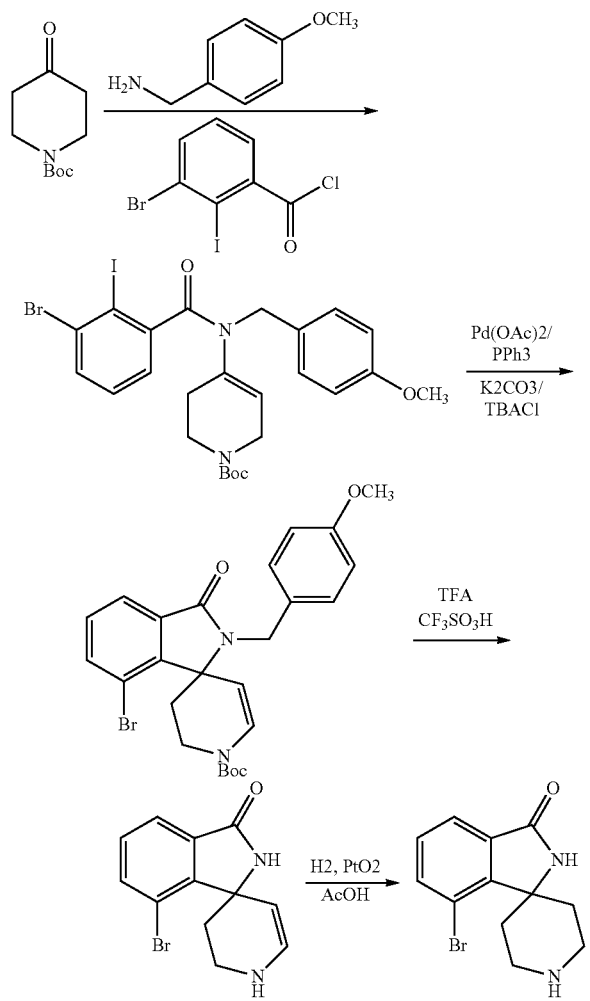

Step 1

A mixture of tert-butyl-4-oxopiperidine-1-carboxylate (19 g, 0.0.096 mol), 4-methoxybenzylamine (13 g, 0.096 mol) and toluene was stirred at 100° C. for 3 h and then concentrated to give a residue. Toluene (300 mL), 3-bromo-2-iodobenzoyl chloride (25 g, 0.077 mol), and $Et_3N$ (24.5 g, 0.23 mol) were added to the residue and the mixture was stirred at 80° C. overnight. The mixture was cooled, and poured into water and extracted with EtOAc. The organic layer was dried and concentrated to give the crude product which was purified by column chromatography to afford tert-butyl 4-(3-bromo-2-iodo-N-(4-methoxybenzyl)benzamido)-5,6-dihydropyridine-1(2H)-carboxylate (30 g, 63%). $^1$H NMR: (400 MHz, MeOD): δ=1.38 (s, 9H), 1.43 (m, 2H), 1.48 (m, 4H), 1.63 (m, 2H), 3.18 (m, 2H), 3.60 (m, 2H), 3.80 (s, 3H), 4.55 (d, 1H), 5.49 (m, 1H), 6.88 (m, 3H), 7.02 (m, 2H), 7.16 (m, 1H), 7.32 (m, 3H), 7.55 (m, 1H).

Step 2

A solution of tert-butyl 4-(3-bromo-2-iodo-N-(4-methoxybenzyl)benzamido)-5,6-dihydropyridine-1(2H)-carboxylate (30 g, 0.048 mol) in $CH_3CN$ (500 mL) was stirred for 0.5 h under nitrogen. $K_2CO_3$ (13 g, 0.096 mol), $PPh_3$ (6 g, 20%), tetra-butylammonium chloride (15 g, 0.048 mol) and $Pd(OAc)_2$ (3 g, 0.0048 mol) were added. The resulting mixture was heated to reflux for 12 h. The mixture was poured into water and extracted with EtOAc. The organic layer was dried and concentrated to give the crude product which was purified by column chromatography to afford tert-butyl 7-bromo-2-(4-methoxybenzyl)-3-oxo-2',3'-dihydro-1'H-spiro[isoindoline-1,4'-pyridine]-1'-carboxylate (12 g, 50%). $^1$H NMR: (400 MHz, $CDCl_3$): δ=1.51 (s, 9H), 1.73 (m, 2H), 2.83-3.08 (m, 2H), 3.79 (s, 3H), 4.00 (m, 1H), 4.30 (m, 1H), 4.42 (d, 1H), 5.02 (d, 1H), 6.83 (d, 2H), 7.201 (d, 2H), 7.45 (m, 1H), 7.70 (d, 1H), 7.88 (d, 1H).

Step 3

A solution of tert-butyl 7-bromo-2-(4-methoxybenzyl)-3-oxo-2',3'-dihydro-1'H-spiro[isoindoline-1,4'-pyridine]-1'-carboxylate (5 g, 0.01 mol) in TFA (50 mL) and $CF_3SO_3H$ (5 mL) was stirred and heated for 8 h. The mixture was concentrated to give a residue which was washed with aq NaOH and extracted with EtOAc. The organic layer was dried and concentrated to give 7-bromo-2',3'-dihydro-1'H-spiro[isoindoline-1,4'-pyridin]-3-one (2.0 g, 72%).

Step 4

A solution of 7-bromo-2',3'-dihydro-1'H-spiro[isoindoline-1,4'-pyridin]-3-one (2 g, 0.0072 mol) in $CH_3COOH$ was hydrogenated in the presence of $PtO_2$ for 1.5 h. The catalyst was removed by filtration and the filtrate was concentrated to give the crude product which was washed with saturated aq $Na_2CO_3$. The solvent was removed to give the 7-bromospiro[isoindoline-1,4'-piperidin]-3-one (2 g, 100%).

2-methylspiro[isoindoline-1,4'-piperidin]-3-one was prepared following procedures analogous to those described above using methylamine and 2-iodobenzoyl chloride in Step 1 and omitting Step 3.

7-chloro-2-methylspiro[isoindoline-1,4'-piperidin]-3-one was prepared following procedures analogous to those described above using methylamine and 3-chloro-2-iodobenzoyl chloride in Step 1 and omitting Step 3.

7-chlorospiro[isoindoline-1,4'-piperidin]-3-one was prepared following procedures analogous to those described above using 3-chloro-2-iodobenzoyl chloride in Step 1.

Preparation 2

3,5-dichloro-2-iodobenzoyl chloride

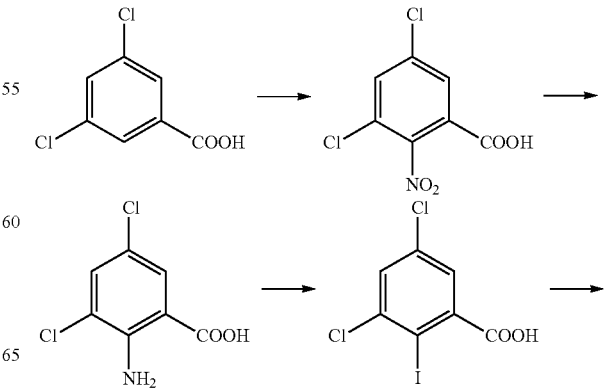

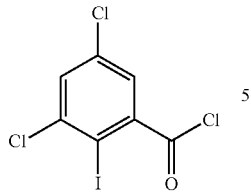

Step 1

To a solution of 3,5-dichloro-benzoic acid (25 g, 0.13 mol) in 125 mL of concentrated $H_2SO_4$ at 0° C. was added $HNO_3$ (68%) dropwise. The mixture was stirred at 0° C. and allowed to warm to rt overnight. The mixture was poured into ice-water. The suspension was then filtered and the solid was washed with cold water and dried to give the crude product (30 g, 98%). $^1H$ NMR ($d_6$-DMSO): 8.01 (s, 1H), 8.28 (s, 1H).

Step 2

$H_2$ was sent to a solution of 3,5-dichloro-2-nitrobenzoic acid (20 g, 0.085 mol), Re—Ni (2.0 g) in MeOH (400 mL). The mixture was stirred at rt overnight. The mixture was filtered and concentrated to give the crude product (17 g, 98%). $^1H$ NMR ($d_6$-DMSO): 7.27 (s, 2H), 7.66 (m, 2H).

Step 3

A solution of 2-amino-3,5-dichloro-benzoic acid (17 g, 0.083 mol), $NaNO_2$ (6.29 g, 0.09 mol) and NaOH (5 M, 17 mL) in 150 mL of water was added slowly to a stirred and cooled solution of HCl (36%, 31 mL) in 120 mL of water (0-5° C.). The formed solution was stirred at that temperature for 30 min, and then added to a solution of KI (21 g, 0.125 mol) and $H_2SO_4$ (98%, 7 mL) in 40 mL of water. The mixture was slowly heated to 50° C. for 30 min, which was then raised to 100° C. to remove iodine. After 2 h, the mixture was cooled, treated with $Na_2S_2O_4$ (1.2 g, 0.006 mol) and allowed to stand overnight. The mixture was filtered and the solid was washed with cooled water, dried to give the crude product (21.5 g, 82%). $^1H$ NMR ($d_6$-DMSO): 7.53 (s, 1H), 7.82 (m, 1H).

Step 4

A mixture of 3,5-dichloro-2-iodo-benzoic acid (9.0 g, 28 mmol) and $SOCl_2$ (100 mL) was heated to reflux overnight. The solvent was removed to give crude 3,5-dichloro-2-iodo-benzoyl chloride (9.4 g, 98%). $^1H$ NMR ($CDCl_3$): 7.64 (m, 2H).

Preparation 3

5,7-dichlorospiro[isoindoline-1,4'-piperidin]-3-one

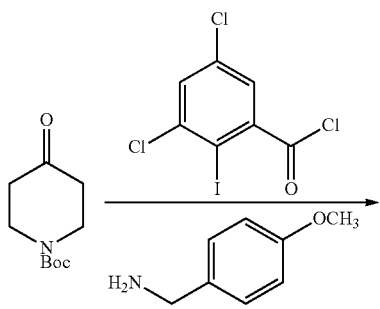

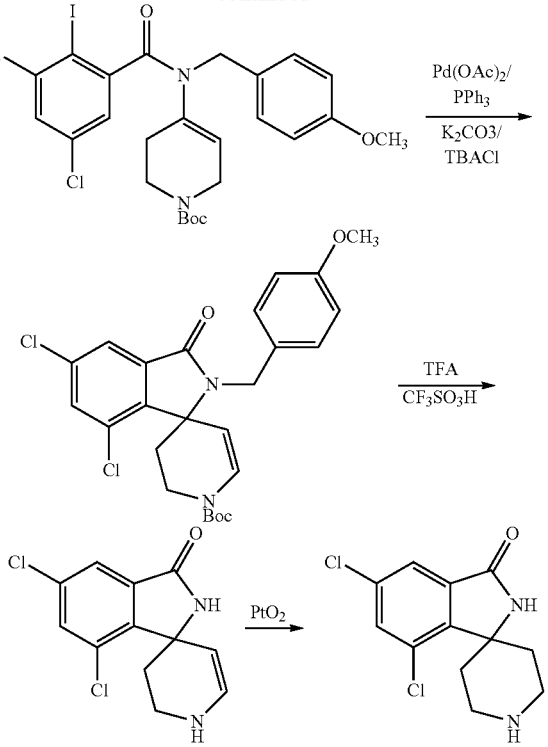

Step 1

A 500-mL flask was charged with 4-oxo-piperidine-1-carboxylic acid tert-butyl ester (7.0 g, 35 mmol), 4-methoxybenzylamine (4.8 g, 35 mmol) and 120 mL of toluene. The mixture was heated to reflux for 12 h. The yellow-orange solution was allowed to cool to ambient and then evaporated. The residue was used directly in the next step without further purification. It was dissolved in 150 mL of toluene. Then 3,5-dichloro-2-iodobenzoyl chloride (9.4 g, 28 mmol) and $Et_3N$ (4.5 g, 44 mmol) was added. The mixture was heated to reflux overnight. The mixture was acidified with 0.5 N aq HCl, and the layers were separated. The organic layer was washed with brine, dried and concentrated to give the crude product. It was purified by column chromatography (PE: EtOAc=15:1) to give the desired product (9.0 g, 42%).

Step 2

4-[(3,5-Dichloro-2-iodo-benzoyl)-(4-methoxy-benzyl)-amino]-3,6-dihydro-2H-pyridine-1-carboxylic acid tert-butyl ester (9.0 g, 15 mmol) was dissolved in 100 mL of acetonitrile in a three flask fitted with a condenser and the mixture was sparged with $N_2$ for 1 h. The flask was quickly opened and $Pd(OAc)_2$ (336 mg, 1.5 mmol), $PPh_3$ (786 mg, 3.0 mmol), $K_2CO_3$ (4.14 g, 30 mmol) and $^nBu_4NBr$ (4.82 g, 15 mmol) was added. The mixture was heated to reflux overnight. After this time, the iodide was consumed and the mixture was cooled to rt and evaporated. The residue was taken up with $EtOAc/H_2O$ and the layers were separated. The organic layer was washed with brine, dried and concentrated to give the crude product. It was purified by column chromatography (PE:EtOAc=10:1) to give tert-butyl 5,7-dichloro-2-(4-methoxybenzyl)-3-oxo-2',3'-dihydro-1'H-spiro[isoindoline-1,4'-pyridine]-1'-carboxylate (3.5 g, 48%). $^1H$ NMR ($CDCl_3$): 1.52 (s, 9H), 1.63 (s, 1H), 1.78 (m, 1H), 2.71 (m, 1H), 3.04 (m, 1H), 3.78 (s, 3H), 3.97 (m, 1H), 4.25 (m, 1H), 4.46 (m, 1H), 5.02 (m, 1H), 6.82 (m, 2H), 7.18 (m, 2H), 7.52 (s, 1H), 7.81 (s, 1H).

Step 3 tert-Butyl 5,7-dichloro-2-(4-methoxybenzyl)-3-oxo-2',3'-dihydro-1'H-spiro[isoindoline-1,4'-pyridine]-1'-carboxylate (3.5 g, 7.2 mmol) in TFA (36 mL) and $CF_3SO_3H$ (4 mL) was heated to 60° C. for 5 h. The solvent was removed and satd aq $NaHCO_3$ was added till pH=7. Then EtOAc was added, the organic layer was washed with brine, dried and concentrated to give the crude product. It was purified by preparative HPLC to give 5,7-dichloro-2',3'-dihydro-1'H-spiro[isoindoline-1,4'-pyridin]-3-one (0.2 g, 10%). $^1H$ NMR ($CDCl_3$): 1.66 (m, 3H), 2.81 (m, 1H), 3.15 (m, 1H), 3.76 (m, 1H), 7.57 (m, 1H), 7.75 (m, 1H).

Step 4

$H_2$ was sent to the solution of 5,7-dichloro-2',3'-dihydro-1'H-spiro[isoindoline-1,4'-pyridin]-3-one (400 mg, 1.5 mmol), $PtO_2$ (40 mg) in acetic acid (10 mL). The mixture was stirred at rt for 2 h. The mixture was filtered, the filtrate was neutralized with satd aq $NaHCO_3$ and extracted with EtOAc (3×). The combined organic layers were washed with brine, dried and concentrated to give 5,7-dichlorospiro[isoindoline-1,4'-piperidin]-3-one (300 mg, 73%). $^1H$ NMR ($CD_3OD$): 1.36 (m, 2H), 2.76 (m, 2H), 2.94 (m, 2H), 3.12 (m, 2H), 7.67 (m, 2H).

Preparation 4

2H-spiro[isoquinoline-1,4'-piperidin]-3(4H)-one

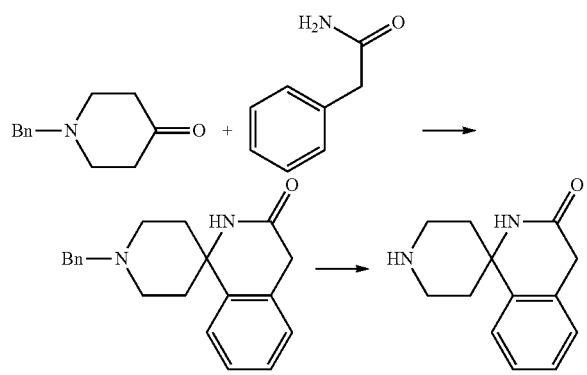

Step 1

A mixture of 1-benzyl-4-piperidone (8.5 g, 45 mmol), phenylacetamide (6.1 g, 45 mmol) and polyphosphoric acid (~100 g) was heated at 100° C. for 2 d. Water (100 mL) was added and the mixture was allowed to cool to rt. The mixture was diluted and made strongly basic by addition of NaOH pellets and water (900 mL). The mixture was extracted with $CH_2Cl_2$ (3×200 mL). The combined organic extracts were washed with brine and concentrated to leave a red solid (14.16 g). Three recrystallization from i-PrOH (40 mL) afforded 1'-benzyl-2H-spiro[isoquinoline-1,4'-piperidin]-3(4H)-one (2.79 g, 20%) as a white solid. LC-MS Method 1 $t_R$=0.92 min, m/z=307.

Step 2

A solution of 1'-benzyl-2H-spiro[isoquinoline-1,4'-piperidin]-3(4H)-one (2.79 g, 9.1 mmol) in 4:1 EtOAc/HOAc (100 mL) was added to 10% Pd on C. The mixture was shaken under 50 psi of $H_2$ at rt for 3 h. The mixture was filtered through Celite and the filtrate was concentrated to give a white solid (2.60 g). This material was dissolved in MeOH (80 mL) and $CH_2Cl_2$ (80 mL). Amberlyst A26 $OH^-$ (12 g) was added. The mixture was stirred for 0.5 h and filtered. The filtrate was concentrated to afford 2H-spiro[isoquinoline-1,4'-piperidin]-3(4H)-one (1.59 g, 80%) as a white solid. LC-MS Method 1 $t_R$=0.58 min, m/z=217.

Preparation 5

1,1-dimethyl-1H-spiro[isoquinoline-4,4'-piperidin]-3(2H)-one

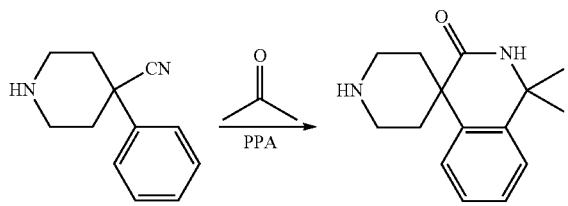

Polyphosphoric acid (10 g) was heated to 140° C. and 4-cyano-4-phenylpiperidine (1.00 g, 5.4 mmol) was added. The mixture was stirred for 2 min under a reflux condenser and acetone (2 mL, 27 mmol) was added through the condenser. The mixture was stirred at 140° C. for 1 h and poured onto crushed ice. After the ice had melted, the mixture was basified by addition of solid $K_2CO_3$. The mixture was extracted with $CH_2Cl_2$ (2×100 mL). The combined $CH_2Cl_2$ extracts were washed with brine, dried over $Na_2SO_4$ and concentrated to afford an amber oil (1.19 g). This material was dissolved in 5% aq HCl (50 mL) and washed with ether (2×50 mL). The aq HCl layer was basified with solid $K_2CO_3$ and extracted with $CH_2Cl_2$ (2×50 mL). These $CH_2Cl_2$ extracts were dried over $Na_2SO_4$ and concentrated to furnish crude 1,1-dimethyl-1H-spiro[isoquinoline-4,4'-piperidin]-3(2H)-one (0.32 g, 24%) as a brown oil. LC-MS Method 1 $t_R$=0.40 min, m/z=245.

Example 1

(±)-(E)-ethyl 2-(7-bromo-1'-(3-(2-(trifluoromethyl)phenyl)acryloyl)-2,3-dihydrospiro[indene-1,4'-piperidine]-3-yl)acetate

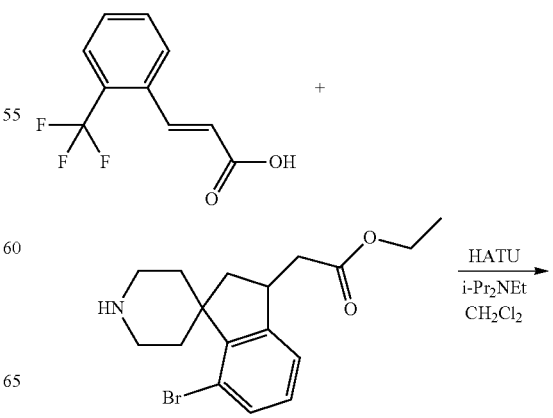

-continued

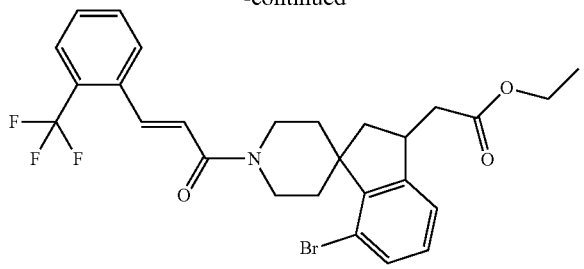

A solution of (±)-ethyl 2-(7-bromo-2,3-dihydrospiro[indene-1,4'-piperidine]-3-yl)acetate TFA salt (31 mg, 0.07 mmol) in CH$_2$Cl$_2$ was treated with MP-carbonate resin (2.89 mmol g$^{-1}$, 200 mg, 0.58 mmol). The mixture was stirred for 0.5 h and filtered. To the filtrate were added ortho-(trifluoromethyl)cinnamic acid (42 mg, 0.19 mmol), i-Pr$_2$NEt (0.07 mL, 0.39 mmol) and solid HATU (37 mg, 0.10 mmol). The mixture was stirred at rt for 4 h. A 10-mL Chem-Elut cartridge was wetted with 5% aq HCl (6 mL) and allowed to stand for 5 min. The reaction mixture was applied and the cartridge was eluted with ether (20 mL). The eluate was passed through a second 10-mL Chem-Elut cartridge that had been prewetted with satd aq NaHCO$_3$ (6 mL). The eluate was evaporated and the residue was purified by preparative HPLC to afford (±)-(E)-ethyl 2-(7-bromo-1'-(3-(2-(trifluoromethyl)phenyl)acryloyl)-2,3-dihydrospiro[indene-1,4'-piperidine]-3-yl)acetate (15 mg, 42%) as an oil. LC-MS Method 1 t$_R$=2.23, min, m/z=550, 552; $^1$H NMR (CDCl$_3$) 1.28 (t, 3H), 1.40-1.80 (3H), 2.43 (m, 2H), 2.76 (m, 1H), 2.91 (m, 2H), 3.18 (m, 1H), 3.34 (m, 1H), 3.62 (m, 1H), 4.14 (m, 1H), 4.19 (q, 2H), 4.80 (m, 1H), 6.83 (d, 1H), 7.11 (m, 2H), 7.35-7.75 (5H), 7.92 (m, 1H).

Example 2

(±)-(E)-2-(7-bromo-1'-(3-(2-(trifluoromethyl)phenyl)acryloyl)-2,3-dihydrospiro[indene-1,4'-piperidine]-3-yl)acetic acid

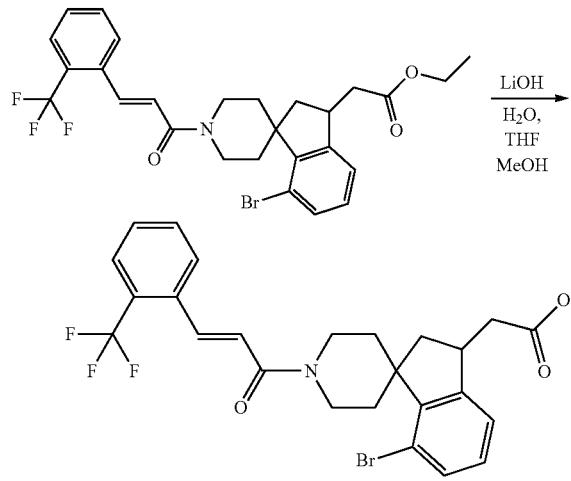

(±)-(E)-ethyl 2-(7-bromo-1'-(3-(2-(trifluoromethyl)phenyl)acryloyl)-2,3-dihydrospiro[indene-1,4'-piperidine]-3-yl)acetate (13 mg, mmol) was dissolved in THF (0.4 mL) and MeOH (0.8 mL). A solution of LiOH.H$_2$O (10 mg) in water (0.4 mL) was added. The mixture was stirred at rt for 5 d. The reaction mixture was submitted directly to preparative HPLC to afford (±)-(E)-2-(7-bromo-1'-(3-(2-(trifluoromethyl)phenyl)acryloyl)-2,3-dihydrospiro[indene-1,4'-piperidine]-3-yl) acetic acid (6 mg, %) as a solid. LC-MS Method 1 t$_R$=1.92, min, m/z=522, 524.

Example 2 Isomer 1

(±)-(E)-2-(7-bromo-1'-(3-(2-(trifluoromethyl)phenyl) acryloyl)-2,3-dihydrospiro[indene-1,4'-piperidine]-3-yl)acetic acid isomer 1

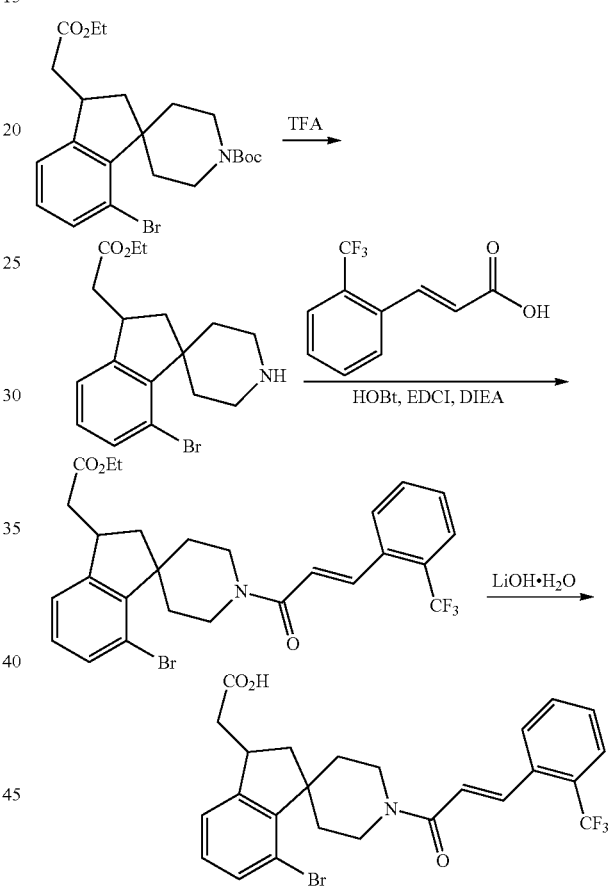

Step 1

To a solution of tert-butyl 7-bromo-3-(2-ethoxy-2-oxoethyl)-2,3-dihydrospiro[indene-1,4'-piperidine]-1'-carboxylate isomer 1 (200 mg, 0.44 mmol) in anhydrous CH$_2$Cl$_2$ (2 mL) was added 20% TFA in CH$_2$Cl$_2$ (10 mL) at 0° C. The reaction mixture was stirred at rt for 1 h. The reaction mixture was concentrated to give ethyl 2-(7-bromo-2,3-dihydrospiro [indene-1,4'-piperidine]-3-yl)acetate isomer 1 as its trifluoroacetate salt (156 mg, 100%), which was used to the next step without purification.

Step 2

To a solution of ethyl 2-(7-bromo-2,3-dihydrospiro[indene-1,4'-piperidine]-3-yl)acetate isomer 1 (156 mg, 0.44 mmol) in anhydrous CH$_2$Cl$_2$ (6 mL) was added (E)-3-(2-(trifluoromethyl)phenyl)acrylic acid (96 mg, 0.44 mmol), HOBt (120 mg, 0.89), EDCI (175 mg, 0.89) and i-Pr$_2$NEt (286 mg, 2.22 mol) at 0° C. and then stirred overnight under N₂. Then the reaction mixture was washed with 1 N aq HCl and water. The organic phase was dried over Na₂SO₄, filtered and concentrated to afford a residue, which was purified by TLC to give (E)-ethyl2-(7-bromo-F-(3-(2-(trifluoromethyl)phenyl)acryloyl)-2,3-dihydrospiro[indene-1,4'-piperidine]-3-yl)acetate isomer 1 (172 mg, 71%). ¹H NMR (CD₃OD): 1.25 (m, 3H), 1.47 (m, 2H), 1.50 (s, 1H), 1.71 (m, 1H), 2.48 (m, 2H), 2.74 (m, 1H), 2.90 (m, 2H), 3.15 (m, 1H), 3.33 (m, 1H), 3.61 (m, 1H), 4.10 (m, 1H), 4.19 (m, 2H), 4.79 (m, 1H), 6.82 (m, 1H), 7.05 (m, 2H), 7.42 (m, 2H), 7.53 (m, 1H), 7.68 (m, 2H), 7.95 (m, 1H). 443-071-3

Step 3

To the solution of (E)-ethyl2-(7-bromo-F-(3-(2-(trifluoromethyl)phenyl)acryloyl)-2,3-dihydrospiro[indene-1,4'-piperidine]-3-yl)acetate isomer 1 (172 mg, 0.31 mmol) in methanol (5 mL) was added 2 M aq LiOH.H₂O at rt and the mixture was stirred for 8 h. The reaction mixture was concentrated to remove methanol and extracted with CH₂Cl₂ (2×). The combined organic phases were dried, filtered and concentrated to give (E)-2-(7-bromo-1'-(3-(2-(trifluoromethyl)phenyl)acryloyl)-2,3-dihydrospiro[indene-1,4'-piperidine]-3-yl)acetic acid isomer 1 (106 mg, 65%). ¹H NMR (CD₃OD): 1.58 (m, 2H), 1.82 (m, 1H), 2.48 (m, 2H), 2.74-3.06 (m, 3H), 3.15 (m, 1H), 3.43 (m, 1H), 3.61 (m, 1H), 4.32 (m, 1H), 4.70 (m, 1H), 7.10 (m, 1H), 7.24 (m, 2H), 7.36 (m, 1H), 7.56 (m, 1H), 7.66 (m, 1H), 7.78 (m, 1H), 7.96 (m, 1H).

Example 2 Isomer 2

(E)-2-(7-bromo-1'-(3-(2-(trifluoromethyl)phenyl)acryloyl)-2,3-dihydrospiro[indene-1,4'-piperidine]-3-yl)acetic acid isomer 2

The title compound was prepared following a procedure analogous to that described for Example 2 Isomer 1 using tert-butyl 7-bromo-3-(2-ethoxy-2-oxoethyl)-2,3-dihydrospiro[indene-1,4'-piperidine]-1'-carboxylate isomer 2 in Step 1. ¹H NMR: (400 MHz, CD₃OD): δ=0.84 (m, 1H), 1.18 (m, 2H), 1.46 (m, 2H), 1.73 (m, 1H), 2.41 (m, 2H), 2.74 (m, 1H), 2.85 (m, 1H), 3.08 (m, 1H), 3.31 (m, 1H), 3.57 (m, 1H), 4.26 (m, 1H), 4.63 (m, 1H), 7.05 (m, 1H), 7.17 (m, 2H), 7.33 (m, 1H), 7.48 (m, 1H), 7.60 (m, 1H), 7.69 (m, 1H), 7.89 (m, 2H).

Example 3

(±)-(E)-2-(7-chloro-1'-(3-(2-(trifluoromethyl)phenyl)acryloyl)-2,3-dihydrospiro[indene-1,4'-piperidine]-3-yl)acetic acid

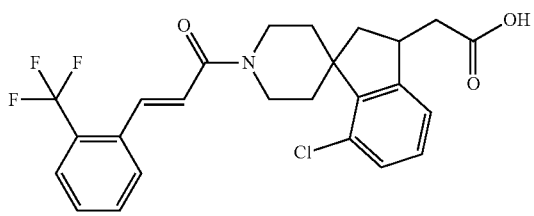 [SMILES: O=C(O)CC1CC2(CCN(C(=O)/C=C/c3ccccc3C(F)(F)F)CC2)c2c(Cl)cccc21]

The title compound was prepared employing a procedure analogous to that described in Example 1 using methyl 2-(7-chloro-2,3-dihydrospiro[indene-1,4'-piperidine]-3-yl)acetate followed by a procedure analogous to that described in Example 2. LC-MS Method 1 t_R=1.9, min, m/z=478, 480; ¹H NMR (CDCl₃) 1.20-1.40 (3H), 1.72 (m, 1H), 2.40 (m, 1H), 2.51 (m, 1H), 2.65-3.40 (5H), 3.62 (m, 1H), 4.10 (d, 1H), 4.78 (d, 1H), 6.84 (d, 1H), 7.05-7.2 (3H), 7.46 (m, 1H), 7.58 (m, 1H), 7.66 (m, 2H), 7.95 (d, 1H).

Example 4

(±)-(E)-2-(7-chloro-1'-(3-(4-fluoro-2-(trifluoromethyl)phenyl)acryloyl)-2,3-dihydrospiro[indene-1,4'-piperidine]-3-yl)acetic acid

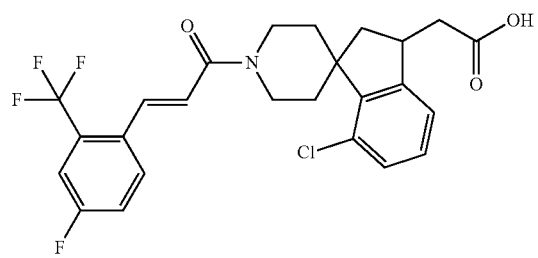 [SMILES: O=C(O)CC1CC2(CCN(C(=O)/C=C/c3ccc(F)cc3C(F)(F)F)CC2)c2c(Cl)cccc21]

The title compound was prepared employing a procedure analogous to that described in Example 1 using methyl 2-(7-chloro-2,3-dihydrospiro[indene-1,4'-piperidine]-3-yl)acetate and 4-fluoro-2-(trifluoromethyl)cinnamic acid followed by a procedure analogous to that described in Example 2. LC-MS Method 1 t_R=1.95, min, m/z=496, 498; ¹H NMR (CDCl₃) 1.20-1.40 (3H), 1.70 (m, 1H), 2.40 (m, 1H), 2.53 (m, 1H), 2.65-3.05 (4H), 3.30 (m, 1H), 3.62 (m, 1H), 4.06 (d, 1H), 4.79 (d, 1H), 6.80 (d, 1H), 7.1-7.5 (5H), 7.68 (m, 1H), 7.85 (d, 1H).

Example 5

(±)-(E)-2-(7-chloro-1'-(3-(5-fluoro-2-(trifluoromethyl)phenyl)acryloyl)-2,3-dihydrospiro[indene-1,4'-piperidine]-3-yl)acetic acid

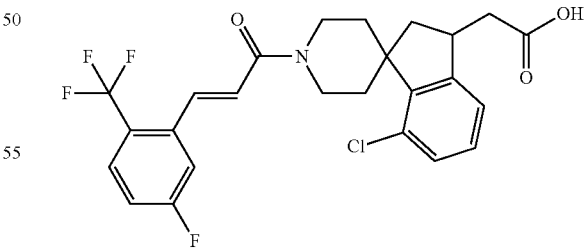

The title compound was prepared employing a procedure analogous to that described in Example 1 using methyl 2-(7-chloro-2,3-dihydrospiro[indene-1,4'-piperidine]-3-yl)acetate and 5-fluoro-2-(trifluoromethyl)cinnamic acid followed by a procedure analogous to that described in Example 2. LC-MS Method 1 t_R=1.93, min, m/z=496, 498; ¹H NMR (CDCl₃) 1.20-1.40 (3H), 1.70 (m, 1H), 2.39 (m, 1H), 2.51 (m, 1H), 2.65-3.05 (4H), 3.36 (m, 1H), 3.62 (br s, 1H), 4.06 (d, 1H), 4.79 (d, 1H), 6.83 (d, 1H), 7.0-7.5 (5H), 7.70 (m, 1H), 7.87 (d, 1H).

Example 6

(±)-(E)-2-(7-chloro-1'-(3-(2-(trifluoromethyl)phenyl)acryloyl)-2,3-dihydrospiro[indene-1,4'-piperidine]-3-yl)acetamide

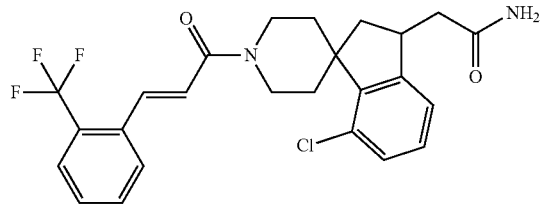 [SMILES: NC(=O)CC1CC2(CCN(C(=O)/C=C/c3ccccc3C(F)(F)F)CC2)c2c(Cl)cccc21]

The title compound was prepared employing a procedure analogous to that described in Example 1 using methyl 2-(7-chloro-2,3-dihydrospiro[indene-1,4'-piperidine]-3-yl)acetate followed by a procedure analogous to that described in Example 2. LC-MS Method 1 $t_R$=1.9, min, m/z=478; $^1$H NMR (CDCl$_3$) 1.38 (d, 1H), 1.42 (d, 1H), 1.51 (m, 1H), 2.38 (m, 2H), 2.7-3.5 (m, 6H), 4.10 (d, 1H), 4.79 (d, 1H), 5.5 (br s, 2H), 6.84 (d, 1H), 7.05-7.20 (3H), 7.43 (m, 1H), 7.57 (m, 1H), 7.68 (m, 2H), 7.94 (d, 1H).

Example 7

(±)-(E)-2-(7-chloro-1'-(3-(2-(trifluoromethyl)phenyl)acryloyl)-2,3-dihydrospiro[indene-1,4'-piperidine]-3-yl)-N-methyl-N-(2-(methylamino)ethyl)acetamide

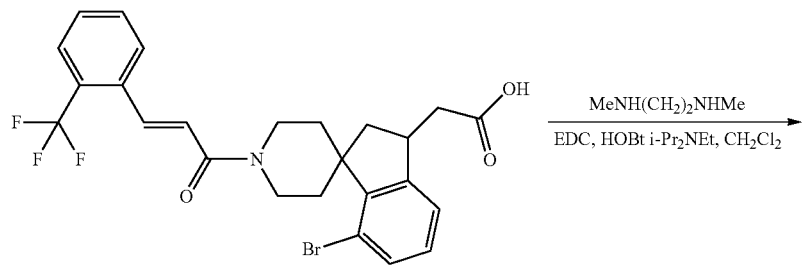

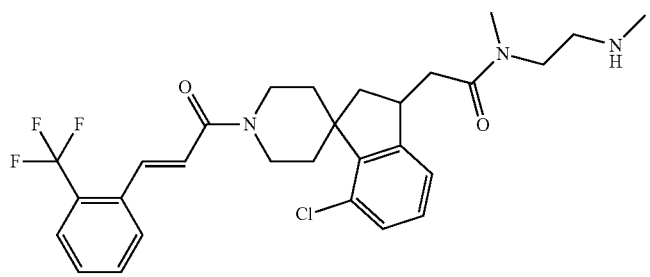

A vial was charged with (±)-(E)-2-(7-bromo-1'-(3-(2-(trifluoromethyl)phenyl)acryloyl)-2,3-dihydrospiro[indene-1,4'-piperidine]-3-yl)acetic acid (5 mg, 0.01 mmol), N,N'-dimethylethylenediamine (0.007 mL, 0.066 mmol), HOBt (3 mg, 0.02 mmol), i-Pr$_2$NEt (0.006 mL, 0.032 mmol) and CH$_2$Cl$_2$ (1 mL). EDC.HCl (4 mg, 0.021 mmol) was added. The mixture was stirred at rt for 1 d and evaporated to dryness. The residue was purified by preparative HPLC to afford (±)-(E)-2-(7-chloro-1'-(3-(2-(trifluoromethyl)phenyl)acryloyl)-2,3-dihydrospiro[indene-1,4'-piperidine]-3-yl)-N-methyl-N-(2-(methylamino)ethyl)acetamide (1.0 mg, 14%). LC-MS Method 1 $t_R$=1.55, min, m/z=548, 550.

Example 8

(±)-(E)-2-(7-chloro-1'-(3-(2-chlorophenyl)acryloyl)-2,3-dihydrospiro[indene-1,4'-piperidine]-3-yl)acetic acid

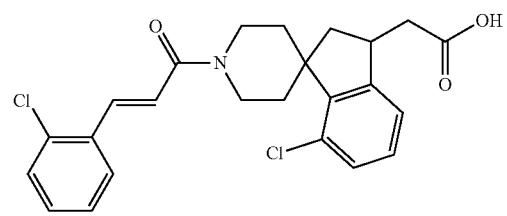 [SMILES: O=C(O)CC1CC2(CCN(C(=O)/C=C/c3ccccc3Cl)CC2)c2c(Cl)cccc21]

The title compound was prepared employing a procedure analogous to that described in Example 1 using methyl 2-(7-chloro-2,3-dihydrospiro[indene-1,4'-piperidine]-3-yl)acetate and 2,3-dichlorocinnamic acid followed by a procedure analogous to that described in Example 2. LC-MS Method 1 $t_R$=1.88, min, m/z=444, 446, 448; $^1$H NMR (CDCl$_3$) 1.40 (dd, 1H), 1.52 (d, 2H), 1.74 (m, 1H), 2.39 (m, 1H), 2.48 (m, 1H), 2.6-3.2 (4H), 3.30 (m, 1H), 3.62 (m, 1H), 4.11 (d, 1H), 4.80 (d, 1H), 6.92 (d, 1H), 7.05-7.30 (5H), 7.41 (m, 1H), 7.62 (m, 1H), 8.00 (d, 1H).

Example 9

(±)-(E)-2-(7-chloro-1'-(3-(2,3-dichlorophenyl)acryloyl)-2,3-dihydrospiro[indene-1,4'-piperidine]-3-yl)acetic acid

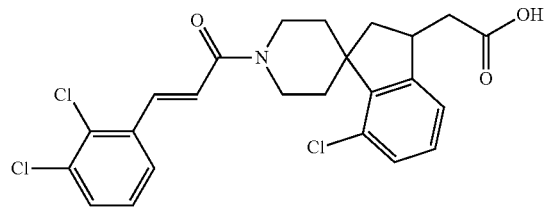 [SMILES: O=C(O)CC1CC2(CCN(C(=O)/C=C/c3cccc(Cl)c3Cl)CC2)c2c(Cl)cccc21]

The title compound was prepared employing a procedure analogous to that described in Example 1 using methyl 2-(7-chloro-2,3-dihydrospiro[indene-1,4'-piperidine]-3-yl)acetate and 2,3-dichlorocinnamic acid followed by a procedure analogous to that described in Example 2. LC-MS Method 1 $t_R$=1.98, min, m/z=480; $^1$H NMR (CDCl$_3$) 1.52 (d, 2H), 1.71 (m, 2H), 2.40 (m, 1H), 2.49 (m, 1H), 2.65-3.10 (4H), 3.32 (m, 1H), 3.62 (m, 1H), 4.13 (d, 1H), 4.79 d, 1H), 6.88 (d, 1H), 7.05-7.30 (4H), 7.46 (d, 1H), 7.52 (d, 1H), 8.00 (d, 1H).

Example 10

(±)-(E)-2-(6-methyl-1'-(3-(2-(trifluoromethyl)phenyl)acryloyl)-2,3-dihydrospiro[indene-1,4'-piperidine]-3-yl)acetic acid

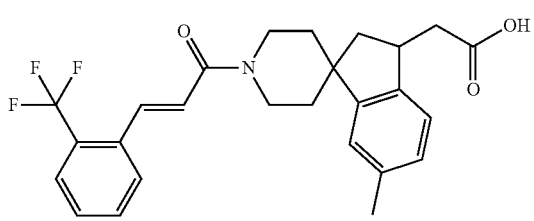 [SMILES: Cc1ccc2c(c1)C1(CCN(C(=O)/C=C/c3ccccc3C(F)(F)F)CC1)CC2CC(=O)O]

The title compound was prepared employing a procedure analogous to that described in Example 1 using methyl 2-(6-methyl-2,3-dihydrospiro[indene-1,4'-piperidine]-3-yl)acetate followed by a procedure analogous to that described in Example 2. LC-MS Method 1 $t_R$=1.92, min, m/z=458; $^1$H NMR (CDCl$_3$) 1.63 (4H), 2.11 (m, 1H), 2.36 (s, 3H), 2.47 (m, 1H), 2.70 (m, 1H), 2.85-3.05 (m, 3H), 3.38 (m, 1H), 3.61 (br s, 1H), 4.10 (m, 1H), 4.76 (m, 1H), 6.84 (m, 1H), 6.98 (s, 1H), 7.05 (m, 2H), 7.44 (m, 1H), 7.58 (m, 1H), 7.67 (m, 2H), 7.97 (d, 1H).

Example 11

(±)-(E)-2-(6-fluoro-1'-(3-(2-(trifluoromethyl)phenyl)acryloyl)-2,3-dihydrospiro[indene-1,4'-piperidine]-3-yl)acetic acid

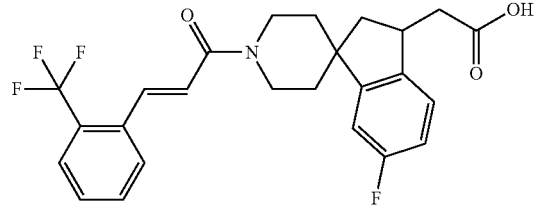 [SMILES: O=C(O)CC1CC2(CCN(C(=O)/C=C/c3ccccc3C(F)(F)F)CC2)c2cc(F)ccc21]

The title compound was prepared employing a procedure analogous to that described in Example 1 using methyl 2-(6-fluoro-2,3-dihydrospiro[indene-1,4'-piperidine]-3-yl)acetate followed by a procedure analogous to that described in Example 2. LC-MS Method 1 $t_R$=, min, m/z=; $^1$H NMR (CDCl$_3$) 1.63 (4H), 2.06 (m, 1H), 2.49 (m, 1H), 2.72 (m, 1H), 2.80-3.00 (3H), 3.38 (m, 1H), 3.62 (br s, 1H), 4.09 (m, 1H), 4.75 (m, 1H), 6.80-7.00 (3H), 7.16 (m, 1H), 7.43 (m, 1H), 7.58 (m, 1H), 7.63 (m, 2H), 7.98 (d, 1H).

Example 12

(±)-(E)-2-(5-methyl-1'-(3-(2-(trifluoromethyl)phenyl)acryloyl)-2,3-dihydrospiro[indene-1,4'-piperidine]-3-yl)acetic acid

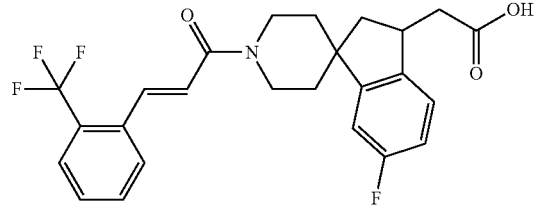 [SMILES: O=C(O)CC1CC2(CCN(C(=O)/C=C/c3ccccc3C(F)(F)F)CC2)c2cc(F)ccc21]

The title compound was prepared employing a procedure analogous to that described in Example 1 using methyl 2-(5-methyl-2,3-dihydrospiro[indene-1,4'-piperidine]-3-yl)acetate followed by a procedure analogous to that described in Example 2. $^1$H NMR (CDCl$_3$) 1.61 (4H), 2.10 (m, 1H), 2.32 (s, 3H), 2.47 (m, 1H), 2.70 (m, 1H), 2.85-3.05 (3H), 2.37 (m, 1H), 3.62 (br s, 1H), 4.06 (m, 1H), 4.73 (m, 1H), 6.83 (m, 1H), 7.02 (s, 1H), 7.08 (s, 2H), 7.43 (m, 1H), 7.57 (m, 1H), 7.80 (m, 2H), 7.98 (d, 1H)

Example 13

(±)-(E)-2-(7-bromo-1'-(3-(2-(trifluoromethyl)phenyl)acryloyl)-2,3-dihydrospiro[indene-1,4'-piperidine]-3-yl)acetamide

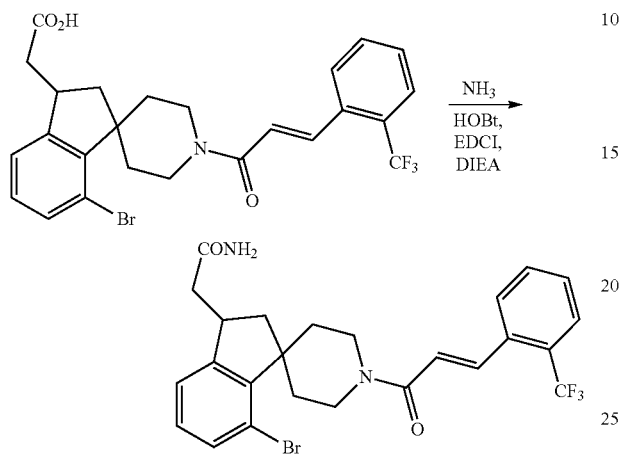

To a solution of (E)-2-(7-bromo-1'-(3-(2-(trifluoromethyl)phenyl)acryloyl)-2,3-dihydro spiro[indene-1,4'-piperidine]-3-yl)acetic acid isomer 1 (100 mg, 0.19 mmol) in anhydrous CH$_2$Cl$_2$ (4 mL) were added HOBt (52 mg, 0.38 mmol), EDCI (76 mg, 0.38 mmol) and i-Pr$_2$NEt (123 mg, 0.95 mmol) in an ice water bath. The mixture was stirred overnight under NH$_3$ at rt. The reaction mixture was washed with 1 N aq HCl and the aqueous phase was extracted with CH$_2$Cl$_2$ (2×). The combined organic phases were dried, filtered and concentrated to give a residue, which was purified by preparative TLC to afford (±)-(E)-2-(7-bromo-1'-(3-(2-(trifluoromethyl)phenyl)acryloyl)-2,3-dihydrospiro[indene-1,4'-piperidine]-3-yl)acetamide isomer 1 (52 mg, 53%). $^1$H NMR (CD$_3$OD): 1.52 (m, 2H), 1.82 (m, 1H), 4.01 (m, 1H), 2.35 (m, 1H), 2.76 (m, 2H), 3.08 (m, 2H), 3.41 (m, 1H), 3.62 (m, 1H), 4.31 (m, 1H), 4.62 (m, 1H), 4.71 (m, 1H), 7.12 (m, 1H), 7.22 (m, 2H), 7.38 (m, 1H), 7.53 (m, 1H), 7.66 (m, 1H), 7.72 (m, 1H), 7.98 (m, 2H).

Example 14

(±)-(E)-2-(6-fluoro-1'-(3-(2-(trifluoromethyl)phenyl)acryloyl)-2,3-dihydrospiro[indene-1,4'-piperidine]-3-yl)acetamide

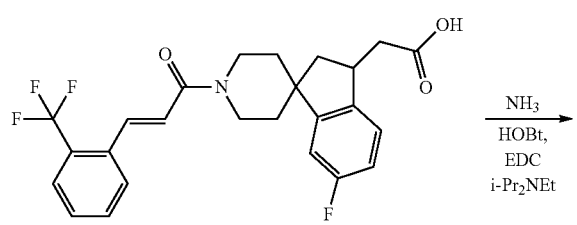

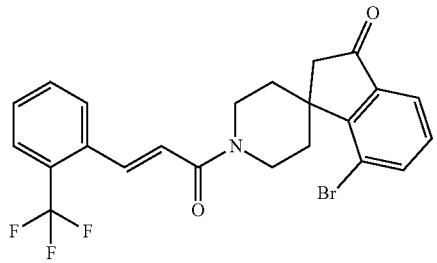 [SMILES: O=C1CC2(CCN(C(=O)/C=C/c3ccccc3C(F)(F)F)CC2)c2c(Br)cccc21]

The title compound was prepared following a procedure analogous to that described in Example 7 using 0.5 M NH$_3$ in dioxane and (±)-(E)-2-(6-fluoro-1'-(3-(2-(trifluoromethyl)phenyl)acryloyl)-2,3-dihydrospiro[indene-1,4'-piperidine]-3-yl)acetic acid. LC-MS Method 1 t$_R$=1.67, min, m/z=461.

Example 15

(E)-7-bromo-1'-(3-(2-(trifluoromethyl)phenyl)acryloyl)spiro[indene-1,4'-piperidin]-3(2H)-one

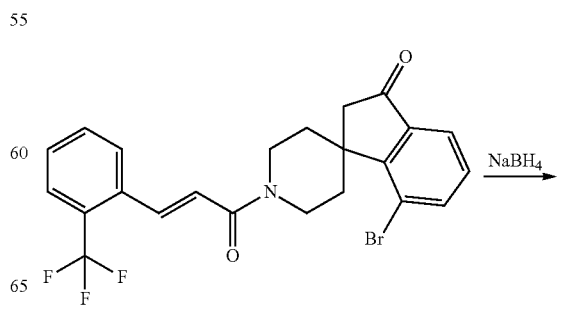

The title compound was prepared following a procedure analogous to that described in Example 1 using 7-bromospiro[indene-1,4'-piperidin]-3(2H)-one. LC-MS Method 1 t$_R$=1.92, min, m/z=478, 480; $^1$H NMR (CDCl$_3$) 1.45 (m, 2H), 2.78 (m, 3H), 3.03 (m, 2H), 3.29 (m, 1H), 4.22 (m, 1H), 4.91 (m, 1H), 6.83 (d, 1H), 7.20-8.00 (8H).

Example 16

(±)-(E)-1-(7-bromo-3-hydroxy-2,3-dihydrospiro[indene-1,4'-piperidine]-1'-yl)-3-(2-(trifluoromethyl)phenyl)prop-2-en-1-one

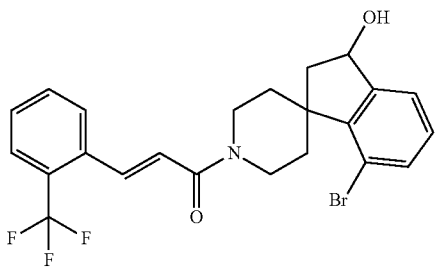

To a stirred solution of (E)-7-bromo-1'-(3-(2-(trifluoromethyl)phenyl)acryloyl)spiro[indene-1,4'-piperidin]-3(2H)-one (20 mg, 0.042 mmol) in MeOH (2 mL) and THF (2 mL) was added solid NaBH₄ (12 mg). The mixture was stirred at rt for 3 h. The mixture was diluted with 10% aq citric acid and extracted with ether (2×30 mL). The combined ether extracts were dried over MgSO₄ and concentrated. The residue was purified by prep HPLC to afford (±)-(E)-1-(7-bromo-3-hydroxy-2,3-dihydrospiro[indene-1,4'-piperidine]-1'-yl)-3-(2-(trifluoromethyl)phenyl)prop-2-en-1-one (1.8 mg, 9%) as a solid. LC-MS Method 1 $t_R$=1.83, min, m/z=480, 482; ¹H NMR (CDCl₃) 1.39 (m, 2H), 1.63 (m, 1H), 2.12 (m, 1H), 2.5-3.0 (4H), 3.36 (m, 1H), 4.16 (m, 1H), 4.82 (m, 1H), 5.23 (br s, 1H), 6.86 (d, 1H), 7.18 (m, 1H), 7.3-7.8 (6H), 7.95 (d, 1H).

Example 17

(E)-7-bromo-1'-(3-(2,6-dichlorophenyl)acryloyl)spiro[indene-1,4'-piperidin]-3(2H)-one

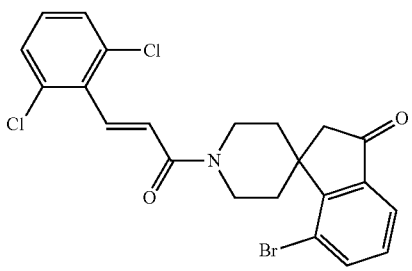

The title compound was prepared following a procedure analogous to that described in Example 15 using 2,6-dichlorocinnamic acid. LC-MS Method 1 $t_R$=1.95, min, m/z=478, 480, 482; ¹H NMR (CDCl₃) 1.45 (2H), 2.7-2.9 (3H), 3.00 (m, 2H), 3.29 (m, 1H), 4.20 (m, 1H), 4.92 (m, 1H), 6.6-8.0 (8H).

Example 18

(±)-(E)-1-(3-amino-7-bromo-2,3-dihydrospiro[indene-1,4'-piperidine]-1'-yl)-3-(2-(trifluoromethyl)phenyl)prop-2-en-1-one

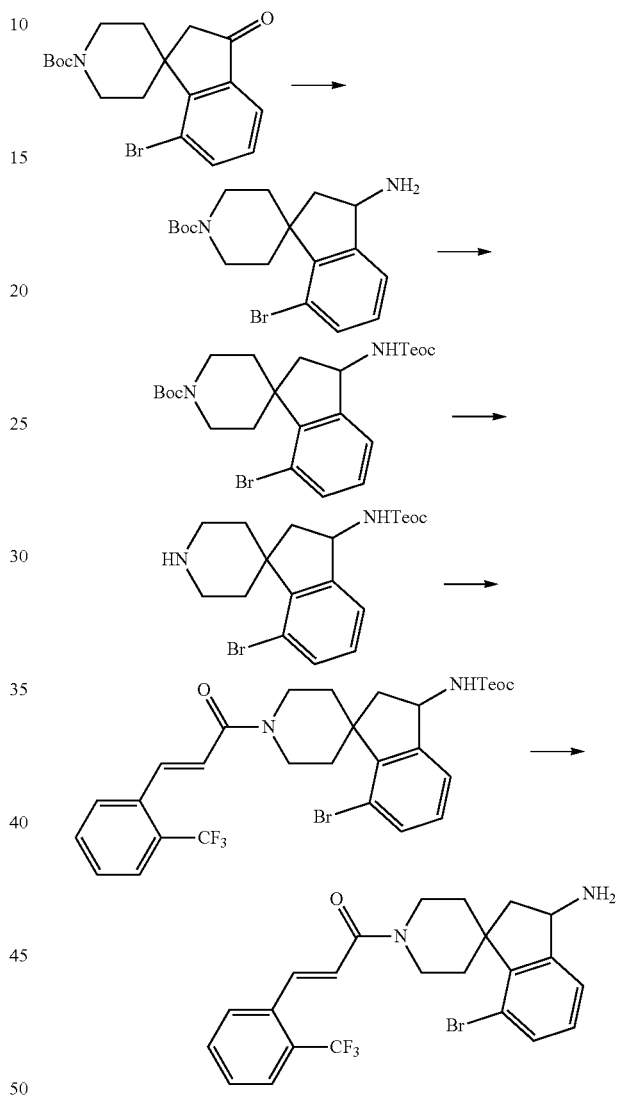

Step 1

To a stirred solution of tert-butyl 7-bromo-3-oxo-2,3-dihydrospiro[indene-1,4'-piperidine]-1'-carboxylate (196 mg, 0.52 mmol) in MeOH (20 mL) were added NH₄OAc (795 mg, 10.3 mmol) and NaCNBH₃ (324 mg, 5.2 mmol). The mixture was heated at reflux for 1 d. The mixture was concentrated under reduced pressure, diluted with EtOAc (90 mL), washed with 1M aq NaOH (25 mL) and dried over Na₂SO₄. Removal of the solvent gave crude (±)-tert-butyl 3-amino-7-bromo-2,3-dihydrospiro[indene-1,4'-piperidine]-1'-carboxylate (264 mg) which was used without purification.

Step 2

To a stirred solution of crude (±)-tert-butyl 3-amino-7-bromo-2,3-dihydrospiro[indene-1,4'-piperidine]-1'-carboxylate (264 mg, 0.69 mmol) in THF (5 mL) was added 10% aq K₂CO₃ (10 mL), followed by Teoc-OSu (269 mg, 1.04 mmol). The mixture was stirred at rt for 3 d, diluted with ether (80 mL), washed with brine (25 mL) and dried over MgSO₄. Removal of the solvent left an oil (240 mg) which was purified chromatography on a 12-g silica cartridge, eluted with a 0-50% EtOAc in hexanes gradient to afford (±)-tert-butyl 7-bromo-3-((2-(trimethylsilyl)ethoxy)carbonylamino)-2,3-dihydrospiro[indene-1,4'-piperidine]-1'-carboxylate (85 mg, 31% for 2 steps). LC-MS Method 1 $t_R$=2.35 min, m/z=425, 427, 547, 549.

Step 3

A solution of (±)-tert-butyl 7-bromo-3-((2-(trimethylsilyl)ethoxy)carbonylamino)-2,3-dihydrospiro[indene-1,4'-piperidine]-1'-carboxylate (85 mg, 0.16 mmol) and TsOH.H₂O (32 mg, 0.17 mmol) in EtOH (2 mL) and Et₂O (30 mL) was placed under vacuum on a rotary evaporator and the water bath was warmed from rt to 60° C. The mixture was held under vacuum at 60° C. for 1 h. The solid residue was dissolved in CH₂Cl₂ (100 mL), washed with satd aq NaHCO₃ (10 mL) and dried over Na₂SO₄. Removal of the solvent left (±)-2-(trimethylsilyl)ethyl 7-bromo-2,3-dihydrospiro[indene-1,4'-piperidine]-3-ylcarbamate (56 mg, 81%) as an oil. LC-MS Method 1 $t_R$=1.50 min, m/z=425, 427.

Step 4

To a stirred solution of (±)-2-(trimethylsilyl)ethyl 7-bromo-2,3-dihydrospiro[indene-1,4'-piperidine]-3-ylcarbamate (23 mg, 0.056 mmol), ortho-(trifluoromethyl)cinnamic acid (16 mg, 0.074 mmol) and i-Pr₂NEt (0.027 mL, 0.15 mmol) in CH₂Cl₂ (3 mL) was added solid HATU (28 mg, 0.0.074 mmol). The mixture was stirred overnight at rt and evaporated to leave a residue which was purified by preparative HPLC to afford (±)-(E)-2-(trimethylsilyl)ethyl 7-bromo-1'-(3-(2-(trifluoromethyl)phenyl)acryloyl)-2,3-dihydrospiro[indene-1,4'-piperidine]-3-ylcarbamate (16.5 mg, 47%). LC-MS Method 1 $t_R$=2.37 min, m/z=623, 625.

Step 5

(±)-(E)-2-(trimethylsilyl)ethyl 7-bromo-1'-(3-(2-(trifluoromethyl)phenyl)acryloyl)-2,3-dihydrospiro[indene-1,4'-piperidine]-3-ylcarbamate (16.5 mg, 0.026 mmol) and Et₄NF (30 mg) were dissolved in MeCN (3 mL). The solution was heated at 100° C. for 10 min in a microwave. The solution was concentrated and the residue was purified by preparative HPLC to give (±)-(E)-1-(3-amino-7-bromo-2,3-dihydrospiro[indene-1,4'-piperidine]-1'-yl)-3-(2-(trifluoromethyl)phenyl)prop-2-en-1-one (11 mg, 70%) as its TFA salt. LC-MS Method 1 $t_R$=1.38, min, m/z=479, 481; ¹H NMR (CD₃OD) 1.53 (m, 1H), 1.67 (m, 1H), 2.08 (m, 1H), 2.55 (m, 1H), 2.9-3.5 (5H), 4.38 (d, 1H), 4.72 (d, 1H), 7.2-8.0 (9H).

Example 19

(±)-(E)-1-(7-bromo-1'-(3-(2-(trifluoromethyl)phenyl)acryloyl)-2,3-dihydrospiro[indene-1,4'-piperidine]-3-yl)-3-methylurea

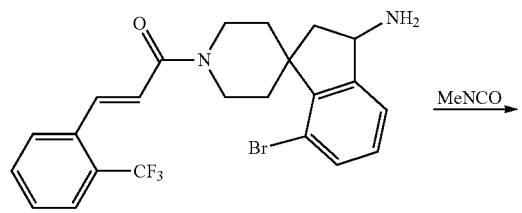

MeNCO →

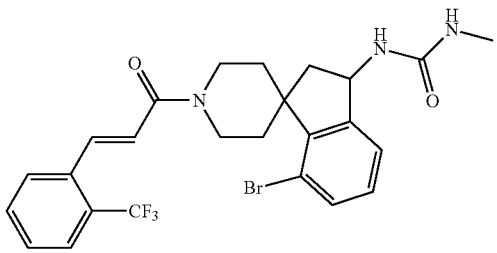

A vial equipped with a flea stirbar was charged with (±)-(E)-1-(3-amino-7-bromo-2,3-dihydrospiro[indene-1,4'-piperidine]-1'-yl)-3-(2-(trifluoromethyl)phenyl)prop-2-en-1-one TFA salt (9 mg, 0.015 mmol), i-Pr₂NEt (0.01 mL) and CH₂Cl₂ (1 mL). MeNCO (0.05 mL, 0.085 mmol) was added. The mixture was stirred at rt for 3 h and evaporated to dryness. The residue was purified by prep HPLC to afford (±)-(E)-1-(7-bromo-1'-(3-(2-(trifluoromethyl)phenyl)acryloyl)-2,3-dihydrospiro[indene-1,4'-piperidine]-3-yl)-3-methylurea (2.9 mg, 59%). LC-MS Method 1 $t_R$=1.77, min, m/z=536, 538.

Example 20

(E)-tert-butyl 1'-(3-(2-(trifluoromethyl)phenyl)acryloyl)-1H-spiro[isoquinoline-4,4'-piperidine]-2(3H)-carboxylate

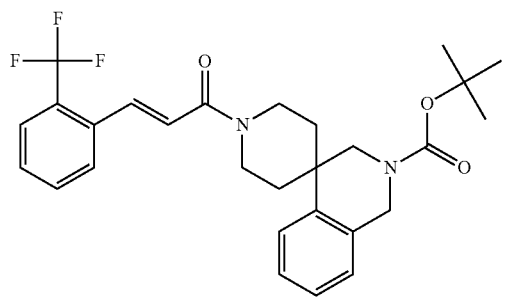 [SMILES: CC(C)(C)OC(=O)N1Cc2ccccc2C2(CCN(C(=O)/C=C/c3ccccc3C(F)(F)F)CC2)C1]

The title compound was prepared following a procedure analogous to that described in Example 1 using tert-butyl 1H-spiro[isoquinoline-4,4'-piperidine]-2(3H)-carboxylate. LC-MS Method 1 $t_R$=2.18, min, m/z=501; ¹H NMR (CDCl₃) 1.48 (s, 9H), 1.60-2.20 (4H), 3.05 (m, 1H), 3.40-4.20 (4H), 4.50-4.80 (3H), 6.85 (d, 1H), 7.12 (m, 1H), 7.20 (m, 2H), 7.35 (m, 1H), 7.44 (m, 1H), 7.58 (m, 1H), 7.69 (m, 2H), 7.99 (m, 1H).

Example 21

(E)-1-(2,3-dihydro-1H-spiro[isoquinoline-4,4'-piperidine]-1'-yl)-3-(2-(trifluoromethyl)phenyl)prop-2-en-1-one

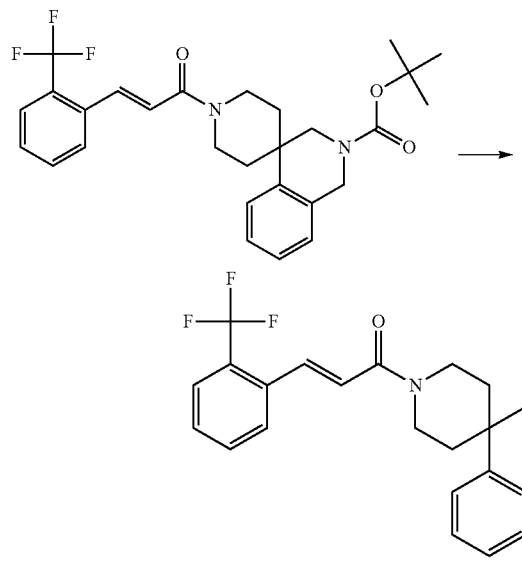

To a stirred solution of (E)-tert-butyl 1'-(3-(2-(trifluoromethyl)phenyl)acryloyl)-1H-spiro[isoquinoline-4,4'-piperidine]-2(3H)-carboxylate (64 mg, 0.13 mmol) in CH₂Cl₂ (2 mL) was added 4 M HCl in dioxane (2 mL). The mixture was stirred at rt for 2 h and concentrated to afford (E)-1-(2,3-dihydro-1H-spiro[isoquinoline-4,4'-piperidine]-1'-yl)-3-(2-(trifluoromethyl)phenyl)prop-2-en-1-one as its hydrochloride salt. LC-MS Method 1 $t_R$=1.26, min, m/z=401.

Example 22

(E)-1-(2-(methylsulfonyl)-2,3-dihydro-1H-spiro[isoquinoline-4,4'-piperidine]-1'-yl)-3-(2-(trifluoromethyl)phenyl)prop-2-en-1-one

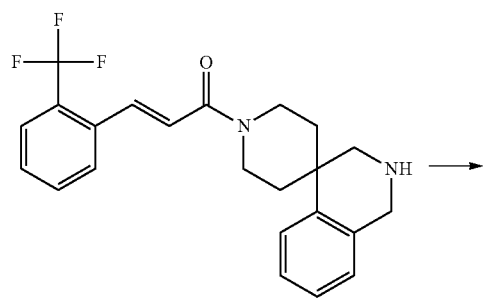

-continued

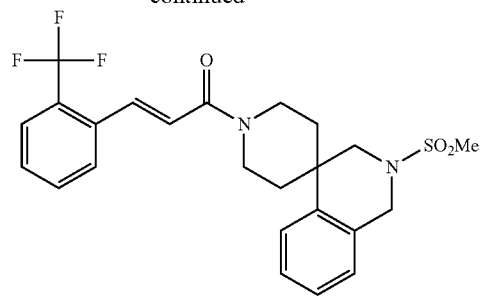

A solution of (E)-1-(2,3-dihydro-1H-spiro[isoquinoline-4,4'-piperidine]-1'-yl)-3-(2-(trifluoromethyl)phenyl)prop-2-en-1-one HCl salt (40 mg, 0.09 mmol) in CH₂Cl₂ (4 mL) was treated with i-Pr₂NEt (0.05 mL, 0.28 mmol) and MeSO₂Cl (0.014 mL, 0.18 mmol). The mixture was stirred overnight at rt and applied to a 10-mL Chem-Elut cartridge that had been wetted with 5% aq HCl (6 mL). The cartridge was eluted with ether (20 mL). The eluate was concentrated and the residue was purified by prep HPLC to afford (E)-1-(2-(methylsulfonyl)-2,3-dihydro-1H-spiro[isoquinoline-4,4'-piperidine]-1'-yl)-3-(2-(trifluoromethyl)phenyl)prop-2-en-1-one (20 mg, 45%). ¹H NMR (CDCl₃) 1.77 (m, 1H), 1.88 (m, 1H), 2.04 (m, 1H), 2.13 (m, 1H), 2.92 (s, 3H), 3.00 (m, 1H), 3.23 (m, 1H), 3.47 (m, 1H), 3.90 (m, 1H), 4.02 (m, 1H), 4.37 (m, 1H), 4.59 (m, 1H), 4.78 (d, 1H), 6.82 (d, 1H), 7.05-7.75 (8H), 7.99 (d, 1H).

Example 23

(E)-1-(2-acetyl-2,3-dihydro-1H-spiro[isoquinoline-4,4'-piperidine]-1'-yl)-3-(2-(trifluoromethyl)phenyl)prop-2-en-1-one

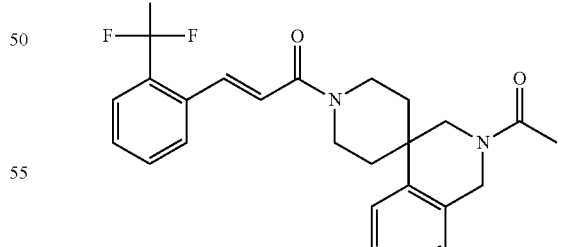

The title compound was prepared following a procedure analogous to that described in Example 22 using acetic anhydride in place of methanesulfonyl chloride. ¹N NMR (CDCl₃) 1.64 (m, 2H), 1.81 (m, 1H), 2.14 (m, 1H), 2.13 (3H), 3.08 (m, 1H), 3.60 (m, 2H), 4.0 (m, 1H), 4.39 (d, 1H), 4.70 (3H), 6.82 (d, 1H), 7.1-7.75 (8H), 7.99 (d, 1H).

2H), 2.99 (2H), 3.38 (s, 3H), 3.68 (m, 1H), 3.90 (m, 1H), 4.0 (m, 1H), 4.48 (m, 1H), 6.82 (d, 1H), 7.4-7.8 (7H), 8.0 (d, 1H).

Example 24

(E)-2-methyl-1'-(3-(2-(trifluoromethyl)phenyl)acryloyl)spiro[isoindoline-1,4'-piperidin]-3-one

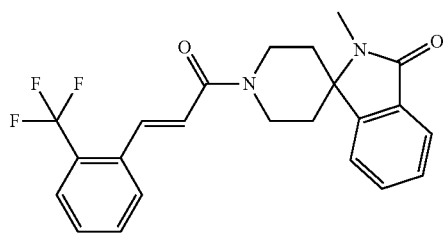 [SMILES: CN1C(=O)c2ccccc2C12CCN(C(=O)/C=C/c1ccccc1C(F)(F)F)CC2]

The title compound was prepared following a procedure analogous to that described in Example 1 using 2-methylspiro[isoindoline-1,4'-piperidin]-3-one. LC-MS Method 1 $t_R$=1.65, min, m/z=415; $^1$H NMR (CDCl$_3$) 1.60 (d, 2H), 2.23 (m, 2H), 3.06 (s, 3H), 3.46 (m, 1H), 3.84 (m, 1H), 4.23 (m, 1H), 4.86 (m, 1H), 6.87 (d, 1H), 7.4-8.1 (9H)

Example 25

(E)-7-chloro-2-methyl-1'-(3-(2-(trifluoromethyl)phenyl)acryloyl)spiro[isoindoline-1,4'-piperidin]-3-one

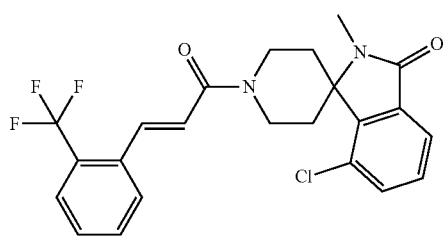 [SMILES: CN1C(=O)c2cccc(Cl)c2C12CCN(C(=O)/C=C/c1ccccc1C(F)(F)F)CC2]

The title compound was prepared following a procedure analogous to that described in Example 1 using 7-chloro-2-methylspiro[isoindoline-1,4'-piperidin]-3-one. LC-MS Method 1 $t_R$=1.75, min, m/z=449; $^1$H NMR (CDCl$_3$) 1.85 (m,

Example 26

(E)-7-chloro-1'-(3-(2,6-dichlorophenyl)acryloyl)-2-methylspiro[isoindoline-1,4'-piperidin]-3-one

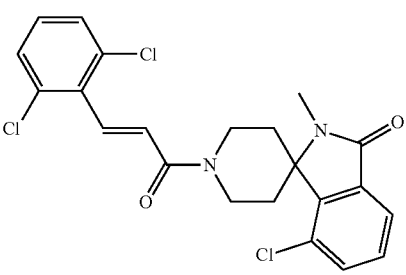 [SMILES: CN1C(=O)c2cccc(Cl)c2C12CCN(C(=O)/C=C/c1c(Cl)cccc1Cl)CC2]

The title compound was prepared following a procedure analogous to that described in Example 1 using 7-chloro-2-methylspiro[isoindoline-1,4'-piperidin]-3-one and 2,6-dichlorocinnamic acid. $^1$H NMR (CDCl$_3$) 1.82 (m, 2H), 2.99 (m, 2H), 3.35 (s, 3H), 3.68 (m, 1H), 3.88 (m, 1H), 4.18 (m, 1H), 4.49 (m, 1H), 7.06 (d, 1H), 7.1-7.6 (5H), 7.76 (2H).

Example 27

(E)-7-chloro-1'-(3-(2-(trifluoromethyl)phenyl)acryloyl)spiro[isoindoline-1,4'-piperidin]-3-one

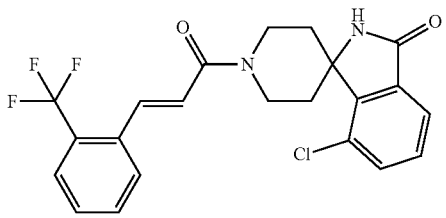 [SMILES: O=C1NC2(CCN(C(=O)/C=C/c3ccccc3C(F)(F)F)CC2)c2c(Cl)cccc21]

The title compound was prepared following a procedure analogous to that described in Example 1 using 7-chlorospiro[isoindoline-1,4'-piperidin]-3-one. LC-MS Method 1 $t_R$=1.73, min, m/z=435.

Example 28

(E)-7-bromo-1'-(3-(2-(trifluoromethyl)phenyl)acryloyl)spiro[isoindoline-1,4'-piperidin]-3-one

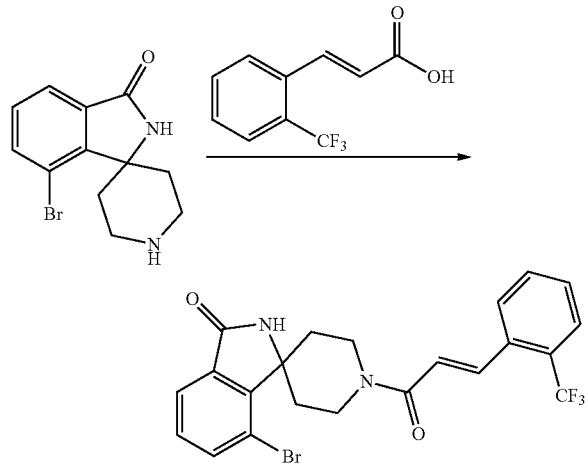

A mixture of 7-bromospiro[isoindoline-1,4'-piperidin]-3-one (194 mg, 0.69 mmol), 3-(2-(trifluoromethyl)phenyl)acrylic acid (100 mg, 0.46 mmol), EDCI (181 mg, 0.92 mmol), HOBt (124 mg, 0.92 mmol) and i-Pr$_2$NEt (1 mL) was stirred at rt overnight. The mixture was washed with 5% aq HCl, and the organic layer was concentrated to give a residue which was purified by preparative HPLC to afford (E)-7-bromo-1'-(3-(2-(trifluoromethyl)phenyl)acryloyl)spiro[isoindoline-1,4'-piperidin]-3-one (5 mg, 2%). $^1$H NMR (400 MHz, CDCl$_3$): δ=1.53 (m, 2H), 2.98 (m, 3H), 3.42 (m, 1H), 4.23 (m, 1H), 4.50 (m, 1H), 4.93 (m, 1H), 6.80 (m, 1H), 7.33 (m, 1H), 7.40 (m, 1H), 7.50 (m, 1H), 7.65 (m, 3H), 7.77 (m, 1H), 7.95 (m, 1H), 8.50 (m, 1H).

Example 29

(E)-5,7-dichloro-1'-(3-(2-(trifluoromethyl)phenyl)acryloyl)spiro[isoindoline-1,4'-piperidin]-3-one

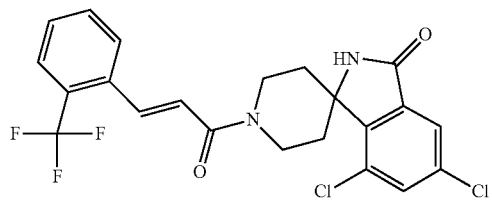 [SMILES: O=C1NC2(CCN(C(=O)/C=C/c3ccccc3C(F)(F)F)CC2)c2c(Cl)cc(Cl)cc21]

The title compound was prepared following a procedure analogous to that described in Example 28 using 5,7-dichlorospiro[isoindoline-1,4'-piperidin]-3-one. $^1$H NMR (d$_6$-DMSO): 1.47 (m, 2H), 2.58 (m, 1H), 3.06 (m, 1H), 4.44 (m, 1H), 4.61 (m, 1H), 7.45 (m, 1H), 7.57 (m, 1H), 7.72 (m, 4H), 7.85 (m, 1H), 8.15 (m, 1H), 9.96 (s, 1H).

Example 30

(E)-1-(6-methoxy-3,4-dihydro-2H-spiro[isoquinoline-1,4'-piperidine]-1'-yl)-3-(2-(trifluoromethyl)phenyl)prop-2-en-1-one

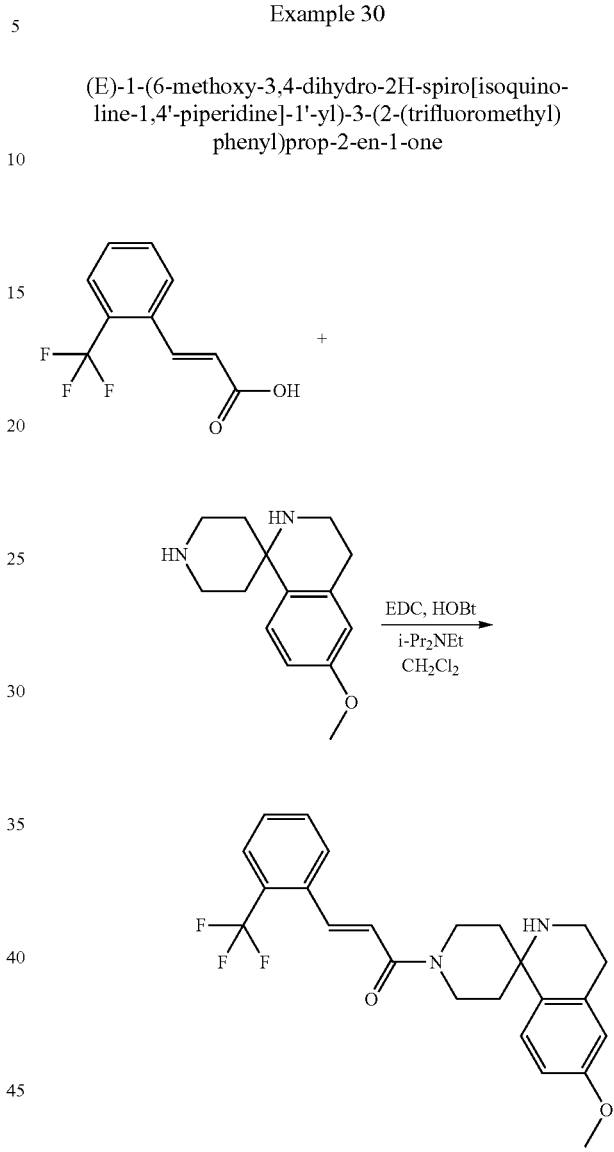

To a stirred solution of 6-methoxy-3,4-dihydro-2H-spiro[isoquinoline-1,4'-piperidine] (570 mg, 2.45 mmol) in CH$_2$Cl$_2$ (20 mL) were added ortho-(trifluoromethyl)cinnamic acid (132 mg, 0.61 mmol), i-Pr$_2$NEt (0.43 mL, 2.45 mmol), HOBt (99 mg, 0.73 mmol) and EDC.HCl (141 mg, 0.73 mmol). The mixture was stirred at rt for 3 d. The mixture was diluted with EtOAc (80 mL), washed with water (30 mL) and satd aq NaHCO$_3$ (30 mL), and dried over Na$_2$SO$_4$. Removal of the solvent left an orange oil (378 mg). A portion of the oil was purified by preparative HPLC to afford (E)-1-(6-methoxy-3,4-dihydro-2H-spiro[isoquinoline-1,4'-piperidine]-1'-yl)-3-(2-(trifluoromethyl)phenyl)prop-2-en-1-one. LC-MS Method 1 t$_R$=1.37, min, m/z=431; $^1$H NMR (CDCl$_3$) 2.25 (m, 4H), 3.16 (br s, 2H), 3.39 (m, 1H), 3.45 (br s, 2H), 3.78 (s, 3H), 3.84 (m, 1H), 4.11 (m, 1H), 4.78 (m, 1H), 4.9 (1H), 6.65 (s, 1H), 6.83 (m, 2H), 7.12 (d, 1H), 7.4-7.75 (4H), 7.98 (d, 1H).

Example 31

(E)-1-methyl-1'-(3-(2-(trifluoromethyl)phenyl)acryloyl)spiro[indoline-3,4'-piperidin]-2-one

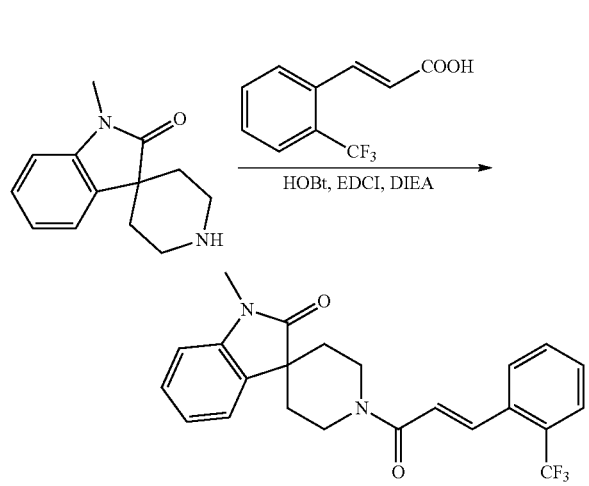

A solution of 1-methylspiro[indoline-3,4'-piperidin]-2-one (100 mg, 0.46 mmol) in CH$_2$Cl$_2$ (5 mL) was added 3-(2-trifluoromethyl-phenyl)-acrylic acid (120 mg, 0.56 mmol), HOBt (124 mg, 0.92 mmol), EDCI (181 mg, 0.92 mmol) and DIEA (297 mg, 2.30 mmol). The reaction mixture was stirred at rt overnight. The above mixture was concentrated and the residue was purified by preparative HPLC to give (E)-1-methyl-1'-(3-(2-(trifluoromethyl)phenyl)acryloyl)spiro[indoline-3,4'-piperidin]-2-one (50 mg, 26%). $^1$H NMR (CDCl$_3$): 1.85-2.00 (m, 4H), 3.72 (s, 3H), 3.90-4.00 (m, 2H), 4.15-4.30 (m, 1H), 4.40-4.50 (m, 1H), 6.80-6.90 (m, 2H), 7.10-7.15 (m, 1H), 7.25-7.35 (m, 2H), 7.45-7.60 (m, 2H), 7.68-7.72 (m, 2H), 7.91-8.00 (m, 1H).

Example 32

(E)-methyl 1-methyl-2-oxo-1'-(3-(2-(trifluoromethyl)phenyl)acryloyl)spiro[indoline-3,4'-piperidine]-5-carboxylate

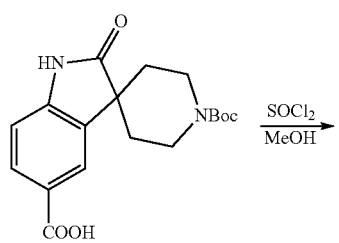

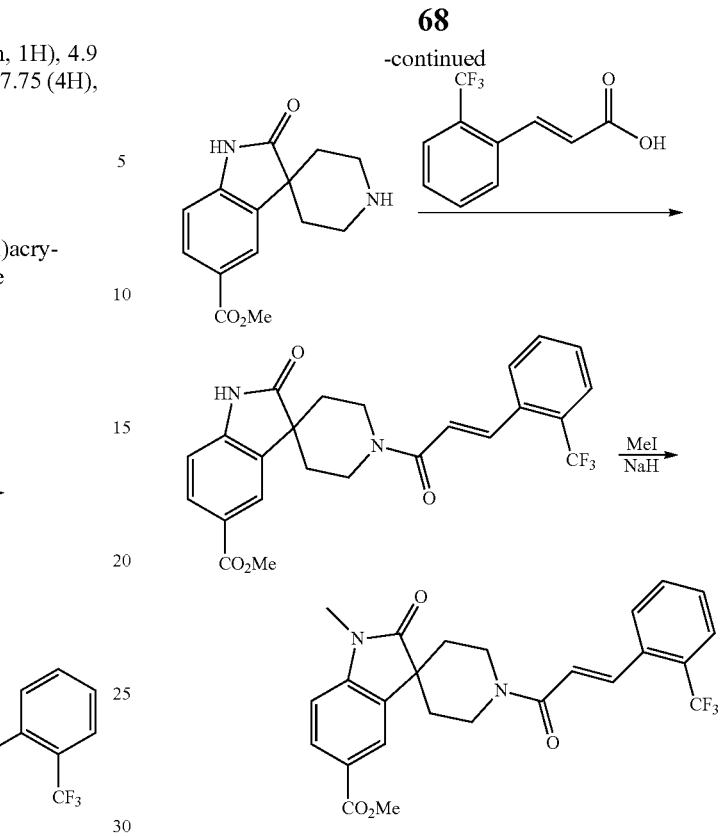

Step 1

To a solution of 1'-(tert-butoxycarbonyl)-2-oxospiro[indoline-3,4'-piperidine]-5-carboxylic acid (2 g, 6.0 mmol) in methanol (30 mL) was added dropwise SOCl$_2$ (5 mL) at 0° C. Then the reaction mixture was stirred overnight at rt. The reaction mixture was concentrated to give methyl 2-oxospiro[indoline-3,4'-piperidine]-5-carboxylate hydrochloride (1.4 g, 81%), which was used for the next step without purification. $^1$H NMR (CD$_3$OD): 2.00 (m, 2H), 2.20 (m, 2H), 3.281 (m, 1H), 3.39 (m, 2H), 3.61 (m, 2H), 3.85 (m, 2H), 3.88 (m, 2H), 7.00 (m, 1H), 7.98 (m, 2H).

Step 2

To a solution of methyl 2-oxospiro[indoline-3,4'-piperidine]-5-carboxylate hydrochloride (400 mg, 1.46 mmol) in anhydrous CH$_2$Cl$_2$ (10 mL) was added (E)-3-(2-(trifluoromethyl)phenyl)acrylic acid (315 mg, 1.46 mmol), HOBt (394 mg, 2.92 mmol), EDCI (576 mg, 2.92 mmol) and DIEA (942 mg, 7.30 mol) at 0° C. and then stirred overnight at rt under N$_2$. Then the reaction mixture was washed with 1 N aq HCl and water. The organic layer was dried over Na$_2$SO$_4$, filtered and concentrated to afford a residue, which was purified by preparative TLC to give (E)-methyl 2-oxo-1'-(3-(2-(trifluoromethyl)phenyl)acryloyl)spiro[indoline-3,4'-piperidine]-5-carboxylate (328 mg, 49%). $^1$H NMR (CDCl$_3$): 1.58 (m, 4H), 1.97 (m, 3H), 3.91 (m, 3H), 4.15 (m, 1H), 4.40 (m, 1H), 6.85 (m, 1H), 6.98 (m, 1H), 7.48 (m, 1H), 7.56 (m, 1H), 7.72 (m, 1H), 7.99 (m, 2H).

Step 3

A solution of (E)-methyl 2-oxo-1'-(3-(2-(trifluoromethyl)phenyl)acryloyl)spiro[indoline-3,4'-piperidine]-5-carboxylate (150 mg, 0.33 mmol) in THF (3 mL) was added to a suspension of NaH (27 mg, 0.66 mmol) in THF at 0° C. and stirred for 30 min at the same temperature. Methyl iodide (58 mg, 0.41 mmol) was added to the above mixture. The reaction mixture was stirred at rt for 2 h. The reaction mixture was poured into ice water and extracted with EtOAc (2×50 mL).

The combined organic phases were dried over NaSO$_4$, filtered and concentrated to give (E)-methyl 1-methyl-2-oxo-1'-(3-(2-(trifluoromethyl)phenyl)acryloyl)spiro[indoline-3,4'-piperidine]-5-carboxylate (90 mg, 58%). $^1$H NMR (CD$_3$OD): 1.85-2.02 (m, 4H), 3.26 (s, 3H), 3.88 (s, 3H), 3.95 (m, 1H), 4.15 (m, 1H), 4.28 (m, 1H), 7.10 (m, 1H), 7.26 (m, 1H), 7.52 (m, 1H), 7.68 (m, 1H), 7.77 (m, 1H), 8.06 (m, 4H).

Example 33

(E)-1-methyl-2-oxo-1'-(3-(2-(trifluoromethyl)phenyl)acryloyl)spiro[indoline-3,4'-piperidine]-5-carboxylic acid

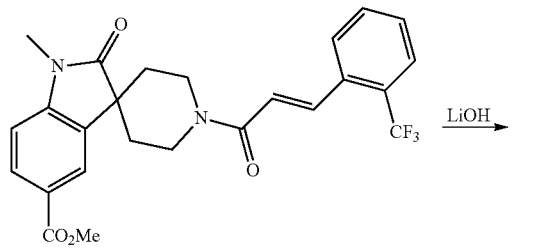

To a solution of (E)-methyl 1-methyl-2-oxo-1'-(3-(2-(trifluoromethyl)phenyl)acryloyl)spiro[indoline-3,4'-piperidine]-5-carboxylate (75 mg, 0.16 mmol) in methanol (4 mL) was added a solution of LiOH in H$_2$O (2 M, 4 mL) at rt and the mixture was stirred for 8 h at rt. The reaction mixture was concentrated to remove methanol and extracted with CH$_2$Cl$_2$ twice. The combined organic phases were dried, filtered and concentrated to give (E)-1-methyl-2-oxo-1'-(3-(2-(trifluoromethyl)phenyl)acryloyl)spiro[indoline-3,4'-piperidine]-5-carboxylic acid (106 mg, 65%). $^1$H NMR (CD$_3$OD): 1.94 (m, 4H), 3.26 (s, 3H), 4.15 (m, 3H), 4.22 (m, 1H), 7.01 (d, 1H), 7.28 (d, 1H), 7.53 (m, 1H), 7.66 (m, 1H), 7.76 (m, 1H), 8.01 (m, 3H), 8.08 (m, 1H).

Example 34

(E)-N,N,1-trimethyl-2-oxo-1'-(3-(2-(trifluoromethyl)phenyl)acryloyl)spiro[indoline-3,4'-piperidine]-5-carboxamide

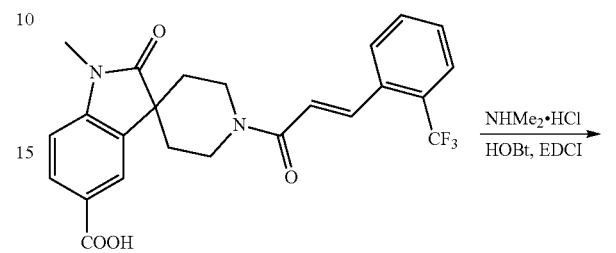

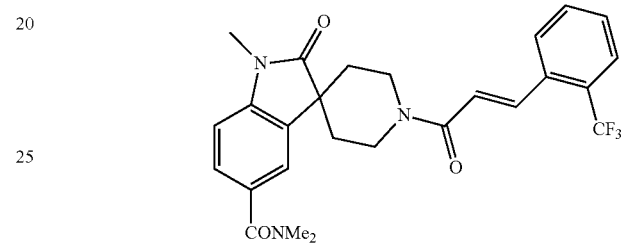

To a mixture of (E)-1-methyl-2-oxo-1'-(3-(2-(trifluoromethyl)phenyl)acryloyl)spiro[indoline-3,4'-piperidine]-5-carboxylic acid (20 mg, 0.508 mmol), EDCI (18 mg, 0.088 mmol), HOBt (12 mg, 0.088 mmol), and DIEA (60 mg, 0.44 mmol) in CH$_2$Cl$_2$ was added NHMe$_2$.HCl (16 mg, 0.176 mmol) at 0° C. The mixture was stirred at rt overnight. The mixture was concentrated to give the crude product, which was purified by preparative TLC to give (E)-N,N,1-trimethyl-2-oxo-1'-(3-(2-(trifluoromethyl)phenyl)acryloyl)spiro[indoline-3,4'-piperidine]-5-carboxamide (6 mg, 14%). $^1$H NMR (400 MHz, CDCl$_3$): δ=3.05 (m, 6H), 3.25 (m, 3H), 3.60-3.75 (m, 2H), 3.95 (m, 2H), 4.15 (m, 1H), 4.35 (m, 1H), 6.85 (m, 1H), 7.35 (m, 1H), 7.45 (m, 2H), 7.55 (m, 1H) 7.70 (m, 2H), 8.00 (m, 1H).

Example 35

(E)-1-methyl-2-oxo-1'-(3-(2-(trifluoromethyl)phenyl)acryloyl)spiro[indoline-3,4'-piperidine]-5-carboxamide

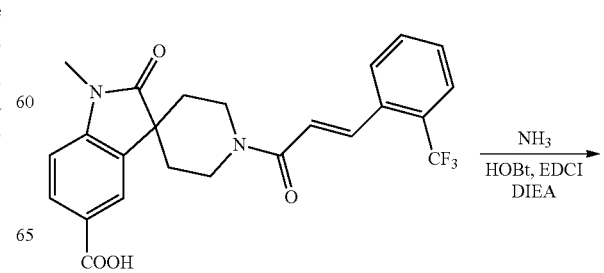

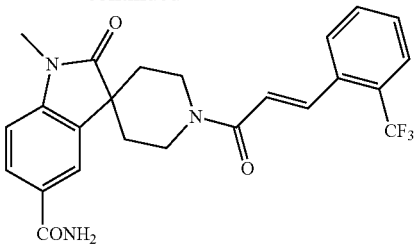

To a solution of (E)-1-methyl-2-oxo-1'-(3-(2-(trifluoromethyl)phenyl)acryloyl)spiro[indoline-3,4'-piperidine]-5-carboxylic acid (15 mg, 0.05 mmol) in anhydrous CH$_2$Cl$_2$ (4 mL) was added HOBt (15 mg, 4 mL), EDCI (22 mg, 0.11 mmol) and DIEA (32 mg, 0.25 mmol) at 0° C. and the mixture was stirred overnight under NH$_3$ at rt. The reaction mixture was washed with 1 N aq HCl and the aqueous phase was extracted with CH$_2$Cl$_2$ (2×). The combined organic phases were dried, filtered and concentrated to give (E)-1-methyl-2-oxo-1'-(3-(2-(trifluoromethyl)phenyl)acryloyl)spiro[indoline-3,4'-piperidine]-5-carboxamide (2.4 mg, 10%). $^1$H NMR (CD$_3$OD): 1.94 (m, 4H), 3.27 (s, 3H), 4.01 (m, 1H), 4.28 (m, 3H), 7.10 (d, 1H), 7.26 (d, 1H), 7.55 (m, 1H), 7.66 (m, 1H), 7.76 (m, 1H), 8.00 (m, 4H).

Example 36

(E)-N-(2-hydroxyethyl)-1-methyl-2-oxo-1'-(3-(2-(trifluoromethyl)phenyl)acryloyl)spiro[indoline-3,4'-piperidine]-5-carboxamide

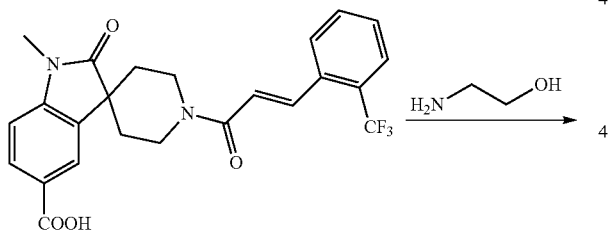

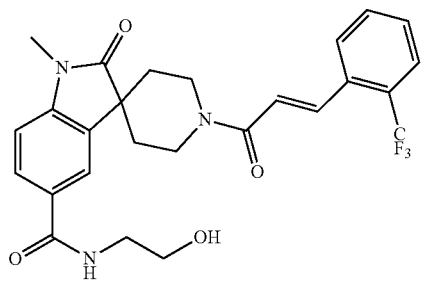

To a solution of (E)-1-methyl-2-oxo-1'-(3-(2-(trifluoromethyl)phenyl)acryloyl)spiro[indoline-3,4'-piperidine]-5-carboxylic acid (20 mg, 0.04 mmol) in anhydrous CH$_2$Cl$_2$ (5 mL) was added 2-aminoethanol (3.6 mg, 0.06 mmol), HOBt (12 mg, 0.09 mmol), EDCI (18 mg, 0.09 mmol) and DIEA (28 mg, 0.22 mol) at 0° C. and the mixture was stirred overnight at rt under N$_2$. The reaction mixture was washed with 1 N aq HCl and water. The organic phase was dried over Na$_2$SO$_4$, filtered and concentrated to afford a residue, which was purified by prep TLC to give (E)-N-(2-hydroxyethyl)-1-methyl-2-oxo-1'-(3-(2-(trifluoromethyl)phenyl)acryloyl)spiro[indoline-3,4'-piperidine]-5-carboxamide (8 mg, 40%). $^1$H NMR (CD$_3$OD): 1.90 (m, 4H), 3.25 (s, 3H), 3.50 (m, 2H), 3.70 (m, 2H), 3.98 (m, 1H), 4.15 (m, 2H), 4.30 (m, 1H), 7.10 (m, 1H), 7.26 (m, 1H), 7.53 (m, 1H), 7.68 (m, 1H), 7.75 (m, 1H), 7.90 (m, 2H), 8.00 (m, 2H).

Example 37

(E)-1-methyl-5-(4-methylpiperazine-1-carbonyl)-1'-(3-(2-(trifluoromethyl)phenyl)acryloyl)spiro[indoline-3,4'-piperidin]-2-one

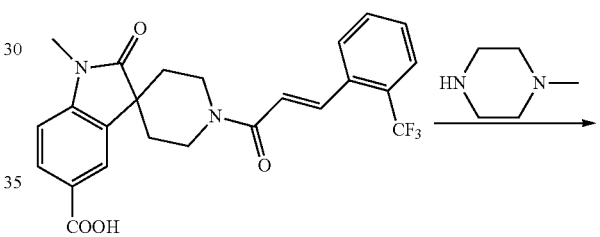

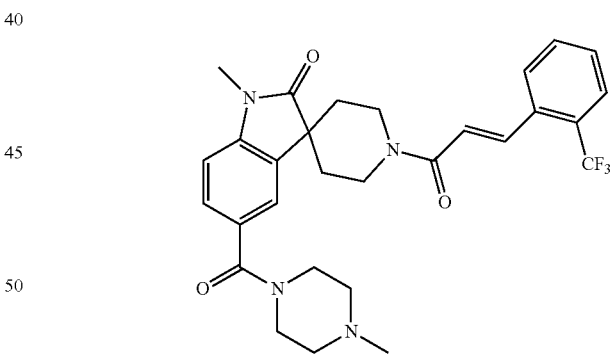

To a solution of (E)-1-methyl-2-oxo-1'-(3-(2-(trifluoromethyl)phenyl)acryloyl)spiro[indoline-3,4'-piperidine]-5-carboxylic acid (20 mg, 0.04 mmol) in anhydrous CH$_2$Cl$_2$ (5 mL) at 0° C. was added 1-methyl-piperazine (6.0 mg, 0.06 mmol), HOBt (12 mg, 0.09 mmol), EDCI (18 mg, 0.09 mmol) and DIEA (28 mg, 0.22 mol) and the mixture was stirred overnight at rt under N$_2$. The reaction mixture was washed with 1 N aq HCl and water. The organic phase was dried over Na$_2$SO$_4$, filtered and concentrated to afford a residue, which was purified by prep TLC to give (E)-1-methyl-5-(4-methylpiperazine-1-carbonyl)-1'-(3-(2-(trifluoromethyl)phenyl)acryloyl)spiro[indoline-3,4'-piperidin]-2-one (12 mg, 57%). $^1$H NMR (CD$_3$OD): 1.90 (m, 4H), 2.95 (s, 3H), 3.30 (m, 11H), 3.95 (m, 1H), 4.20 (m, 2H), 4.30 (m, 1H), 7.10 (m, 1H), 7.26 (m, 1H), 7.50 (m, 3H), 7.66 (m, 1H), 7.77 (m, 1H), 8.00 (m, 2H).

Example 38

(E)-N,1-dimethyl-2-oxo-1'-(3-(2-(trifluoromethyl)phenyl)acryloyl)spiro[indoline-3,4'-piperidine]-5-carboxamide

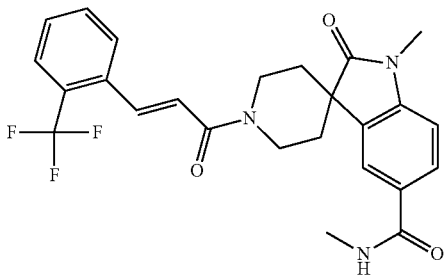 [SMILES: CNC(=O)c1ccc2c(c1)C1(CCN(C(=O)/C=C/c3ccccc3C(F)(F)F)CC1)C(=O)N2C]

The title compound was prepared following a procedure analogous to that described in Example 37 using methylamine hydrochloride. $^1$H NMR: (400 MHz, CDCl$_3$): δ=3.00 (m, 3H), 3.10 (m, 2H), 3.25 (m, 3H), 3.60-3.75 (m, 2H), 4.00 (m, 2H), 4.15 (m, 1H), 4.35 (m, 1H), 6.70 (m, 1H), 6.90 (m, 2H), 7.45 (m, 1H), 7.55 (m, 1H) 7.70 (m, 2H),), 7.85 (m, 2H), 8.00 (m, 1H).

Example 39

(E)-1-methyl-2-oxo-1'-(3-(2-(trifluoromethyl)phenyl)acryloyl)spiro[indoline-3,4'-piperidine]-5-carbonitrile

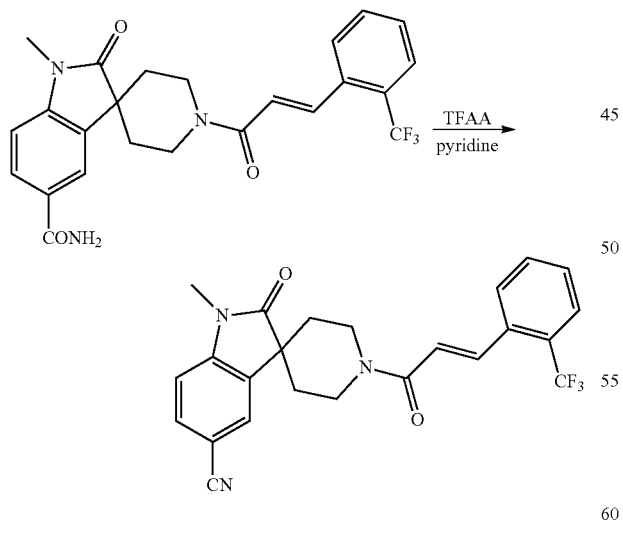

A solution of trifluoroacetic anhydride (34 mg, 0.157 mmol) in dioxane (4 mL) was added dropwise to a stirred, ice-cooled solution of (E)-1-methyl-2-oxo-1'-(3-(2-(trifluoromethyl)phenyl)acryloyl)spiro[indoline-3,4'-piperidine]-5-carboxamide (60 mg, 0.131 mmol) and pyridine (60 mg, 0.262 mmol). The reaction mixture was stirred at rt overnight. The mixture was diluted with water and extracted with EtOAc. The organic layer was dried over Na$_2$SO$_4$ and concentrated to afford the crude product. After purification by preparative HPLC, (E)-1-methyl-2-oxo-1'-(3-(2-(trifluoromethyl) phenyl)acryloyl)spiro[indoline-3,4'-piperidine]-5-carbonitrile was obtained (2.04 mg, 4%). $^1$H NMR: (400 MHz, CDCl$_3$): δ=1.85 (m, 4H), 3.20 (m, 3H), 3.80-3.90 (m, 2H), 4.10 (m, 1H), 4.35 (m, 1H), 6.75 (m, 1H), 6.85 (m, 1H), 7.40 (m, 2H), 7.50 (m, 1H), 7.55 (m, 1H) 7.65 (m, 2H), 7.90 (m, 1H).

Example 40

(E)-methyl 1-ethyl-2-oxo-1'-(3-(2-(trifluoromethyl)phenyl)acryloyl)spiro[indoline-3,4'-piperidine]-5-carboxylate

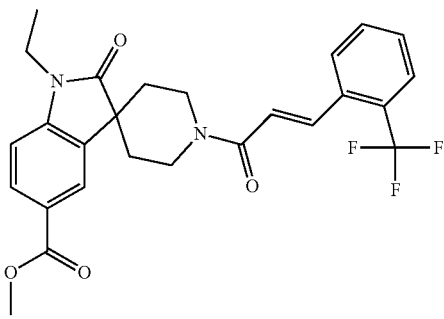 [SMILES: CCN1C(=O)C2(CCN(C(=O)/C=C/c3ccccc3C(F)(F)F)CC2)c2cc(C(=O)OC)ccc21]

The title compound was prepared following a procedure analogous to that described in Example 32 using ethyl iodide in Step 3. $^1$H NMR (CDCl$_3$): 1.25 (m, 3H), 1.86 (m, 4H), 1.82 (m, 2H), 3.77 (m, 2H), 3.91 (s, 3H), 3.96 (m, 2H), 4.14 (m, 1H), 4.38 (m, 1H), 6.84 (m, 2H), 7.42 (m, 1H), 7.54 (m, 1H), 7.69 (m, 2H), 7.92 (m, 1H), 7.98 (m, 2H).

Example 41

(E)-5-fluoro-1'-(3-(2-(trifluoromethyl)phenyl)acryloyl)spiro[indoline-3,4'-piperidin]-2-one

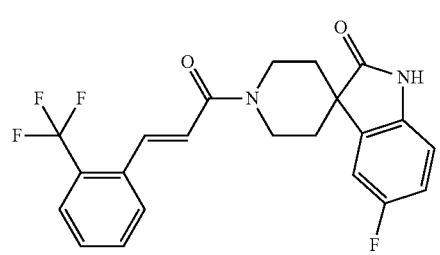 [SMILES: O=C(/C=C/c1ccccc1C(F)(F)F)N1CCC2(CC1)C(=O)Nc1ccc(F)cc12]

The title compound was prepared following a procedure analogous to that described in Example 1 using 5-fluorospiro[indoline-3,4'-piperidin]-2-one. LC-MS Method 1 t$_R$=1.77, min, m/z=419; $^1$H NMR (CDCl$_3$) 1.95 (m, 4H), 3.94 (m, 2H), 4.15 (m, 1H), 4.41 (m, 1H), 6.84 (m, 2H), 6.94 (m, 2H), 7.46 (m, 1H), 7.58 (m, 1H), 7.64 (m, 2H), 7.99 (d, 1H).

Example 42

(E)-1'-(3-(2-(trifluoromethyl)phenyl)acryloyl)-2H-spiro[isoquinoline-1,4'-piperidin]-3(4H)-one

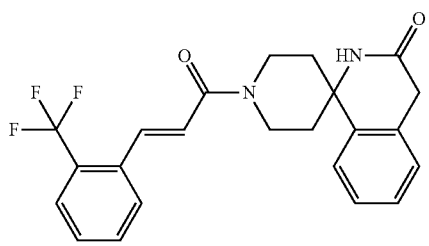 [SMILES: O=C1Cc2ccccc2C2(CCN(C(=O)/C=C/c3ccccc3C(F)(F)F)CC2)N1]

The title compound was prepared following a procedure analogous to that described in Example 1 using 2H-spiro[isoquinoline-1,4'-piperidin]-3(4H)-one. LC-MS Method 1 $t_R$=1.6, min, m/z=415; $^1$H NMR (CDCl$_3$) 1.93 (m, 2H), 2.05-2.30 (3H), 3.16 (m, 1H), 3.62 (m, 1H), 3.70 (s, 2H), 4.14 (m, 1H), 4.84 (m, 1H), 6.83 (d, 1H), 7.19 (m, 1H), 7.29 (s, 2H), 7.48 (m, 1H), 7.58 (m, 2H), 7.69 (m, 2H), 8.00 (d, 1H).

Example 43

(E)-1,1-dimethyl-1'-(3-(2-(trifluoromethyl)phenyl)acryloyl)-1H-spiro[isoquinoline-4,4'-piperidin]-3(2H)-one

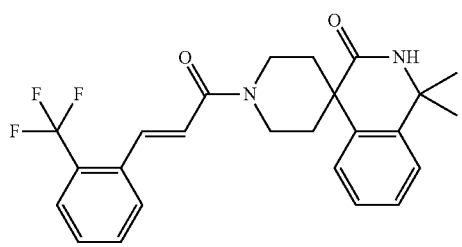 [SMILES: CC1(C)NC(=O)C2(CCN(C(=O)/C=C/c3ccccc3C(F)(F)F)CC2)c2ccccc21]

The title compound was prepared following a procedure analogous to that described in Example 1 using 1,1-dimethyl-1H-spiro[isoquinoline-4,4'-piperidin]-3(2H)-one. LC-MS Method $t_R$=1.78, min, m/z=443; $^1$H NMR (CDCl$_3$) 1.61 (s, 6H), 2.13 (4H), 3.64 (m, 1H), 4.02 (m, 1H), 4.20 (m, 1H), 4.61 (m, 1H), 6.77 (s, 1H), 6.85 (d, 1H), 7.20-7.50 (5H), 7.58 (m, 1H), 7.69 (m, 2H), 7.99 (d, 1H).

Example 44

1-(6-methoxy-3,4-dihydro-2H-spiro[isoquinoline-1,4'-piperidine]-1'-yl)-2-(2-(trifluoromethyl)phenyl)ethanone

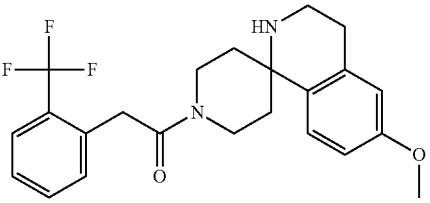 [SMILES: COc1ccc2c(c1)CCNC21CCN(C(=O)Cc2ccccc2C(F)(F)F)CC1]

The title compound was prepared following a procedure analogous to that described in Example 30 using 2-(2-(trifluoromethyl)phenyl)acetic acid. LC-MS Method 1 $t_R$=1.27, min, m/z=419

Example 45

7-chloro-1'-(2-(2-(trifluoromethyl)phenyl)acetyl)spiro[isoindoline-1,4'-piperidin]-3-one

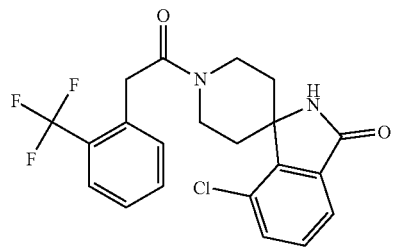 [SMILES: O=C1NC2(CCN(C(=O)Cc3ccccc3C(F)(F)F)CC2)c2c(Cl)cccc21]

The title compound was prepared following a procedure analogous to that described in Example 28 using 2-(2-(trifluoromethyl)phenyl)acetic acid. LC-MS Method 1 $t_R$=1.63, min, m/z=425, 423

Example 46

(±)-1-(3-amino-7-bromo-2,3-dihydrospiro[indene-1,4'-piperidine]-1'-yl)-2-(2-(trifluoromethyl)phenyl)ethanone

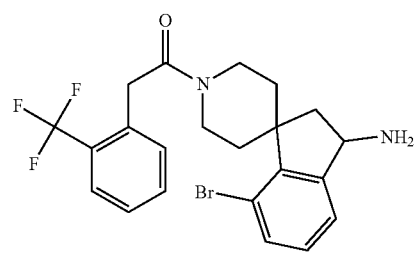 [SMILES: NC1CC2(CCN(C(=O)Cc3ccccc3C(F)(F)F)CC2)c2c(Br)cccc21]

The title compound was prepared following a procedure analogous to that described in Example 18 using 2-(2-(trifluoromethyl)phenyl)acetic acid in Step 4. LC-MS Method 1 $t_R$=1.35, min, m/z=469, 467

Example 47

1'-(2-(2-(trifluoromethyl)phenyl)acetyl)spiro[indoline-3,4'-piperidin]-2-one

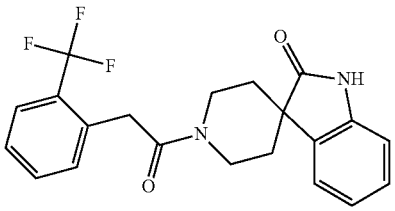 [SMILES: O=C(Cc1ccccc1C(F)(F)F)N1CCC2(CC1)C(=O)Nc1ccccc12]

The title compound was prepared following a procedure analogous to that described in Example 31 using 2-(2-(trifluoromethyl)phenyl)acetic acid and spiro[indoline-3,4'-piperidin]-2-one. LC-MS Method 3 $t_R$=1.089, min, m/z=389; NMR (CDCl$_3$) 1.19 (m, 1H), 1.28 (m, 1H), 1.75 (m, 4H), 3.62 (m, 1H), 3.88 (m, 5H), 6.81 (d, 2H), 6.93 (m, 1H), 7.13 (m, 2H), 7.35 (m, 2H), 7.47 (m, 1H), 7.61 (d, 1H), 8.41 (s, 1H)

Example 48

1-methyl-1'-(2-(2-(trifluoromethyl)phenyl)acetyl)spiro[indoline-3,4'-piperidin]-2-one

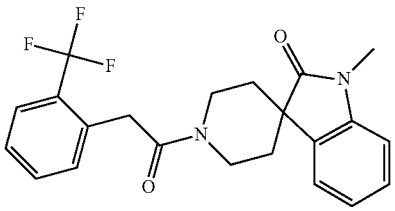 [SMILES: CN1C(=O)C2(CCN(C(=O)Cc3ccccc3C(F)(F)F)CC2)c2ccccc21]

The title compound was prepared following a procedure analogous to that described in Example 31 using 2-(2-(trifluoromethyl)phenyl)acetic acid. LC-MS Method 3 $t_R$=1.199, min, m/z=403; $^1$H NMR (CDCl$_3$) 1.68-1.82 (m, 4H), 3.14 (s, 3H), 3.65 (d, 1H), 3.75 (m, 1H), 4.0 (m, 3H), 4.28 (d, 1H), 6.70 (d, 1H), 7.02 (t, 1H), 7.12 (d, 1H), 7.25 (t, 1H), 7.33 (d, 2H), 7.50 (t, 1H), 7.62 (d, 1H).

Example 49

7-bromo-1'-(2-(2-(trifluoromethyl)phenyl)acetyl)spiro[isoindoline-1,4'-piperidin]-3-one

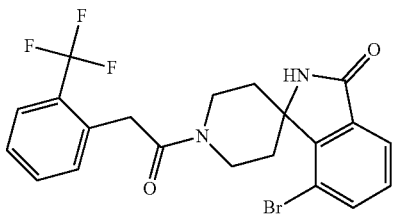 [SMILES: O=C1NC2(CCN(C(=O)Cc3ccccc3C(F)(F)F)CC2)c2c(Br)cccc21]

The title compound was prepared following a procedure analogous to that described in Example 31 using 2-(2-(trifluoromethyl)phenyl)acetic acid and 7-bromospiro[isoindoline-1,4'-piperidin]-3-one. LC-MS Method 2 $t_R$=2.092, min, m/z=469; $^1$H NMR (CDCl$_3$) 1.35 (d, 1H), 1.43 (d, 1H), 2.72 (m, 1H), 2.90 (m, 2H), 3.40 (t, 1H), 3.80-4.05 (m, 3H), 4.88 (d, 1H), 7.31 (t, 2H), 7.38 (d, 1H), 7.48 (t, 1H), 7.61 (d, 1H), 7.68 (d, 1H), 7.78 (d, 1H), 9.17 (s, 1H).

Example 50

5,7-dichloro-1'-(2-(2-(trifluoromethyl)phenyl)acetyl)spiro[isoindoline-1,4'-piperidin]-3-one

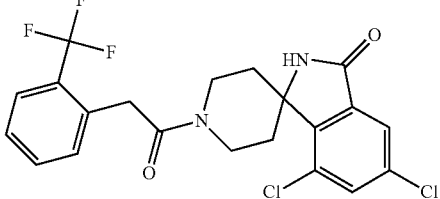

The title compound was prepared following a procedure analogous to that described in Example 31 using 2-(2-(trifluoromethyl)phenyl)acetic acid and 5,7-dichlorospiro[isoindoline-1,4'-piperidin]-3-one. LC-MS Method 3 $t_R$=1.246, min, m/z=457; $^1$H NMR (CDCl$_3$) 1.43 (d, 2H), 2.62 (m, 1H), 2.78 (m, 1H), 2.90 (t, 1H), 3.40 (t, 1H), 3.88-4.11 (m, 3H), 4.93 (d, 1H), 7.43 (m, 2H), 7.54 (m, 2H), 7.70 (d, 1H), 7.77 (s, 1H), 8.74 (s, 1H)

Example 51

2-(7-chloro-1'(2-(2-(trifluoromethyl)phenyl)acetyl)-2,3-dihydrospiro[indene-1,4'-piperidine]-3-yl)acetic acid

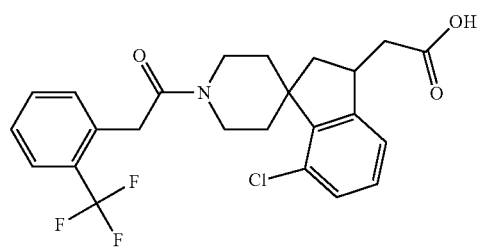 [SMILES: O=C(O)CC1CC2(CCN(C(=O)Cc3ccccc3C(F)(F)F)CC2)c2c(Cl)cccc21]

The title compound was prepared following a procedure analogous to that described in Example 1 using 2-(2-(trifluoromethyl)phenyl)acetic acid and ethyl 2-(7-chloro-2,3-dihydrospiro[indene-1,4'-piperidine]-3-yl)acetate. LC-MS Method 1 $t_R$=1.83, min, m/z=468, 466

Example 52

2-(7-chloro-1'-(2-(2-(trifluoromethoxy)phenyl)acetyl)-2,3-dihydrospiro[indene-1,4'-piperidine]-3-yl)acetic acid

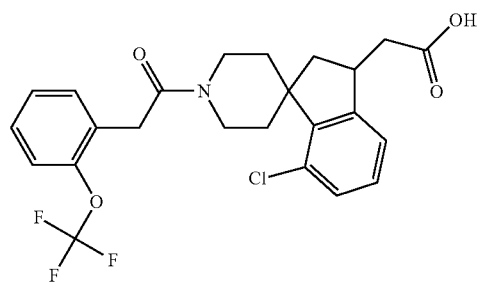 [SMILES: O=C(O)CC1CC2(CCN(C(=O)Cc3ccccc3OC(F)(F)F)CC2)c2c(Cl)cccc21]

The title compound was prepared following a procedure analogous to that described in Example 1 2-(2-(trifluoromethoxy)phenyl)acetic acid and ethyl 2-(7-chloro-2,3-dihydrospiro[indene-1,4'-piperidine]-3-yl)acetate. LC-MS Method 1 $t_R$=1.88, min, m/z=484, 482

Example 53

2-(7-chloro-1'(2-(4-fluoro-2-(trifluoromethyl)phenyl)acetyl)-2,3-dihydrospiro[indene-1,4'-piperidine]-3-yl)acetic acid

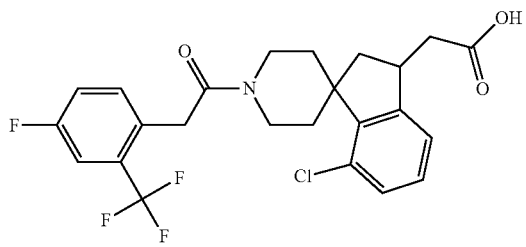 [SMILES: O=C(O)CC1CC2(CCN(C(=O)Cc3ccc(F)cc3C(F)(F)F)CC2)c2c(Cl)cccc21]

The title compound was prepared following a procedure analogous to that described in Example 1 using 2-(4-fluoro-2-(trifluoromethyl)phenyl)acetic acid and ethyl 2-(7-chloro-2,3-dihydrospiro[indene-1,4'-piperidine]-3-yl)acetate. LC-MS Method 1 $t_R$=1.88, min, m/z=486, 484

Example 54

2-(7-chloro-1'(2-(4-chloro-2-(trifluoromethyl)phenyl)acetyl)-2,3-dihydrospiro[indene-1,4'-piperidine]-3-yl)acetic acid

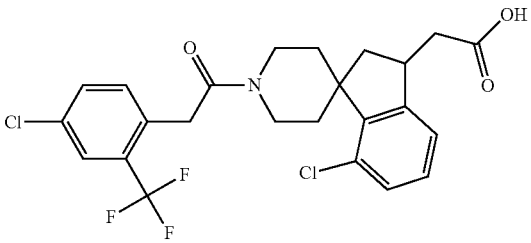 [SMILES: O=C(O)CC1CC2(CCN(C(=O)Cc3ccc(Cl)cc3C(F)(F)F)CC2)c2c(Cl)cccc21]

The title compound was prepared following a procedure analogous to that described in Example 1 using 2-(4-chloro-2-(trifluoromethyl)phenyl)acetic acid and ethyl 2-(7-chloro- 2,3-dihydrospiro[indene-1,4'-piperidine]-3-yl)acetate. LC-MS Method 1 $t_R$=2.00, min, m/z=500.

Example 55

2-methyl-1'-(3-(2-(trifluoromethyl)phenyl)propanoyl)spiro[isoindoline-1,4'-piperidin]-3-one

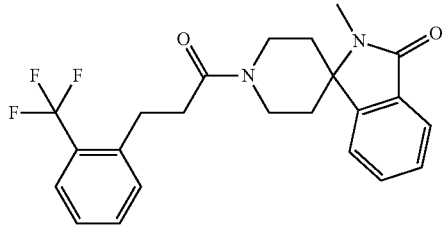 [SMILES: CN1C(=O)c2ccccc2C12CCN(C(=O)CCc1ccccc1C(F)(F)F)CC2]

The title compound was prepared following a procedure analogous to that described in Example 1 using 3-(2-(trifluoromethyl)phenyl)propanoic acid and 2-methylspiro[isoindoline-1,4'-piperidin]-3-one. LC-MS Method 1 $t_R$=1.65, min, m/z=417, 415.

Example 56

Ethyl 2-(7-bromo-1'-(3-(2-(trifluoromethyl)phenyl)propanoyl)-2,3-dihydrospiro[indene-1,4'-piperidine]-3-yl)acetate

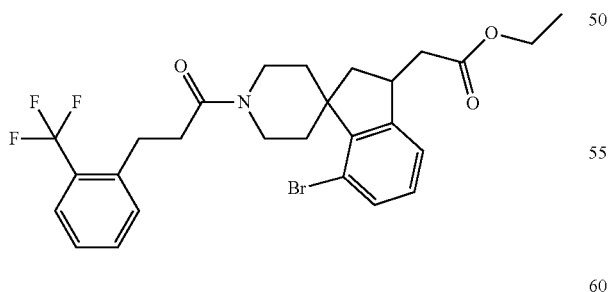

The title compound was prepared following a procedure analogous to that described in Example 1 using 3-(2-(trifluoromethyl)phenyl)propanoic acid and ethyl 2-(7-bromo-2,3-dihydrospiro[indene-1,4'-piperidine]-3-yl)acetate. LC-MS Method 1 $t_R$=2.27, min, m/z=554, 552

Example 57 tert-butyl 1'-(3-(2-(trifluoromethyl)phenyl)propanoyl)-1H-spiro[isoquinoline-4,4'-piperidine]-2(3H)-carboxylate

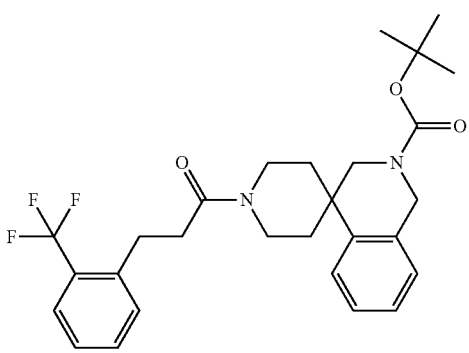 [SMILES: CC(C)(C)OC(=O)N1Cc2ccccc2C2(CCN(C(=O)CCc3ccccc3C(F)(F)F)CC2)C1]

The title compound was prepared following a procedure analogous to that described in Example 1 using 3-(2-(trifluoromethyl)phenyl)propanoic acid and tert-butyl 1H-spiro[isoquinoline-4,4'-piperidine]-2(3H)-carboxylate. LC-MS Method 1 $t_R$=2.18, min, m/z=503

Example 58

2-(7-bromo-1'-(3-(2-(trifluoromethyl)phenyl)propanoyl)-2,3-dihydrospiro[indene-1,4'-piperidine]-3-yl)acetic acid

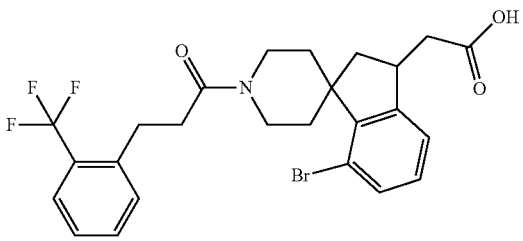 [SMILES: O=C(O)CC1CC2(CCN(C(=O)CCc3ccccc3C(F)(F)F)CC2)c2c(Br)cccc21]

The title compound was prepared from ethyl 2-(7-bromo-1'-(3-(2-(trifluoromethyl)phenyl)propanoyl)-2,3-dihydrospiro[indene-1,4'-piperidine]-3-yl)acetate following a procedure analogous to that described in Example 2. LC-MS Method 1 $t_R$=1.95, min, m/z=526, 524

Example 59

1-(2,3-dihydro-1H-spiro[isoquinoline-4,4'-piperidine]-1'-yl)-3-(2-(trifluoromethyl)phenyl)propan-1-one

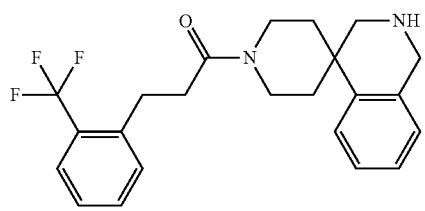 [SMILES: O=C(CCc1ccccc1C(F)(F)F)N1CCC2(CC1)CNCc1ccccc12]

The title compound was prepared from tert-butyl 1'-(3-(2-(trifluoromethyl)phenyl)propanoyl)-1H-spiro[isoquinoline-4,4'-piperidine]-2(3H)-carboxylate following a procedure analogous to that described in Example 21. LC-MS Method 1 $t_R$=1.32, min, m/z=403

Example 60

1-(2-(methylsulfonyl)-2,3-dihydro-1H-spiro[isoquinoline-4,4'-piperidine]-1'-yl)-3-(2-(trifluoromethyl)phenyl)propan-1-one

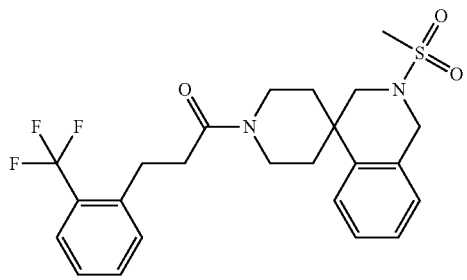 [SMILES: CS(=O)(=O)N1Cc2ccccc2C2(CCN(C(=O)CCc3ccccc3C(F)(F)F)CC2)C1]

The title compound was prepared from 1-(2,3-dihydro-1H-spiro[isoquinoline-4,4'-piperidine]-1'-yl)-3-(2-(trifluoromethyl)phenyl)propan-1-one following a procedure analogous to that described in Example 22. LC-MS Method 1 $t_R$=1.78, min, m/z=481

Example 61

7-chloro-2-methyl-1'-(3-(2-(trifluoromethyl)phenyl)propanoyl)spiro[isoindoline-1,4'-piperidin]-3-one

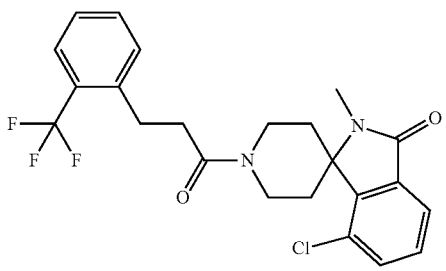 [SMILES: CN1C(=O)c2cccc(Cl)c2C12CCN(C(=O)CCc1ccccc1C(F)(F)F)CC2]

The title compound was prepared following a procedure analogous to that described in Example 1 using 3-(2-(trifluoromethyl)phenyl)propanoic acid and 7-chloro-2-methylspiro[isoindoline-1,4'-piperidin]-3-one. LC-MS Method 1 $t_R$=1.77, min, m/z=453, 451

Example 62

1-(6-methoxy-3,4-dihydro-2H-spiro[isoquinoline-1,4'-piperidine]-1'-yl)-3-(2-(trifluoromethyl)phenyl)propan-1-one

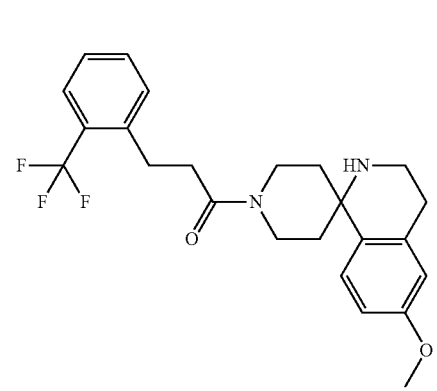 [SMILES: COc1ccc2c(c1)CCNC21CCN(C(=O)CCc2ccccc2C(F)(F)F)CC1]

The title compound was prepared following a procedure analogous to that described in Example 30 using 3-(2-(trifluoromethyl)phenyl)propanoic acid. LC-MS Method 1 $t_R$=1.32, min, m/z=433

Example 63

1-(6-methoxy-3,4-dihydro-2H-spiro[isoquinoline-1,4'-piperidine]-1'-yl)-3-o-tolylpropane-1-one

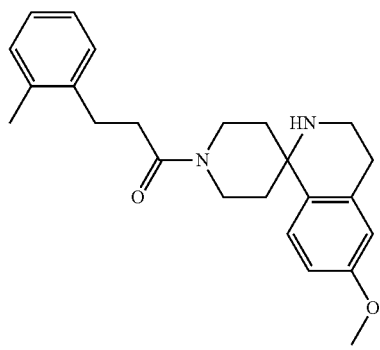 [SMILES: COc1ccc2c(c1)CCNC21CCN(C(=O)CCc2ccccc2C)CC1]

The title compound was prepared following a procedure analogous to that described in Example 30 using 3-o-tolylpropanoic acid. LC-MS Method 1 $t_R$=1.23, min, m/z=379

Example 64

1-(7-bromo-3-hydroxy-2,3-dihydrospiro[indene-1,4'-piperidine]-1'-yl)-3-(2-(trifluoromethyl)phenyl)propan-1-one

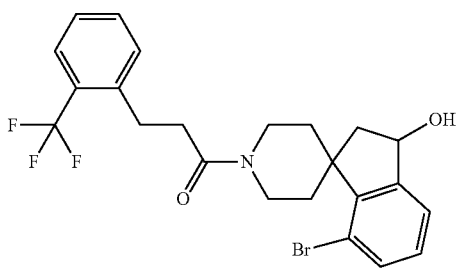 [SMILES: O=C(CCc1ccccc1C(F)(F)F)N1CCC2(CC1)CC(O)c1cccc(Br)c12]

The title compound was prepared from 7-bromo-1'-(3-(2-(trifluoromethyl)phenyl)propanoyl)spiro[indene-1,4'-piperidin]-3(2H)-one following a procedure analogous to that described in Example 16. LC-MS Method 1 $t_R$=1.87, min, m/z=484, 482

Example 65

7-chloro-1'-(3-(2-(trifluoromethyl)phenyl)propanoyl)spiro[isoindoline-1,4'-piperidin]-3-one

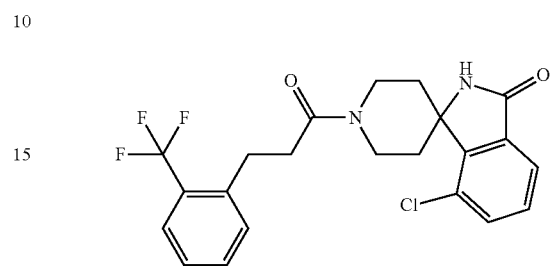

The title compound was prepared following a procedure analogous to that described in Example 1 using 3-(2-(trifluoromethyl)phenyl)propanoic acid and 7-chlorospiro[isoindoline-1,4'-piperidin]-3-one. LC-MS Method 1 $t_R$=1.73, min, m/z=437

Example 66

1-(3-amino-7-bromo-2,3-dihydrospiro[indene-1,4'-piperidine]-1'-yl)-3-(2-(trifluoromethyl)phenyl)propan-1-one

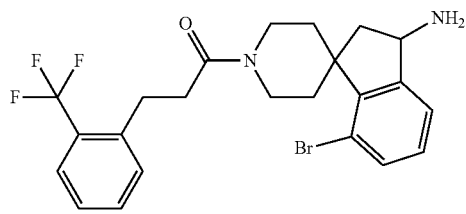 [SMILES: NC1CC2(CCN(C(=O)CCc3ccccc3C(F)(F)F)CC2)c2c(Br)cccc21]

The title compound was prepared following a procedure analogous to that described in Example 18 using 3-(2-(trifluoromethyl)phenyl)propanoic acid in Step 4. LC-MS Method 1 $t_R$=1.4, min, m/z=483, 481

Example 67

1'-(3-(2-(trifluoromethyl)phenyl)propanoyl)spiro[indoline-3,4'-piperidin]-2-one

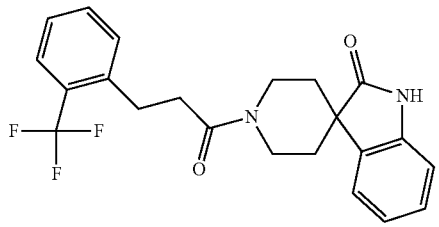 [SMILES: O=C(CCc1ccccc1C(F)(F)F)N1CCC2(CC1)C(=O)Nc1ccccc12]

The title compound was prepared following a procedure analogous to that described in Example 31 using 3-(2-(trifluoromethyl)phenyl)propanoic acid and spiro[indoline-3,4'-piperidin]-2-one. LC-MS Method 3 $t_R$=1.157, min, m/z=403; $^1$H NMR (CDCl$_3$) 1.39 (m, 2H), 1.47 (m, 2H), 1.65 (m, 2H), 1.78 (m, 3H), 2.62 (m, 2H), 3.15 (m, 2H), 3.61 (m, 2H), 3.83 (m, 2H), 4.17 (m, 1H), 6.83 (d, 1H), 6.97 (m, 1H), 7.15 (m, 2H), 7.26 (m, 1H), 7.38 (m, 1H), 7.43 (m, 1H), 7.58 (d, 1H), 7.84 (s, 1H).

Example 68

N-methyl-1'-(3-(2-(trifluoromethyl)phenyl)propanoyl)-1H-spiro[isoquinoline-4,4'-piperidine]-2(3H)-carboxamide

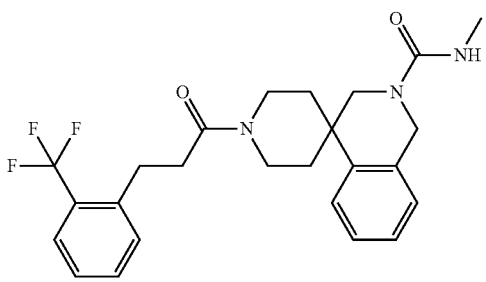 [SMILES: CNC(=O)N1Cc2ccccc2C2(CCN(C(=O)CCc3ccccc3C(F)(F)F)CC2)C1]

The title compound was prepared from 1-(2,3-dihydro-1H-spiro[isoquinoline-4,4'-piperidine]-1'-yl)-3-(2-(trifluoromethyl)phenyl)propan-1-one following a procedure analogous to that described in Example 19. LC-MS Method 1 $t_R$=1.72, min, m/z=460

Example 69

1-methyl-1'-(3-(2-(trifluoromethyl)phenyl)propanoyl)spiro[indoline-3,4'-piperidin]-2-one

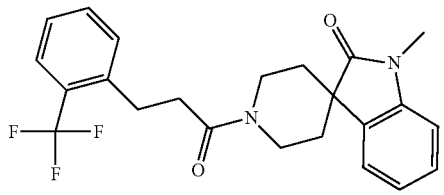 [SMILES: CN1C(=O)C2(CCN(C(=O)CCc3ccccc3C(F)(F)F)CC2)c2ccccc21]

The title compound was prepared following a procedure analogous to that described in Example 31 using 3-(2-(trifluoromethyl)phenyl)propanoic acid. LC-MS Method 3 $t_R$=1.262, min, m/z=417; $^1$H NMR (CDCl$_3$) 1.62 (m, 1H), 1.75 (m, 2H), 2.62 (m, 2H), 3.15 (s, 5H), 3.58 (m, 1H), 3.72-3.92 (m, 2H), 4.18 (m, 1H), 6.80 (d, 1H), 7.0 (t, 1H), 7.17 (d, 1H), 7.25 (m, 2H), 7.38-7.48 (m, 2H), 7.58 (d, 1H).

Example 70

(S)-2-(7-bromo-1'-(3-(2-(trifluoromethyl)phenyl)propanoyl)-2,3-dihydrospiro[indene-1,4'-piperidine]-3-yl)acetic acid

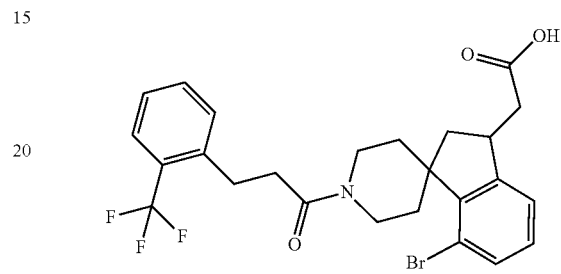

Isomers 1 and 2 of the title compound were prepared following a procedure analogous to that described for Example 2 Isomers 1 and 2 using 3-(2-(trifluoromethyl)phenyl)propanoic acid in Step 2.

Isomer 1: LC-MS Method 3 $t_R$=1.334, min, m/z=526; $^1$H NMR (CDCl$_3$) 1.48 (d, 2H), 1.62 (m, 1H), 2.31 (m, 1H), 2.43 (m, 1H), 2.50-2.80 (m, 4H), 2.88-3.20 (m, 5H), 3.52 (m, 1H), 3.75 (d, 1H), 4.68 (d, 1H), 7.0 (t, 1H), 7.08 (d, 1H), 7.25 (t, 1H), 7.31 (d, 1H), 7.40 (m, 2H), 7.56 (d, 1H).

Isomer 2: LC-MS Method 3 $t_R$=1.346, min, m/z=526; $^1$H NMR (CDCl$_3$) 1.48 (d, 2H), 1.70 (m, 1H), 2.30-2.60 (m, 2H), 2.62-2.88 (m, 4H), 2.95-3.30 (m, 5H), 3.60 (m, 1H), 3.82 (d, 1H), 4.73 (d, 1H), 7.10 (t, 1H), 7.13 (d, 1H), 7.32 (t, 1H), 7.45 (m, 3H), 7.65 (d, 1H).

Example 71

7-bromo-1'-(3-(2-(trifluoromethyl)phenyl)propanoyl)spiro[isoindoline-1,4'-piperidin]-3-one

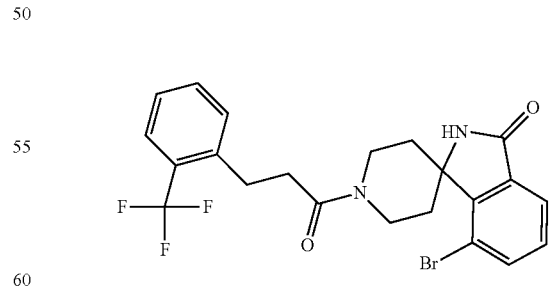

The title compound was prepared following a procedure analogous to that described in Example 28 using 3-(2-(trifluoromethyl)phenyl)propanoic acid and 7-bromospiro[isoindoline-1,4'-piperidin]-3-one. LC-MS Method 2 $t_R$=2.206, min, m/z=481; $^1$H NMR (CDCl$_3$) 1.43 (d, 2H), 2.68 (t, 2H), 2.80-2.92 (m, 3H), 3.15 (t, 2H), 3.32 (t, 1H), 3.92 (d, 1H), 4.85 (d, 1H), 7.25 (m, 2H), 7.40 (m, 2H), 7.56 (d, 1H), 7.65 (d, 1H), 7.79 (d, 1H), 9.20 (s, 1H).

Example 72

5,7-dichloro-1'-(3-(2-(trifluoromethyl)phenyl)propanoyl)spiro[isoindoline-1,4'-piperidin]-3-one

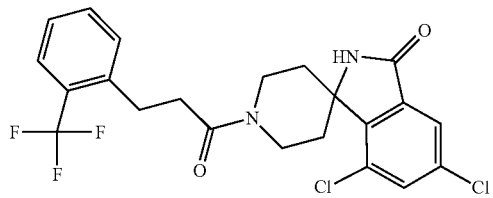 [SMILES: O=C1NC2(CCN(C(=O)CCc3ccccc3C(F)(F)F)CC2)c2c(Cl)cc(Cl)cc21]

The title compound was prepared following a procedure analogous to that described in Example 28 using 3-(2-(trifluoromethyl)phenyl)propanoic acid and 5,7-dichlorospiro[isoindoline-1,4'-piperidin]-3-one. LC-MS Method 3 $t_R$=1.312, min, m/z=471; $^1$H NMR (d$_6$-DMSO) 1.38 (d, 2H), 2.37 (m, 1H), 2.60-2.80 (m, 2H), 2.83-3.02 (m, 3H), 3.35 (m, 2H), 3.94 (d, 1H), 4.51 (d, 1H), 7.38 (t, 1H), 7.55 (m, 2H), 7.64 (m, 2H), 7.80 (s, 1H), 9.88 (s, 1H)

Example 73

2-(7-chloro-1'-(3-(2-(trifluoromethyl)phenyl)propanoyl)-2,3-dihydrospiro[indene-1,4'-piperidine]-3-yl)acetic acid

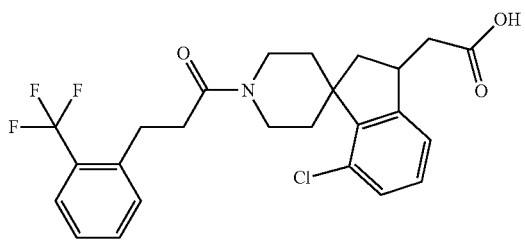 [SMILES: O=C(O)CC1CC2(CCN(C(=O)CCc3ccccc3C(F)(F)F)CC2)c2c(Cl)cccc21]

The title compound was prepared following a procedure analogous to that described in Example 1 using 3-(2-(trifluoromethyl)phenyl)propanoic acid and ethyl 2-(7-chloro-2,3-dihydrospiro[indene-1,4'-piperidine]-3-yl)acetate followed by a procedure analogous to that in Example 2. LC-MS Method 1 $t_R$=1.93, min, m/z=482, 480

Example 74

2-(7-chloro-1'-(3-(2-chlorophenyl)propanoyl)-2,3-dihydrospiro[indene-1,4'-piperidine]-3-yl)acetic acid

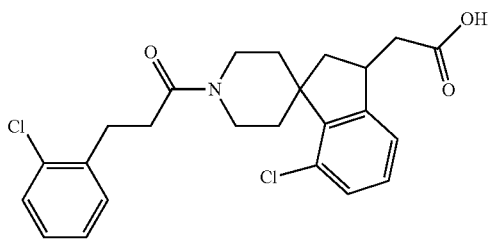 [SMILES: O=C(O)CC1CC2(CCN(C(=O)CCc3ccccc3Cl)CC2)c2c(Cl)cccc21]

The title compound was prepared following a procedure analogous to that described in Example 1 using 3-(2-chlorophenyl)propanoic acid and ethyl 2-(7-chloro-2,3-dihydrospiro[indene-1,4'-piperidine]-3-yl)acetate followed by a procedure analogous to that in Example 2. LC-MS Method 1 $t_R$=1.87, min, m/z=446

Example 75

2-(7-chloro-1'-(3-(2,4-dichlorophenyl)propanoyl)-2,3-dihydrospiro[indene-1,4'-piperidine]-3-yl)acetic acid

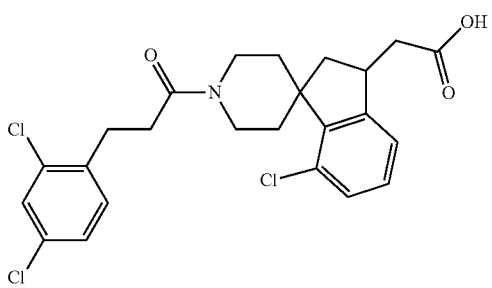 [SMILES: O=C(O)CC1CC2(CCN(C(=O)CCc3ccc(Cl)cc3Cl)CC2)c2c(Cl)cccc21]

The title compound was prepared following a procedure analogous to that described in Example 1 using 3-(2,4-dichlorophenyl)propanoic acid and ethyl 2-(7-chloro-2,3-dihydrospiro[indene-1,4'-piperidine]-3-yl)acetate followed by a procedure analogous to that in Example 2. LC-MS Method 1 t$_R$=2.03, min, m/z=484, 482, 480

3.83 (m, 1H), 3.98 (m, 2H), 4.20 (m, 1H), 7.11 (d, 1H), 7.45 (t, 1H), 7.55 (d, 1H), 7.64 (t, 1H), 7.71 (d, 1H), 7.95 (m, 2H).

Example 76

1-methyl-2-oxo-1'-(3-(2-(trifluoromethyl)phenyl)propanoyl)spiro[indoline-3,4'-piperidine]-5-carboxylate

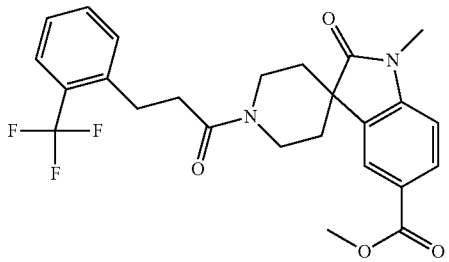 [SMILES: COC(=O)c1ccc2c(c1)C1(CCN(C(=O)CCc3ccccc3C(F)(F)F)CC1)C(=O)N2C]

The title compound was prepared following a procedure analogous to that described in Example 32 using 3-(2-(trifluoromethyl)phenyl)propanoic acid in Step 2. LC-MS Method 3 t$_R$=1.257, min, m/z=475; $^1$H NMR (CDCl$_3$) 1.63 (m, 2H), 1.70-1.82 (m, 3H), 2.70 (m, 2H), 3.24 (m, 5H), 3.65 (m, 1H), 3.81 (m, 1H), 3.93 (m, 4H), 4.28 (m, 1H), 6.89 (d, 1H), 7.37 (t, 1H), 7.46 (d, 1H), 7.53 (t, 1H), 7.65 (d, 1H), 7.88 (s, 1H), 8.05 (d, 1H).

Example 77

1-methyl-2-oxo-1'-(3-(2-(trifluoromethyl)phenyl)propanoyl)spiro[indoline-3,4'-piperidine]-5-carboxamide

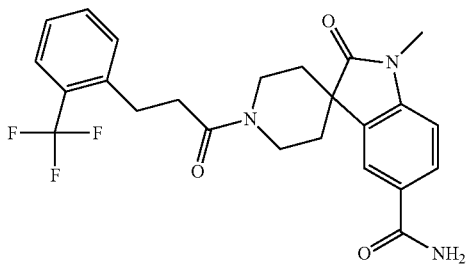 [SMILES: CN1C(=O)C2(CCN(C(=O)CCc3ccccc3C(F)(F)F)CC2)c2cc(C(N)=O)ccc21]

The title compound was prepared from 1-methyl-2-oxo-1'-(3-(2-(trifluoromethyl)phenyl)propanoyl)spiro[indoline-3,4'-piperidine]-5-carboxylate following a procedure analogous to those described in Examples 33 and 35. LC-MS Method 2 t$_R$=2.022, min, m/z=482; $^1$H NMR (CD$_3$OD) 1.78 (m, 2H), 1.84 (m, 2H), 2.83 (m, 2H), 3.20 (t, 2H), 3.28 (s, 3H),

Example 78

Methyl 1-ethyl-2-oxo-1'-(3-(2-(trifluoromethyl)phenyl)propanoyl)spiro[indoline-3,4'-piperidine]-5-carboxylate

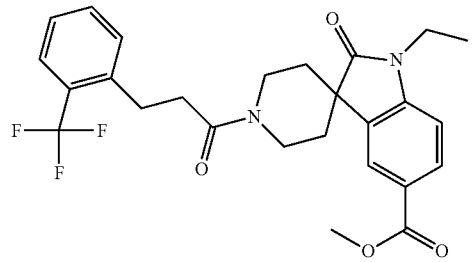 [SMILES: CCN1C(=O)C2(CCN(C(=O)CCc3ccccc3C(F)(F)F)CC2)c2cc(C(=O)OC)ccc21]

The title compound was prepared following a procedure analogous to that described in Example 32 using 3-(2-(trifluoromethyl)phenyl)propanoic acid in Step 2 and ethyl iodide in Step 3. LC-MS Method 3 t$_R$=1.327, min, m/z=511.1; $^1$H NMR (CD$_3$OD) 1.24 (m, 3H), 1.60-1.75 (m, 2H), 1.80 (m, 2H), 2.75 (m, 1H), 2.85 (m, 1H), 3.19 (t, 2H), 3.78 (m, 4H), 3.91 (s, 1H), 4.21 (m, 1H), 4.58 (s, 1H), 7.12 (d, 1H), 7.44 (t, 1H), 7.54 (d, 1H), 7.63 (t, 1H), 7.69 (d, 1H), 7.94 (s, 1H), 8.04 (d, 1H)

Example 79

1-methyl-2-oxo-1'-(3-(2-(trifluoromethyl)phenyl)propanoyl)spiro[indoline-3,4'-piperidine]-5-carbonitrile

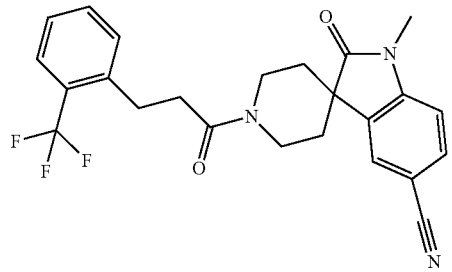 [SMILES: CN1C(=O)C2(CCN(C(=O)CCc3ccccc3C(F)(F)F)CC2)c2cc(C#N)ccc21]

The title compound was prepared from 1-methyl-2-oxo-1'-(3-(2-(trifluoromethyl)phenyl)propanoyl)spiro[indoline-3,4'-piperidine]-5-carboxamide following a procedure analogous to that described in Example 39. LC-MS Method 3 t$_R$=1.219, min, m/z=442.1; $^1$H NMR (CDCl$_3$) 1.62 (m, 1H), 1.80 (m, 3H), 2.76 (m, 2H), 3.18 (m, 2H), 3.22 (s, 3H), 3.65

(m, 1H), 3.78 (m, 1H), 3.94 (m, 1H), 4.32 (m, 1H), 6.90 (d, 1H), 7.40 (m, 3H), 7.53 (t, 1H), 7.63 (t, 2H)

Example 80

2-(7-chloro-1'-(3-(2-(trifluoromethyl)phenyl)propanoyl)-2,3-dihydrospiro[indene-1,4'-piperidine]-3-yl)acetamide

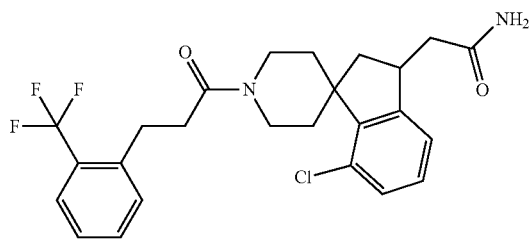 [SMILES: NC(=O)CC1CC2(CCN(C(=O)CCc3ccccc3C(F)(F)F)CC2)c2c(Cl)cccc21]

The title compound was prepared from 2-(7-chloro-1'-(3-(2-(trifluoromethyl)phenyl)propanoyl)-2,3-dihydrospiro[indene-1,4'-piperidine]-3-yl)acetic acid following a procedure analogous to that described in Example 13. LC-MS Method 1 $t_R$=1.78, min, m/z=481, 479.

Example 81

Ethyl 2-(7-bromo-1'4(2-chloro-6-fluorobenzyl)(ethyl)carbamoyl)-2,3-dihydrospiro[indene-1,4'-piperidine]-3-yl)acetate

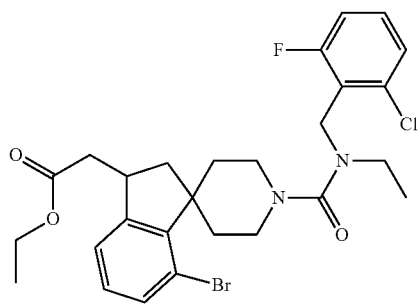 [SMILES: CCOC(=O)CC1CC2(CCN(C(=O)N(CC)Cc3c(F)cccc3Cl)CC2)c2c(Br)cccc21]

LC-MS Method 1 $t_R$=2.33, min, m/z=565.

Example 82

Ethyl 2-(7-bromo-1'-(2-ethoxybenzylcarbamoyl)-2,3-dihydrospiro[indene-1,4'-piperidine]-3-yl)acetate

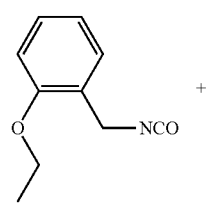

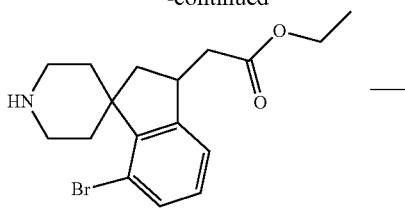

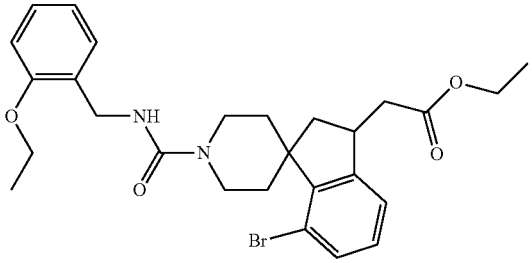

The title compound was prepared following a procedure analogous to that described in Example 19 using 2-ethoxybenzyl isocyanate and ethyl 2-(7-bromo-2,3-dihydrospiro[indene-1,4'-piperidine]-3-yl)acetate. $^1$H NMR (CDCl$_3$) [selected resonances] 1.28 (t, 3H), 1.44 (t, 3H), 4.11 (q, 2H), 4.19 (q, 2H), 4.45 (s, 2H).

Example 83

2-(7-bromo-1'-(2,4,5-trifluorobenzylcarbamoyl)-2,3-dihydrospiro[indene-1,4'-piperidine]-3-yl)acetic acid

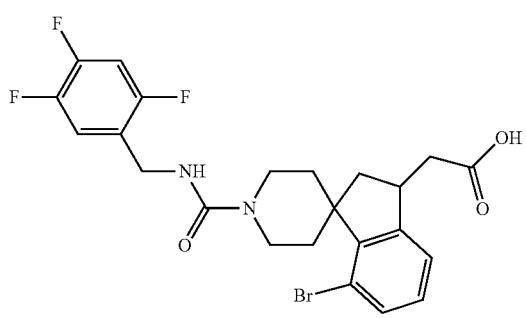 [SMILES: O=C(O)CC1CC2(CCN(C(=O)NCc3cc(F)c(F)cc3F)CC2)c2c(Br)cccc21]

The title compound was prepared following a procedure analogous to that described in Example 82 using 2,4,5-trifluorobenzyl isocyanate followed by a procedure analogous to that described in Example 2. LC-MS Method 1 $t_R$=1.72, min, m/z=513, 511

The title compound was prepared following a procedure analogous to that described in Example 19. LC-MS Method 1 $t_R$=1.95, min, m/z=399.

Example 84

2-(7-bromo-1'-(2-ethoxybenzylcarbamoyl)-2,3-dihydrospiro[indene-1,4'-piperidine]-3-yl)acetic acid

Example 86

Ethyl 2-(7-bromo-1'(2-methylbenzylcarbamoyl)-2,3-dihydrospiro[indene-1,4'-piperidine]-3-yl)acetate

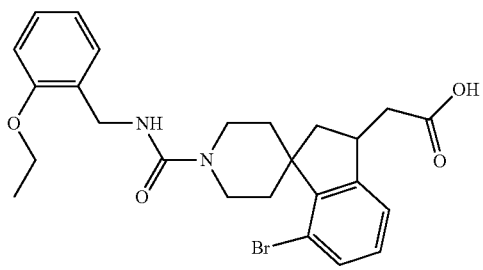 [SMILES: CCOc1ccccc1CNC(=O)N1CCC2(CC1)CC(CC(=O)O)c1cccc(Br)c12]

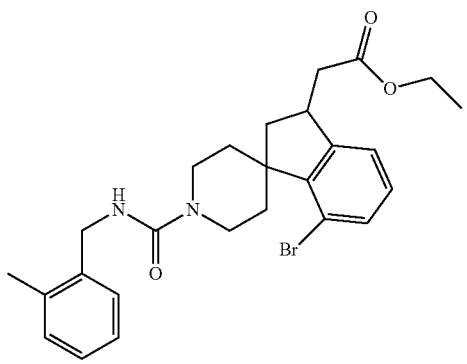 [SMILES: CCOC(=O)CC1CC2(CCN(C(=O)NCc3ccccc3C)CC2)c2c(Br)cccc21]

The title compound was prepared from ethyl 2-(7-bromo-1'-(2-ethoxybenzylcarbamoyl)-2,3-dihydrospiro[indene-1,4'-piperidine]-3-yl)acetate using a procedure analogous to that described in Example 2. LC-MS Method 1 $t_R$=1.77, min, m/z=503, 511

The title compound was prepared following a procedure analogous to that described in Example 82 using 2-methylbenzyl isocyanate. LC-MS Method 1 $t_R$=2.01, min, m/z=499, 501(M+1).

Example 85

N-(biphenyl-2-ylmethyl)-3H-spiro[isobenzofuran-1,4'-piperidine]-1'-carboxamide

Example 87

2-(7-bromo-1'-(2-methylbenzylcarbamoyl)-2,3-dihydrospiro[indene-1,4'-piperidine]-3-yl)acetic acid

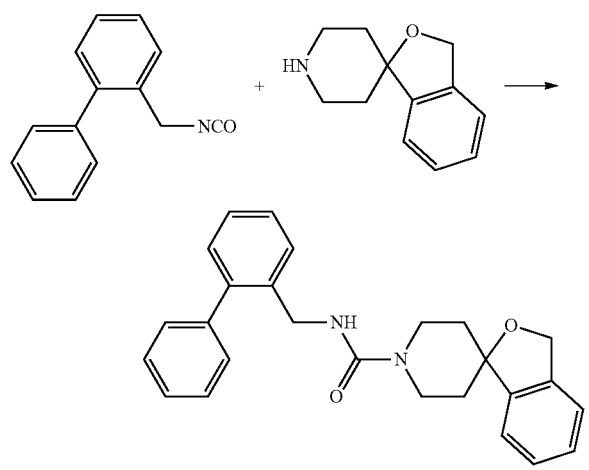

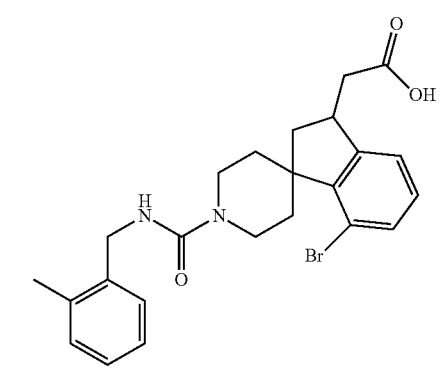 [SMILES: Cc1ccccc1CNC(=O)N1CCC2(CC1)CC(CC(=O)O)c1cccc(Br)c12]

The title compound was prepared from ethyl 2-(7-bromo-1'-(2-methylbenzylcarbamoyl)-2,3-dihydrospiro[indene-1, 4'-piperidine]-3-yl)acetate using a procedure analogous to that described in Example 2. LC-MS Method 1 $t_R$=1.68, min, m/z=471, 473(M+1)

Example 88 tert-butyl 4-(2-(7-bromo-1'-(2-methylbenzylcarbamoyl)-2,3-dihydrospiro[indene-1,4'-piperidine]-3-yl)acetyl)piperazine-1-carboxylate

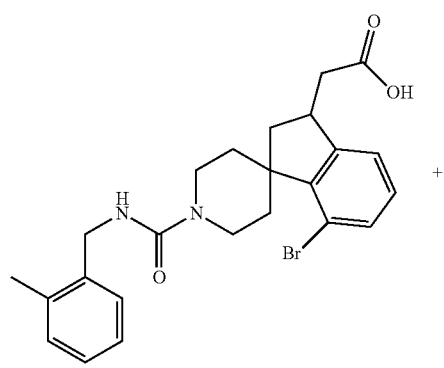

+

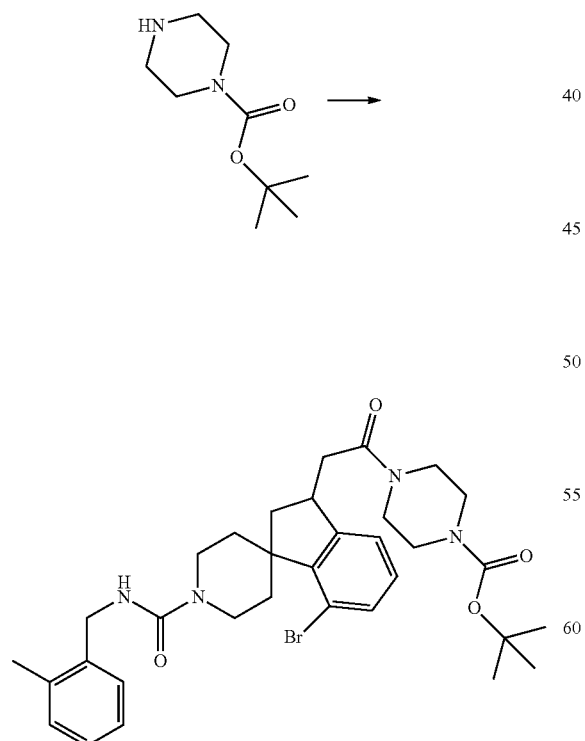

LC-MS Method 1 $t_R$=1.95, min, m/z=639, 641(M+1)

Example 89

Ethyl 2-(7-bromo-1'-(2-chloro-6-methylbenzylcarbamoyl)-2,3-dihydrospiro[indene-1,4'-piperidine]-3-yl)acetate

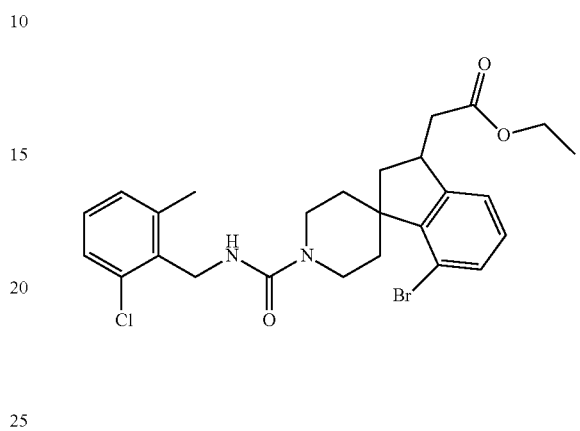

The title compound was prepared following a procedure analogous to that described in Example 82 using 2-chloro-6-methylbenzyl isocyanate. LC-MS Method 1 $t_R$=2.11, min, m/z=533, 535(M+1)

Example 90

7-bromo-N-(2-methylbenzyl)-3-(2-oxo-2-(piperazin-1-yl)ethyl)-2,3-dihydrospiro[indene-1,4'-piperidine]-1'-carboxamide

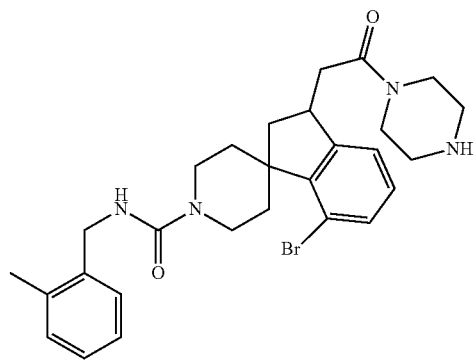 [SMILES: Cc1ccccc1CNC(=O)N1CCC2(CC1)CC(CC(=O)N1CCNCC1)c1cccc(Br)c12]

The title compound was prepared from tert-butyl 4-(2-(7-bromo-1'-(2-methylbenzylcarbamoyl)-2,3-dihydrospiro[indene-1,4'-piperidine]-3-yl)acetyl)piperazine-1-carboxylate using a procedure analogous to that described in Example 21. LC-MS Method 1 $t_R$=1.32, min, m/z=539, 541(M+1)

Example 91

2-(7-bromo-1'-(2-chloro-6-methylbenzylcarbamoyl)-2,3-dihydrospiro[indene-1,4'-piperidine]-3-yl)acetic acid

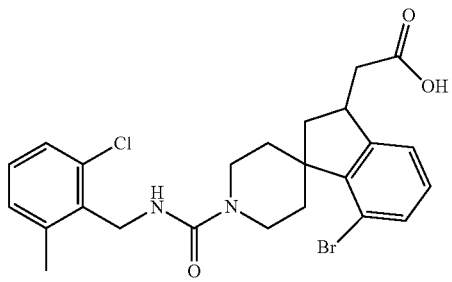 [SMILES: Cc1cccc(Cl)c1CNC(=O)N1CCC2(CC1)CC(CC(=O)O)c1cccc(Br)c12]

The title compound was prepared from ethyl 2-(7-bromo-1'-(2-chloro-6-methylbenzylcarbamoyl)-2,3-dihydrospiro[indene-1,4'-piperidine]-3-yl)acetate using a procedure analogous to that described in Example 2. LC-MS Method 1 $t_R$=1.78, min, m/z=505, 507(M+1).

Example 92

Ethyl 2-(7-bromo-1'-(2-(trifluoromethyl)benzylcarbamoyl)-2,3-dihydrospiro[indene-1,4'-piperidine]-3-yl)acetate

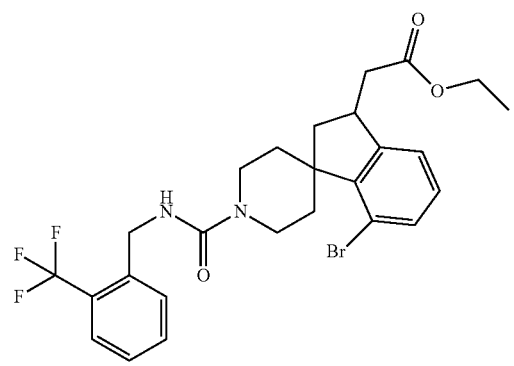 [SMILES: CCOC(=O)CC1CC2(CCN(C(=O)NCc3ccccc3C(F)(F)F)CC2)c2c(Br)cccc21]

The title compound was prepared following a procedure analogous to that described in Example 82 using 2-(trifluoromethyl)benzyl isocyanate. LC-MS Method 1 $t_R$=2.08, min, m/z=553, 555(M+1)

Example 93

Ethyl 2-(7-bromo-1'-(2-(methylsulfonyl)benzylcarbamoyl)-2,3-dihydrospiro[indene-1,4'-piperidine]-3-yl)acetate

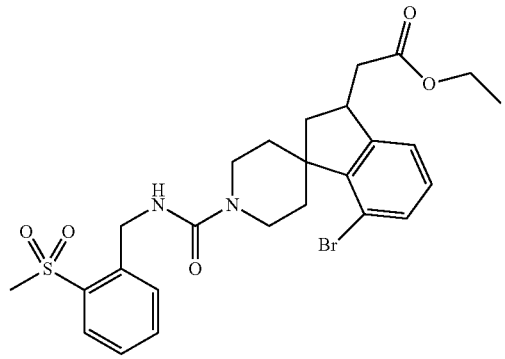 [SMILES: CCOC(=O)CC1CC2(CCN(C(=O)NCc3ccccc3S(C)(=O)=O)CC2)c2c(Br)cccc21]

The title compound was prepared following a procedure analogous to that described in Example 82 using 2-(methylsulfonyl)benzyl isocyanate. LC-MS Method 1 $t_R$=1.8, min, m/z=563, 565(M+1)

Example 94

2-(7-bromo-1'-(2-(trifluoromethyl)benzylcarbamoyl)-2,3-dihydrospiro[indene-1,4'-piperidine]-3-yl) acetic acid

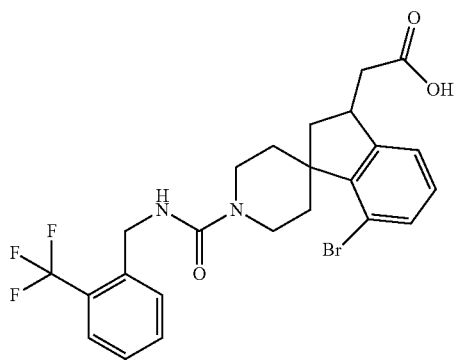 [SMILES: O=C(O)CC1CC2(CCN(C(=O)NCc3ccccc3C(F)(F)F)CC2)c2c(Br)cccc21]

The title compound was prepared from ethyl 2-(7-bromo-1'-(2-(trifluoromethyl)benzylcarbamoyl)-2,3-dihydrospiro[indene-1,4'-piperidine]-3-yl)acetate using a procedure analogous to that described in Example 2. LC-MS Method 1 t$_R$=1.78, min, m/z=525, 527(M+1)

gous to that described in Example 2. LC-MS Method 1 tR=1.35, min, m/z=526, 528(M+1)

Example 95

Ethyl 2-(7-bromo-1'-(2-isopropoxybenzylcarbamoyl)-2,3-dihydrospiro[indene-1,4'-piperidine]-3-yl)acetate

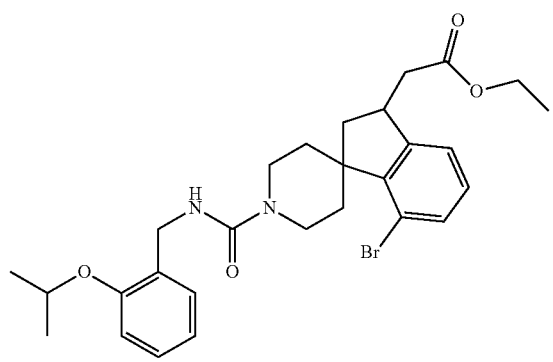 [SMILES: CCOC(=O)CC1CC2(CCN(C(=O)NCc3ccccc3OC(C)C)CC2)c2c(Br)cccc21]

The title compound was prepared following a procedure analogous to that described in Example 82 using 2-(isopropoxy)benzyl isocyanate. LC-MS Method 1 tR=2.13, min, m/z=543, 545(M+1)

Example 96

2-(7-bromo-1'-(2-(pyrrolidin-1-yl)benzylcarbamoyl)-2,3-dihydrospiro[indene-1,4'-piperidine]-3-yl)acetic acid

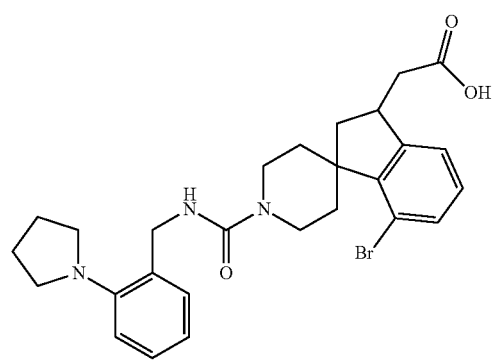 [SMILES: O=C(O)CC1CC2(CCN(C(=O)NCc3ccccc3N3CCCC3)CC2)c2c(Br)cccc21]

The title compound was prepared following a procedure analogous to that described in Example 82 using 2-(pyrrolidin-1-yl)benzyl isocyanate followed by a procedure analo-

Example 97

2-(7-bromo-1'-(2-(methylsulfonyl)benzylcarbamoyl)-2,3-dihydrospiro[indene-1,4'-piperidine]-3-yl)acetic acid

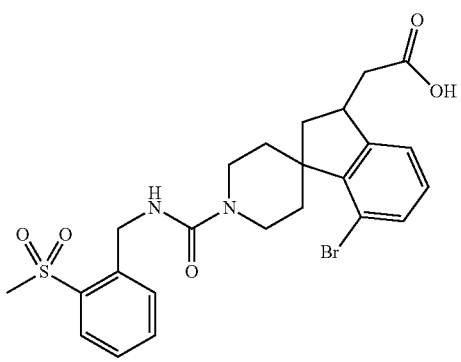 [SMILES: CS(=O)(=O)c1ccccc1CNC(=O)N1CCC2(CC1)CC(CC(=O)O)c1cccc(Br)c12]

The title compound was prepared from ethyl 2-(7-bromo-1'-(2-(methylsulfonyl)benzylcarbamoyl)-2,3-dihydrospiro[indene-1,4'-piperidine]-3-yl)acetate using a procedure analogous to that described in Example 2. LC-MS Method 1 tR=1.49, min, m/z=535, 537(M+1)

Example 98

2-(7-bromo-1'-(2-isopropoxybenzylcarbamoyl)-2,3-dihydrospiro[indene-1,4'-piperidine]-3-yl)acetic acid

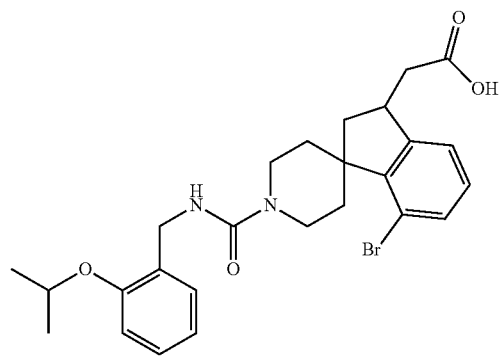 [SMILES: CC(C)Oc1ccccc1CNC(=O)N1CCC2(CC1)CC(CC(=O)O)c1cccc(Br)c12]

The title compound was prepared from ethyl 2-(7-bromo-F-(2-isopropoxybenzylcarbamoyl)-2,3-dihydrospiro[indene-1,4'-piperidine]-3-yl)acetate using a procedure analo-

Example 99

7-bromo-3-oxo-N-(2-(trifluoromethoxy)benzyl)-2,3-dihydrospiro[indene-1,4'-piperidine]-1'-carboxamide

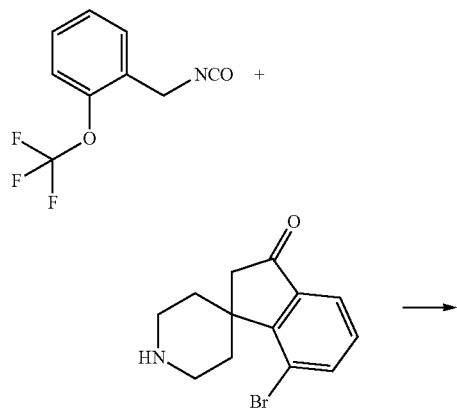

The title compound was prepared following a procedure analogous to that described in Example 19. LC-MS Method 1 $t_R$=1.85, min, m/z=499, 497.

Example 100

7-chloro-2-methyl-3-oxo-N-(2-(trifluoromethyl)benzyl)spiro[isoindoline-1,4'-piperidine]-1'-carboxamide

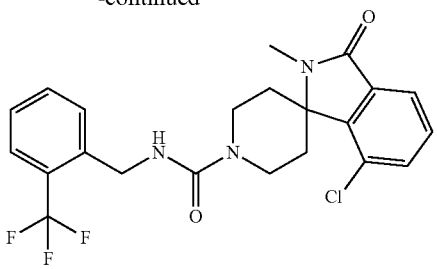

The title compound was prepared following a procedure analogous to that described in Example 19. LC-MS Method 1 $t_R$=1.59, min, m/z=452, 454(M+1).

Example 101

Ethyl 2-(7-bromo-1'-(methyl(2-(trifluoromethyl)benzyl)carbamoyl)-2,3-dihydrospiro[indene-1,4'-piperidine]-3-yl)acetate

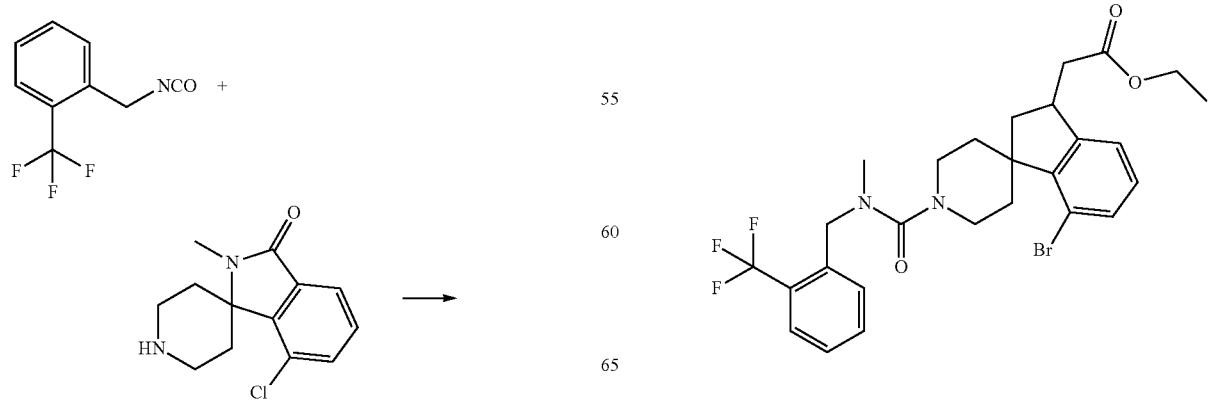

LC-MS Method 1 $t_R$=2.33, min, m/z=567, 569(M+1).

Example 102

2-(7-bromo-1'-(methyl(2-(trifluoromethyl)benzyl)carbamoyl)-2,3-dihydrospiro[indene-1,4'-piperidine]-3-yl)acetic acid

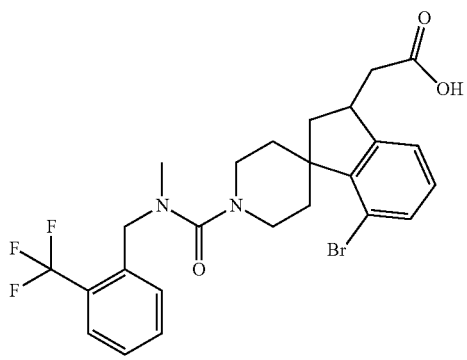 [SMILES: CN(Cc1ccccc1C(F)(F)F)C(=O)N1CCC2(CC1)CC(CC(=O)O)c1cccc(Br)c12]

The title compound was prepared from ethyl 2-(7-bromo-1'-(methyl(2-(trifluoromethyl)benzyl)carbamoyl)-2,3-dihydrospiro[indene-1,4'-piperidine]-3-yl)acetate using a procedure analogous to that described in Example 2. LC-MS Method 1 $t_R$=1.99, min, m/z=539, 541(M+1).

Example 103

Ethyl 2-(7-bromo-1'-((2-fluorobenzyl)(methyl)carbamoyl)-2,3-dihydrospiro[indene-1,4'-piperidine]-3-yl)acetate

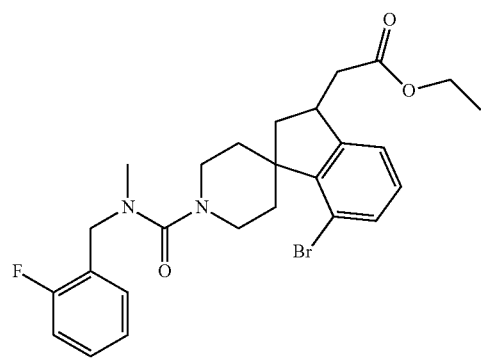 [SMILES: CCOC(=O)CC1CC2(CCN(C(=O)N(C)Cc3ccccc3F)CC2)c2c(Br)cccc21]

The title compound was prepared by analogy with Example 101. LC-MS Method 1 $t_R$=2.21, min, m/z=517, 519(M+1).

Example 104

2-(7-bromo-1'((2-fluorobenzyl)(methyl)carbamoyl)-2,3-dihydrospiro[indene-1,4'-piperidine]-3-yl)acetic acid

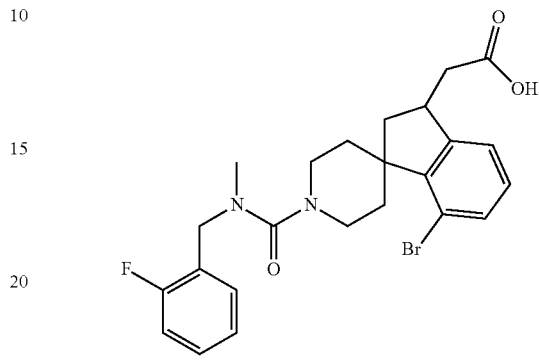

The title compound was prepared from ethyl 2-(7-bromo-1'4(2-fluorobenzyl)(methyl)carbamoyl)-2,3-dihydrospiro[indene-1,4'-piperidine]-3-yl)acetate using a procedure analogous to that described in Example 2. LC-MS Method 1 $t_R$=1.86, min, m/z=489, 491(M+1).

Example 105

2-(trifluoromethyl)benzyl 7-bromo-3-oxo-2,3-dihydrospiro[indene-1,4'-piperidine]-1'-carboxylate

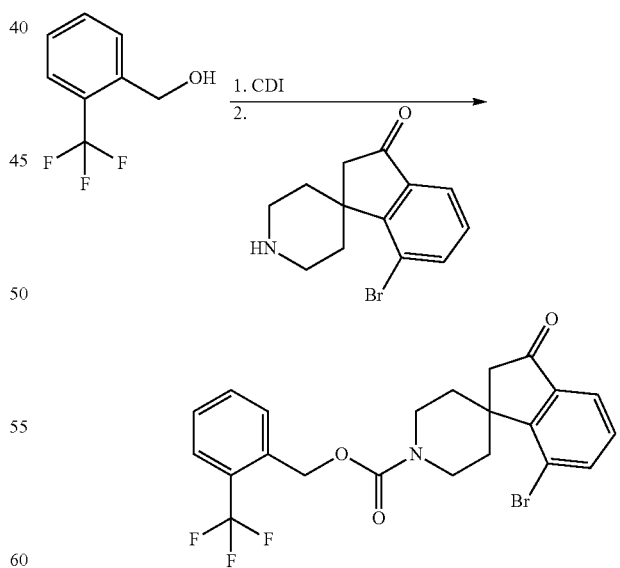

To o-(trifluoromethyl)benzyl alcohol (35 mg, 0.20 mmol) in CH$_2$Cl$_2$ (4 mL) was added was a solution of carbonyl diimidazole (29 mg, 0.18 mmol) in CH$_2$Cl$_2$ (4 mL). The mixture was stirred at rt for 2 h. A 1-mL aliquot of the resulting solution (0.05 mmol) was added to a solution 7-bromospiro[indene-1,4'-piperidin]-3(2H)-one (14.5 mg, 0.05 mmol) in CH$_2$Cl$_2$ (1 mL). The mixture was stirred at rt for 16 h, concentrated, redissolved in MeCN (1 mL) and heated at 60° C. for 2 h. Prep HPLC afforded the title compound. LC-MS Method 1 t$_R$=2.06, min, m/z=484, 482.

Example 106

7-bromo-1'-(2-(2-(trifluoromethyl)phenoxy)acetyl)spiro[indene-1,4'-piperidin]-3(2H)-one

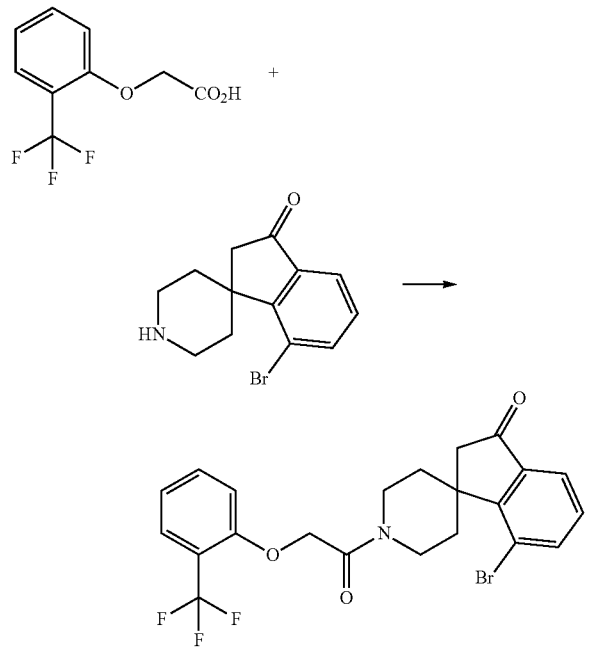

The title compound was prepared following a procedure analogous to that described in Example 1. LC-MS Method 1 t$_R$=1.90 min, m/z=484, 482.

Example 107

7-bromo-1'-(2-(2-(trifluoromethyl)phenylamino)acetyl)spiro[indene-1,4'-piperidin]

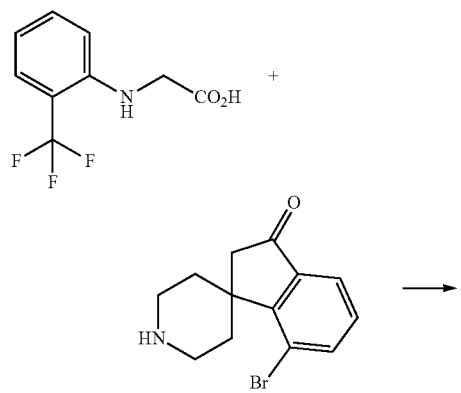

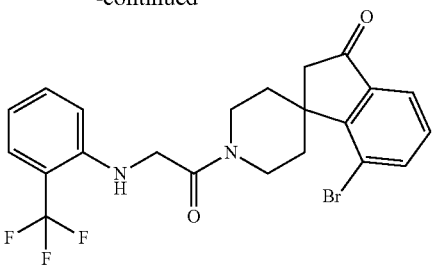

The title compound was prepared following a procedure analogous to that described in Example 1. LC-MS Method 1 t$_R$=2.00 min, m/z=483, 481.

Biological Test Example 1

The inhibition of microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxysteroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at rt. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

Biological Test Example 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% CO$_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

Biological Test Example 1

| Compound | IC$_{50}$ Range[a] | Average % inhibition at 100 nM | Average % inhibition at 111 nM |
|---|---|---|---|
| EXAMPLE 1 | ++ | 94.9 | 89.4 |
| EXAMPLE 2 | ++ | 91.7 | 97.4 |
| EXAMPLE 2.1 | ++ | 96.6 | |
| EXAMPLE 2.2 | ++ | 100.3 | |
| EXAMPLE 3 | ++ | 96.3 | |
| EXAMPLE 4 | ++ | | 94.2 |
| EXAMPLE 5 | ++ | | 83.3 |
| EXAMPLE 6 | ++ | | 97.4 |
| EXAMPLE 7 | ++ | | 87.3 |
| EXAMPLE 8 | ++ | | 85.5 |
| EXAMPLE 9 | ++ | | 77.8 |
| EXAMPLE 10 | ++ | | 87.7 |
| EXAMPLE 11 | ++ | | 75.1 |
| EXAMPLE 12 | ++ | | 90.3 |
| EXAMPLE 13 | ++ | 94.6 | 94.8 |
| EXAMPLE 14 | ++ | 85.6 | 90.9 |
| EXAMPLE 15 | ++ | 95.3 | 92.6 |
| EXAMPLE 16 | ++ | 95.3 | 98.6 |
| EXAMPLE 17 | ++ | | 81.2 |
| EXAMPLE 18 | ++ | | 93.3 |
| EXAMPLE 19 | ++ | 98.1 | |
| EXAMPLE 20 | ++ | | 29.0 |
| EXAMPLE 21 | ++ | | 87.4 |
| EXAMPLE 22 | ++ | | 95.3 |
| EXAMPLE 23 | ++ | | 94.9 |
| EXAMPLE 24 | ++ | | 82.3 |
| EXAMPLE 25 | ++ | 95.5 | 95.3 |
| EXAMPLE 26 | ++ | | 79.0 |
| EXAMPLE 27 | ++ | | 89.8 |
| EXAMPLE 28 | ++ | | 92.7 |
| EXAMPLE 29 | ++ | | 94.2 |
| EXAMPLE 30 | ++ | 90.3 | 94.6 |
| EXAMPLE 31 | ++ | 99.9 | |
| EXAMPLE 32 | ++ | | 83.4 |
| EXAMPLE 33 | + | | 31.5 |
| EXAMPLE 34 | + | | 38.2 |
| EXAMPLE 35 | + | | 41.4 |
| EXAMPLE 36 | + | | 0.6 |
| EXAMPLE 37 | + | | 7.1 |
| EXAMPLE 38 | + | | 21.3 |
| EXAMPLE 39 | ++ | | 64.8 |
| EXAMPLE 40 | ++ | | 71.2 |
| EXAMPLE 41 | ++ | 91.2 | |
| EXAMPLE 42 | ++ | | 79.3 |
| EXAMPLE 43 | ++ | 90.6 | |
| EXAMPLE 44 | ++ | | 69.9 |
| EXAMPLE 45 | + | | 43.2 |
| EXAMPLE 46 | ++ | | 78.6 |
| EXAMPLE 47 | ++ | | 83.3 |
| EXAMPLE 48 | ++ | 80.6 | 86.3 |
| EXAMPLE 49 | + | | 49.2 |
| EXAMPLE 50 | + | | 68.9 |
| EXAMPLE 51 | ++ | 76.8 | |
| EXAMPLE 52 | ++ | 61.2 | |
| EXAMPLE 53 | ++ | 67.2 | |
| EXAMPLE 54 | ++ | 71.7 | |
| EXAMPLE 55 | ++ | | 76.5 |
| EXAMPLE 56 | ++ | | 92.7 |
| EXAMPLE 57 | + | | 37.6 |
| EXAMPLE 58 | ++ | 97.1 | 87.4 |
| EXAMPLE 59 | ++ | | 66.6 |
| EXAMPLE 60 | ++ | | 92.6 |
| EXAMPLE 61 | ++ | 93.3 | 96.7 |
| EXAMPLE 62 | ++ | | 87.2 |
| EXAMPLE 63 | + | | 22.5 |
| EXAMPLE 64 | ++ | | 100.0 |
| EXAMPLE 65 | ++ | | 87.7 |
| EXAMPLE 66 | ++ | | 92.1 |
| EXAMPLE 67 | ++ | 100.3 | |
| EXAMPLE 68 | ++ | | 81.5 |
| EXAMPLE 69 | ++ | 93.5 | 93.8 |
| EXAMPLE 70.1 | ++ | | 97.6 |
| EXAMPLE 70.2 | ++ | 95.7 | 99.2 |
| EXAMPLE 71 | ++ | | 93.9 |
| EXAMPLE 72 | ++ | | 82.4 |
| EXAMPLE 73 | ++ | 96.6 | 95.4 |
| EXAMPLE 74 | ++ | | 89.5 |
| EXAMPLE 75 | ++ | | 52.2 |
| EXAMPLE 76 | ++ | | 60.0 |
| EXAMPLE 77 | + | | 26.3 |
| EXAMPLE 78 | ++ | | 52.4 |
| EXAMPLE 79 | + | | 51.4 |
| EXAMPLE 80 | ++ | | 95.1 |
| EXAMPLE 81 | ++ | | 59.2 |
| EXAMPLE 82 | + | | 28.6 |
| EXAMPLE 83 | + | | 10.9 |
| EXAMPLE 84 | + | | 42.6 |
| EXAMPLE 85 | + | | 19.4 |
| EXAMPLE 86 | ++ | | 58.7 |
| EXAMPLE 87 | ++ | | 57.2 |
| EXAMPLE 88 | ++ | | 66.2 |
| EXAMPLE 89 | ++ | | 61.2 |
| EXAMPLE 90 | + | | 52.4 |
| EXAMPLE 91 | ++ | | 64.1 |
| EXAMPLE 92 | ++ | | 70.5 |
| EXAMPLE 93 | + | | 18.5 |
| EXAMPLE 94 | ++ | | 75.7 |
| EXAMPLE 95 | + | | 19.9 |
| EXAMPLE 96 | + | | 48.9 |
| EXAMPLE 97 | + | | 5.6 |
| EXAMPLE 98 | ++ | | 48.2 |
| EXAMPLE 99 | ++ | | 75.6 |
| EXAMPLE 100 | + | | 46.8 |
| EXAMPLE 101 | + | | 42.6 |
| EXAMPLE 102 | ++ | | 64.4 |
| EXAMPLE 103 | ++ | | 79.4 |
| EXAMPLE 104 | ++ | | 88.7 |
| EXAMPLE 105 | ++ | | 82.3 |
| EXAMPLE 106 | ++ | | |
| EXAMPLE 107 | + | | |

[a] ++ means IC$_{50}$ = <100 nM, + means IC$_{50}$ = 100-1000 nM, # means IC$_{50}$ > 100 nM, − means IC$_{50}$ > 1000 nM.

Prophetic Examples
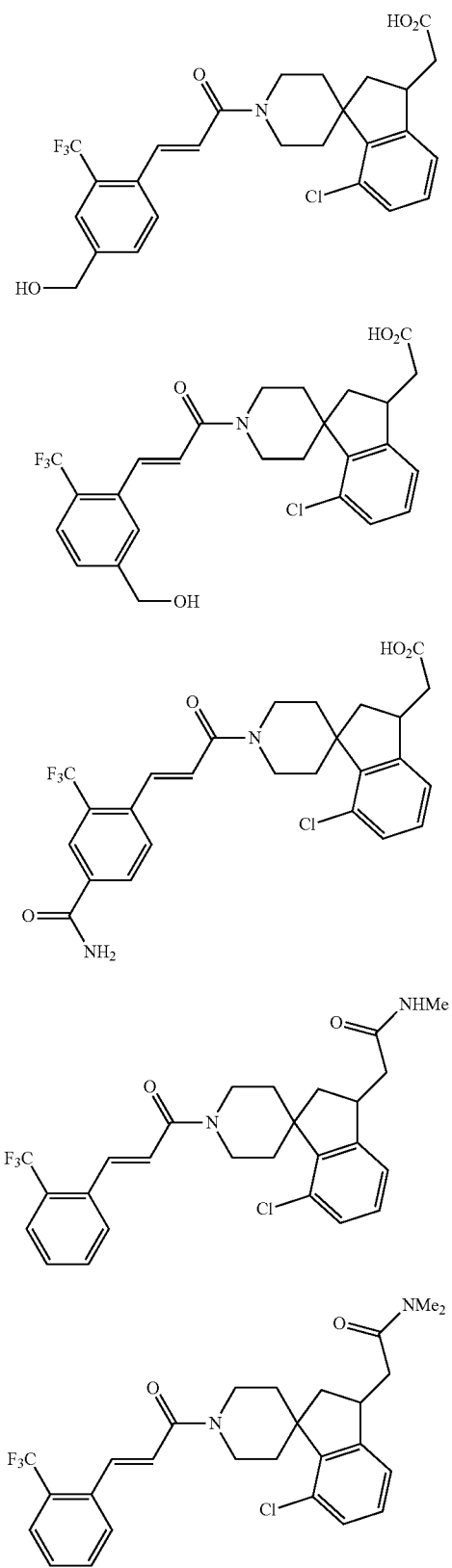
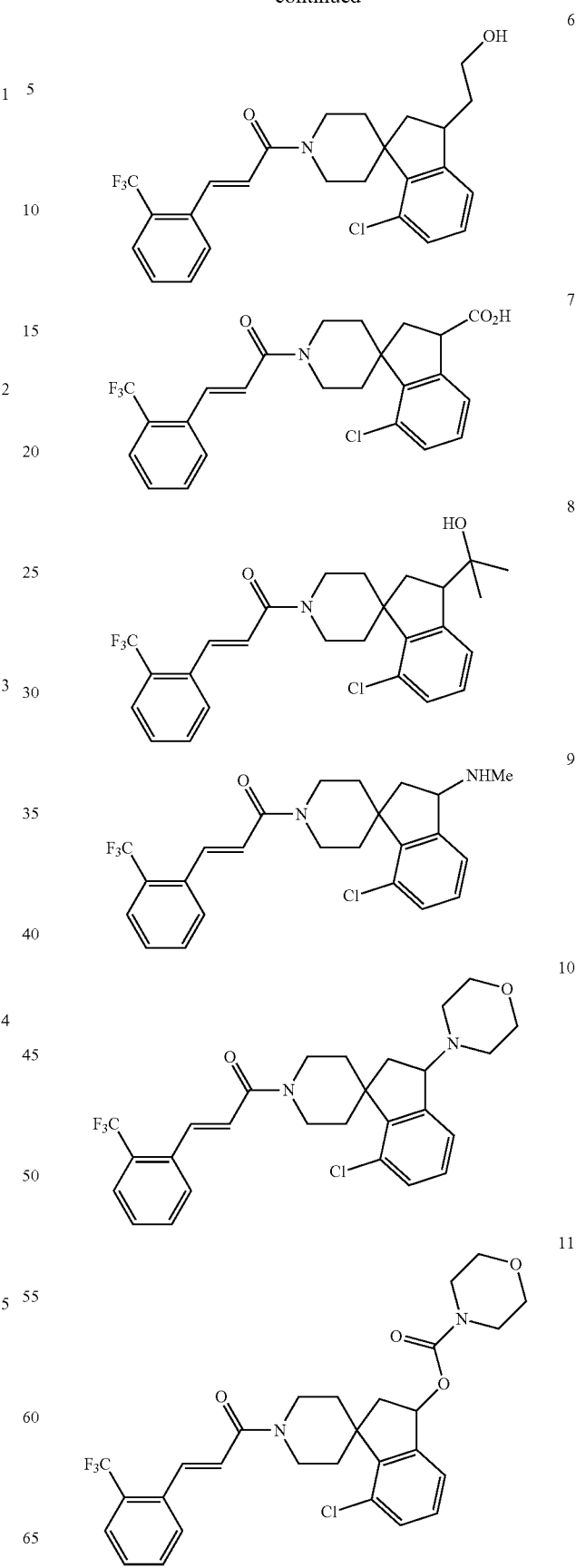

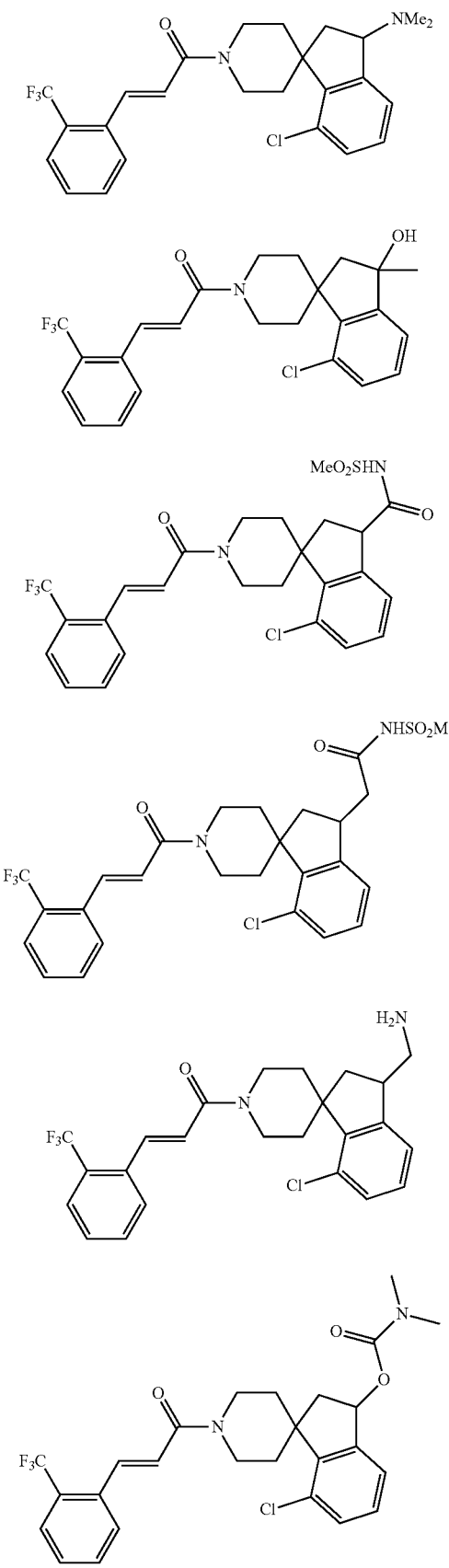
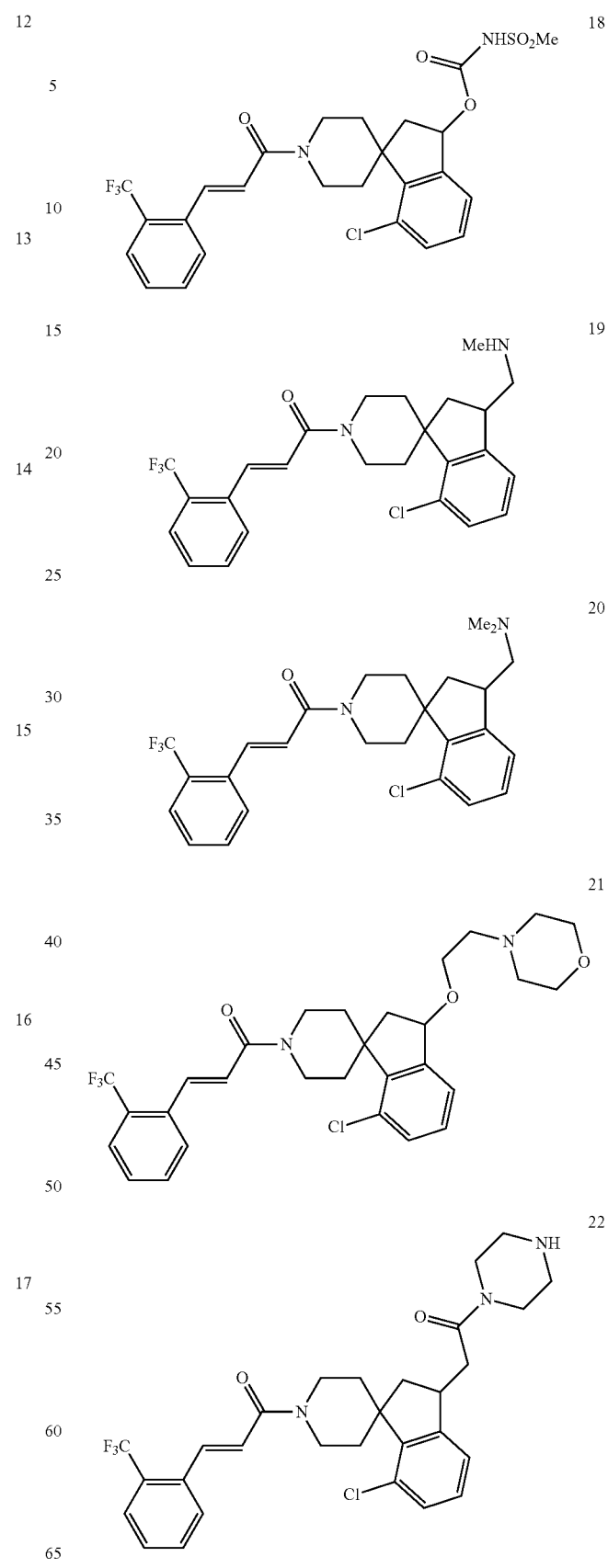

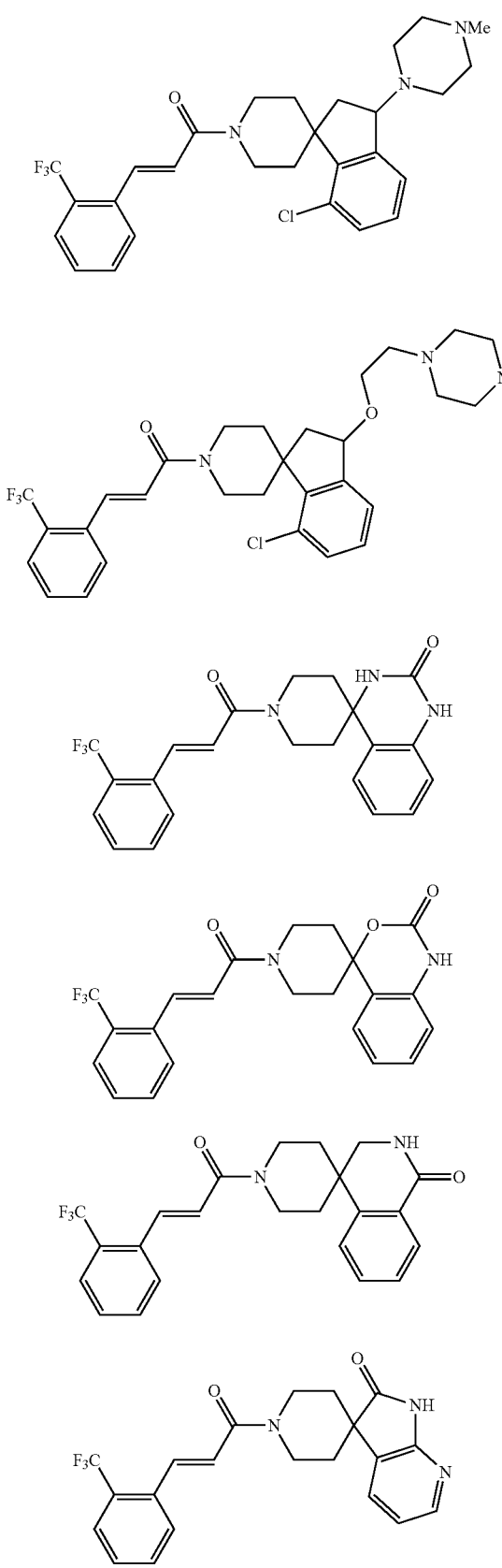
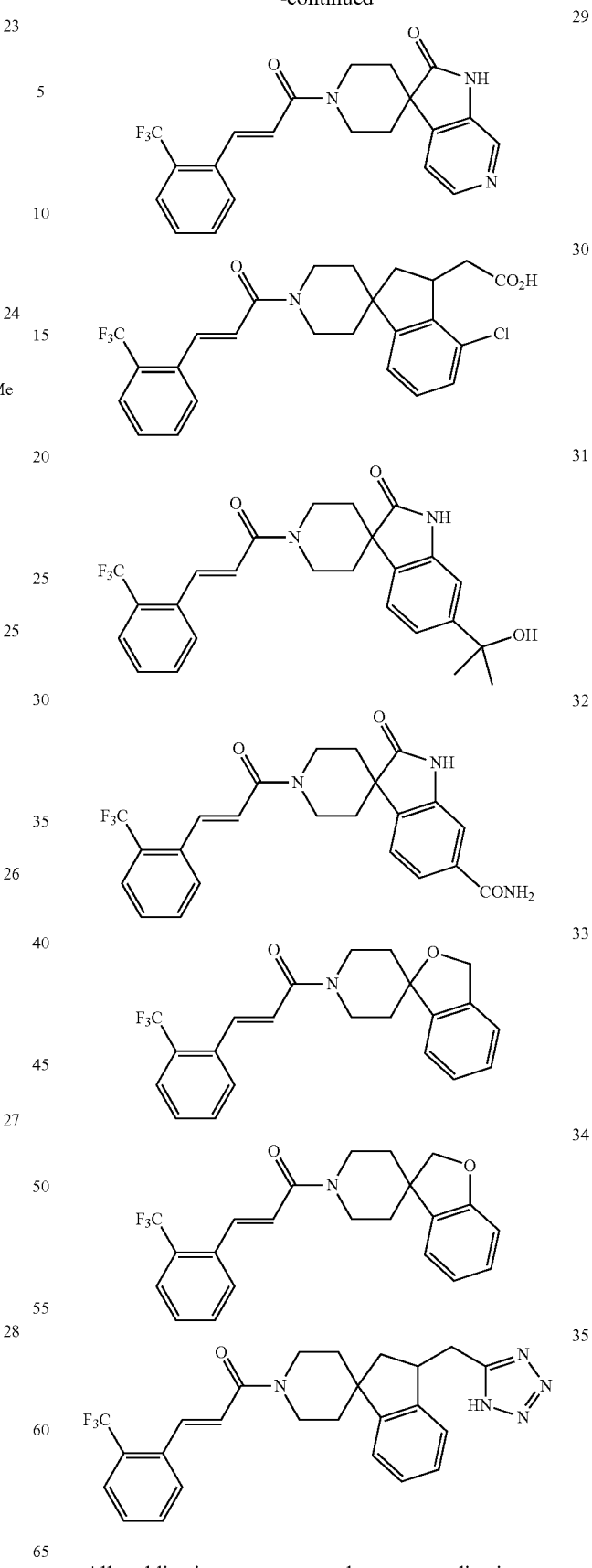
All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound represented by the following structural formula:

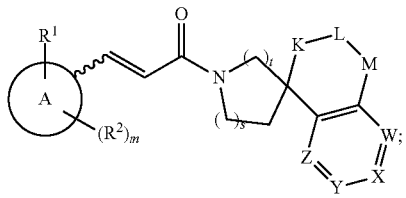

or a pharmaceutically acceptable salt thereof, wherein:

A is a monocyclic heteroaromatic group or a phenyl group;

$R^1$ is independently halo, $OR^{11}$, $S(O)_pR^{11}$, CN, $NO_2$, $C(O)R^{11}$, $C(S)R^{11}$, $CO_2R^{11}$, CHO, $(C_1$-$C_6)$alkyl, halo$(C_1$-$C_6)$alkyl, halo$(C_1$-$C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, $NR^{11}SO_2R^{13}$ or HetCy; or a $(C_1$-$C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1$-$C_6)$alkyl, halo$(C_1$-$C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

each $R^2$ is independently hydrogen, halo, $OR^{11}$, $S(O)_pR^{11}$, CN, $NO_2$, $C(O)R^{11}$, $C(S)R^{11}$, $CO_2R^{11}$, CHO, $(C_1$-$C_6)$alkyl, halo$(C_1$-$C_6)$alkyl, halo$(C_1$-$C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1$-$C_6)$alkyl substituted with halo, $OR^{11}$, $S(O)_pR^{11}$, CN, $NO_2$, $C(O)R^{11}$, $C(S)R^{11}$, $CO_2R^{11}$, CHO, $(C_1$-$C_6)$alkyl, halo$(C_1$-$C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

m is an integer from 0-3;

p is 0, 1 or 2;

s is 1 or 2;

t is 1 or 2;

K, L and M are independently selected from O, $NR^4$, $CR^{4a}R^{4b}$ or CO; provided: i) that no more than one of K, L and M is CO; ii) that K-L and L-M are not —O—O—; and iii) that K-L-M- is not —O—$NR^4$—O— or —$NR^4$—$NR^4$—$NR^4$—;

each $R^4$ is independently hydrogen, $(C_1$-$C_6)$alkyl, $C(O)R^{14}$, $C(S)R^{14}$, $COOR^{14}$, $C(S)OR^{14}$, $C(O)NR^{14}R^{15}$, $C(S)NR^{14}R^{15}$, $SO_2R^{14}$, $SO_2NR^{14}R^{15}$, Ar or HetAr; or $(C_1$-$C_6)$alkyl substituted with OH, $NR^{14}R^{15}$, $C(O)R^{14}$, $C(S)$ $R^{14}$, $COOR^{14}$, $C(S)OR^{14}$, $C(O)NR^{14}R^{15}$, $C(S)NR^{14}R^{15}$, $NR^{14}C(O)NR^{14}R^{15}$, $NR^{14}C(S)NR^{14}R^{15}$, $OC(O)NR^{14}R^{15}$, $OC(S)NR^{14}R^{15}$, $NR^{14}C(O)OR^{14}$, $NR^{14}C(S)OR^{14}$, $SO_2R^{14}$, $NR^{14}SO_2R^{14}$, $SO_2NR^{14}R^{15}$, $NR^{14}SO_2NR^{14}R^{15}$, Ar or HetAr;

each $R^{4a}$ and each $R^{4b}$ is independently selected from hydrogen, $OR^{14}$, $NR^{14}R^{15}$, $C(O)R^{14}$, $C(S)R^{14}$, $COOR^{14}$, $C(S)OR^{14}$, $C(O)NHSO_2R^{14}$, $C(S)NHSO_2R^{14}$, $C(O)NR^{14}R^{15}$, $C(S)NR^{14}R^{15}$, $NR^{11}C(O)R^{14}$, $NR^{11}C(S)R^{14}$, $NR^{11}C(O)NR^{14}R^{15}$, $NR^{11}C(S)NR^{14}R^{15}$, $NR^{11}C(O)NHSO_2R^{14}$, $NR^{11}C(S)NHSO_2R^{14}$, $OC(O)R^{14}$, $OC(S)R^{14}$, $OC(O)NR^{14}R^{15}$, $OC(S)NR^{14}R^{15}$, $OC(O)NHSO_2R^{14}$, $OC(S)NHSO_2R^{14}$, $NR^{11}C(O)OR^{14}$, $NR^{11}C(S)OR^{14}$, $SO_2R^{14}$, $NR^{11}SO_2R^{14}$, $SO_2NR^{14}R^{15}$, $NR^{11}SO_2NR^{14}R^{15}$, Ar, HetAr, or HetCy; or $(C_1$-$C_6)$alkyl optionally substituted with OH, $NR^{14}R^{15}$, $C(O)R^{14}$, $C(S)R^{14}$, $C(O)NHSO_2R^{14}$, $C(S)NHSO_2R^{14}$, $COOR^{14}$, $C(S)OR^{14}$, $C(O)NR^{14}R^{15}$, $C(S)NR^{14}R^{15}$, $NR^{11}C(O)NR^{14}R^{15}$, $NR^{11}C(S)NR^{14}R^{15}$, $OC(O)NR^{14}R^{15}$, $OC(S)NR^{14}R^{15}$, $NR^{11}C(O)OR^{14}$, $NR^{11}C(S)OR^{14}$, $SO_2R^{14}$, $NR^{11}SO_2R^{14}$, $SO_2NR^{14}R^{15}$, Ar, HetAr, or HetCy;

W, X, Y and Z are independently selected from N, $CR^5$, provided that no more than two of W, X, Y and Z are N;

each $R^5$ is independently selected from hydrogen, halo, $OR^{11}$, $S(O)_pR^{11}$, CN, $NO_2$, $COR^{11}$, $CSR^{11}$, $CO_2R^{11}$, CHO, $(C_1$-$C_6)$alkyl, halo$(C_1$-$C_6)$alkyl, halo$(C_1$-$C_6)$alkoxy, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$; or a $(C_1$-$C_6)$ alkyl substituted with halo, $OR^{11}$, $S(O)_pR^{11}$, CN, $NO_2$, $C(O)R^{11}$, $C(S)R^{11}$, $CO_2R^{11}$, CHO, $(C_1$-$C_6)$alkyl, halo $(C_1$-$C_6)$alkyl, $NR^{11}R^{12}$, $CONR^{11}R^{12}$, $OC(O)NR^{11}R^{12}$, $NR^{11}C(O)NR^{11}R^{12}$, $CSNR^{11}R^{12}$, $OC(S)NR^{11}R^{12}$, $NR^{11}C(S)NR^{11}R^{12}$, $SO_2NR^{11}R^{12}$, $NR^{11}SO_2NR^{11}R^{12}$, $NR^{11}C(O)R^{12}$, $OC(O)R^{12}$, $NR^{11}C(S)R^{12}$, $NR^{11}C(O)OR^{13}$, $NR^{11}C(S)OR^{13}$, or $NR^{11}SO_2R^{13}$;

each $R^{11}$ and each $R^{12}$ is independently selected from hydrogen, $(C_1$-$C_6)$alkyl or $(C_1$-$C_6)$hydroxyalkyl;

$R^{13}$ is $(C_1$-$C_6)$alkyl or $(C_1$-$C_6)$hydroxyalkyl;

each $R^{14}$ and each $R^{15}$ is independently hydrogen or $(C_1$-$C_6)$alkyl, optionally substituted with $OR^{11}$, $NR^{11}R^{12}$, $C(O)R^{11}$, $C(S)R^{11}$, $COOR^{11}$, $C(S)OR^{11}$, $C(O)NR^{11}R^{12}$, $C(S)NR^{11}R^{12}$, $NR^{11}C(O)R^{11}$, $NR^{11}C(S)R^{11}$, $NR^{11}C(O)NR^{11}R^{12}$, $NR^{11}C(S)NR^{11}R^{12}$, $NR^{11}C(O)NHSO_2R^{11}$, $NR^{11}C(S)NHSO_2R^{11}$, $OC(O)R^{11}$, $OC(S)R^{11}$, $OC(O)NR^{11}R^{12}$, $OC(S)NR^{11}R^{12}$, $OC(O)NHSO_2R^{11}$, $OC(S)NHSO_2R^{11}$, $NR^{11}C(O)OR^{11}$, $NR^{11}C(S)OR^{11}$, $SO_2R^{11}$, $NR^{11}SO_2R^{11}$, $SO_2NR^{11}R^{12}$, $NR^{11}SO_2NR^{11}R^{12}$, Ar, HetAr, or HetCy;

or $NR^{14}R^{15}$ taken together forms a 4, 5, 6- or 7-membered heterocyclic group containing 1 or 2 nitrogen atoms, 0 or 1 oxygen atoms and 0 or 1 sulfur atoms, said ring being optionally substituted at any one or more substitutable ring carbon with oxo, hydroxy, or $(C_1$-$C_3)$alkyl, and optionally substituted at any one or more substitutable ring nitrogen with $(C_1$-$C_3)$alkyl, $C(O)R^{11}$, $C(O)OR^{11}$ or $C(O)NR^{11}R^{12}$;

each Ar is aryl optionally substituted with halogen, $(C_1$-$C_6)$alkyl, hydroxy, $(C_1$-$C_6)$alkoxy, $(C_1$-$C_6)$alkylamino, di$(C_1$-$C_6)$alkylamino, $NO_2$, CN, $CONH_2$, $(C_1$-$C_6)$haloalkyl or $(C_1$-$C_6)$haloalkoxy;

each HetAr is heteroaryl optionally substituted with halogen, $(C_1$-$C_6)$alkyl, hydroxy, $(C_1$-$C_6)$alkoxy, $(C_1$-$C_6)$ alkylamino, di(C$_1$-C$_6$)alkylamino, NO$_2$, CN, CONH$_2$, (C$_1$-C$_6$)haloakyl or (C$_1$-C$_6$)haloalkoxy; and each HetCy is a monocyclic heterocyclic group containing at least one ring atom selected from nitrogen, oxygen or sulfur, said ring being optionally substituted at any one or more substitutable ring carbon with oxo, hydroxy, or (C$_1$-C$_3$)alkyl, and optionally substituted at any one or more substitutable ring nitrogen with (C$_1$-C$_3$)alkyl, C(O)R$^{11}$, C(O)OR$^{11}$ or C(O)NR$^{11}$R$^{12}$.

2. A compound represented by the following structural formula:

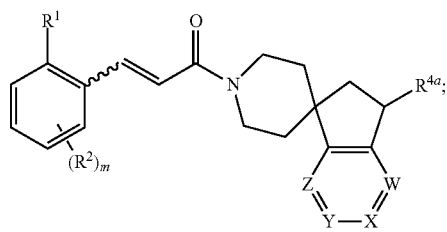

or a pharmaceutically acceptable salt thereof.

3. The compound of claim 2, wherein the compound is represented by the following structural formula:

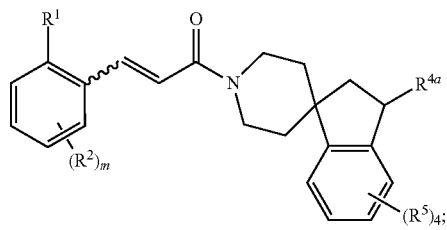

or a pharmaceutically acceptable salt thereof.

4. A compound represented by the following structural formula:

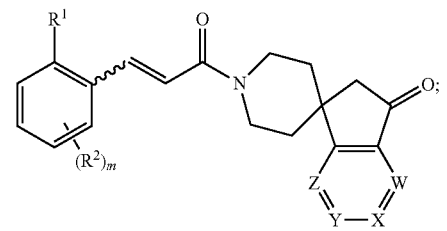

or a pharmaceutically acceptable salt thereof.

5. The compound of claim 4, wherein the compound is represented by the following structural formula:

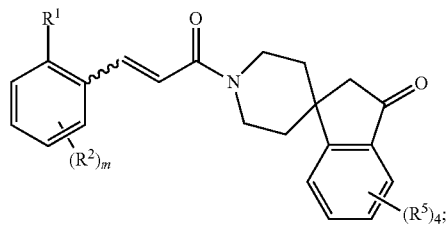

or a pharmaceutically acceptable salt thereof.

6. The compound of claim 1, wherein the compound is represented by the following structural formula:

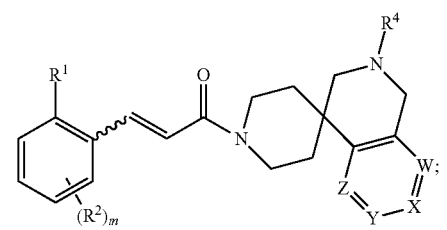

or a pharmaceutically acceptable salt thereof.

7. The compound of claim 6, wherein the compound is represented by the following structural formula:

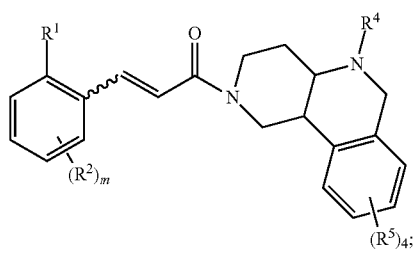

or a pharmaceutically acceptable salt thereof.

8. A compound represented by the following structural formula:

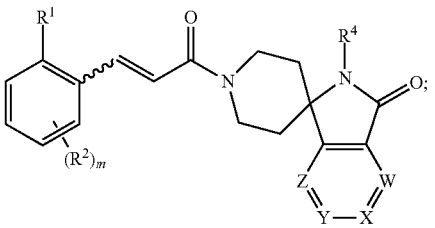

or a pharmaceutically acceptable salt thereof.

9. The compound of claim 8, wherein the compound is represented by the following structural formula:

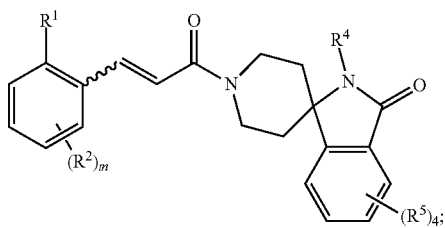

or a pharmaceutically acceptable salt thereof.

10. The compound of claim 1, wherein the compound is represented by the following structural formula:

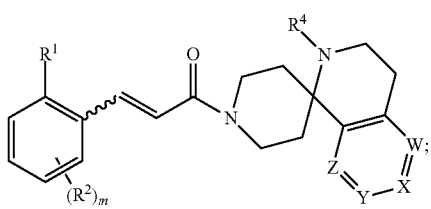

or a pharmaceutically acceptable salt thereof.

11. The compound of claim 10, wherein the compound is represented by the following structural formula:

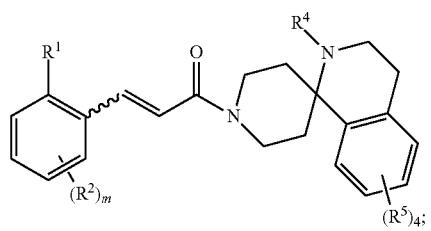

or a pharmaceutically acceptable salt thereof.

12. A compound represented by the following structural formula:

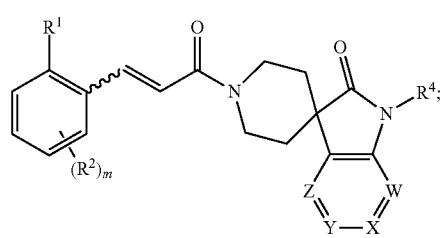

or a pharmaceutically acceptable salt thereof.

13. The compound of claim 12, wherein the compound is represented by the following structural formula:

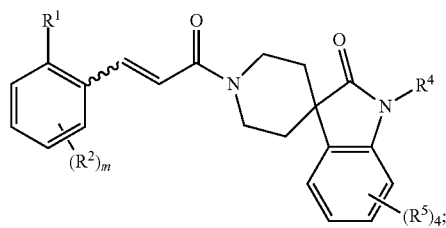

or a pharmaceutically acceptable salt thereof.

14. The compound of claim 1, wherein the compound is represented by the following structural formula:

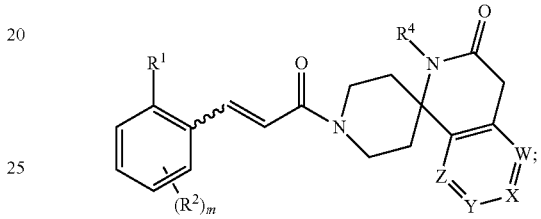

or a pharmaceutically acceptable salt thereof.

15. The compound of claim 14, wherein the compound is represented by the following structural formula:

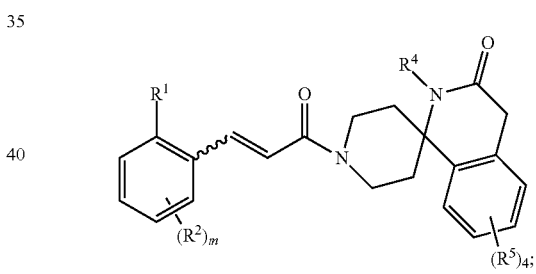

or a pharmaceutically acceptable salt thereof.

16. The compound of claim 1, wherein the compound is represented by the following structural formula:

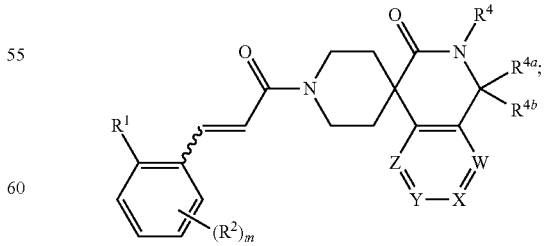

or a pharmaceutically acceptable salt thereof.

17. The compound of claim 16, wherein the compound is represented by the following structural formula:

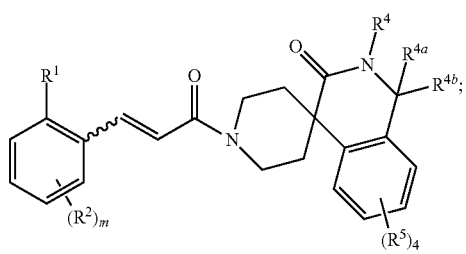

or a pharmaceutically acceptable salt thereof.

18. The compound of claim 3, wherein $R^1$ is halo, $(C_1-C_3)$alkyl, $(C_1-C_3)$haloalkyl, $(C_1-C_3)$alkoxy, or $(C_1-C_3)$haloalkoxy.

19. The compound of claim 18, wherein m=0.

20. The compound of claim 18, wherein m=1; and each $R^2$ is independently hydrogen, halo, $(C_1-C_3)$alkyl, hydroxy, hydroxy$(C_1-C_3)$alkyl, COO$(C_1-C_3)$alkyl, CONH$_2$, $(C_1-C_3)$alkoxy, $(C_1-C_3)$alkylamino, di$(C_1-C_3)$alkylamino, NO$_2$, CN, $(C_1-C_3)$haloalkyl or $(C_1-C_3)$haloalkoxy.

21. The compound of claim 20, wherein each $R^4$ is independently hydrogen, $(C_1-C_6)$alkyl, C(O)$R^{14}$, COO$R^{14}$, or SO$_2R^{14}$.

22. The compound of claim 20, wherein each $R^4$ is independently C(O)$R^{14}$, C(S)$R^{14}$, COO$R^{14}$, C(S)O$R^{14}$, C(O)NR$^{14}$R$^{15}$, C(S)NR$^{14}$R$^{15}$, SO$_2R^{14}$, or SO$_2$NR$^{14}$R$^{15}$;

each $R^{4a}$ and each $R^{4b}$ is independently selected from hydrogen, OR$^{14}$, NR$^{14}$R$^{15}$, C(O)NR$^{14}$R$^{15}$, NR$^{11}$C(O)R$^{14}$, NR$^{11}$C(O)NHSO$_2R^{14}$, NR$^{11}$C(O)NR$^{14}$R$^{15}$, OC(O)R$^{14}$, OC(O)NR$^{14}$R$^{15}$, OC(O)NHSO$_2R^{14}$, HetCy, $(C_1-C_3)$alkyl, or $(C_1-C_3)$alkyl substituted with NR$^{14}$R$^{15}$, COOR$^{14}$, C(O)NHSO$_2R^{14}$, or C(O)NR$^{14}$R$^{15}$; and each $R^5$ is independently hydrogen, halo, $(C_1-C_3)$alkyl, $(C_1-C_3)$alkoxy, hydroxy, C(O)OH, C(O)O$(C_1-C_3)$alkyl, C(O)NH$_2$, C(O)NH$(C_1-C_3)$alkyl, C(O)N(($C_1-C_3$)alkyl)$_2$, $(C_1-C_3)$alkylamino, di$(C_1-C_3)$alkylamino, NO$_2$, CN, $(C_1-C_3)$haloakyl or $(C_1-C_3)$haloalkoxy.

23. The compound of claim 22, wherein $R^{14}$ is hydrogen and $R^{15}$ is independently hydrogen, $(C_1-C_3)$alkyl, hydroxy$(C_1-C_3)$alkyl, amino$(C_1-C_3)$alkyl, $(C_1-C_3)$alkylamino$(C_1-C_3)$alkyl, or di-$(C_1-C_3)$alkylamino$(C_1-C_3)$alkyl; or NR$^{14}$R$^{15}$ taken together forms a 5- or 6-membered heterocyclic group containing 1 or 2 nitrogen atoms, 0 or 1 oxygen atoms and 0 or 1 sulfur atoms, said ring being optionally substituted at any one or more substitutable ring carbon with oxo, hydroxy, or $(C_1-C_3)$alkyl, and optionally substituted at any one or more substitutable ring nitrogen with $(C_1-C_3)$alkyl, C(O)R$^{11}$, C(O)OR$^{11}$ or C(O)NR$^{11}$R$^{12}$.

24. A pharmaceutical composition comprising an effective amount of a compound according to claim 1, and a pharmaceutically acceptable carrier or diluent.

25. A compound selected from:

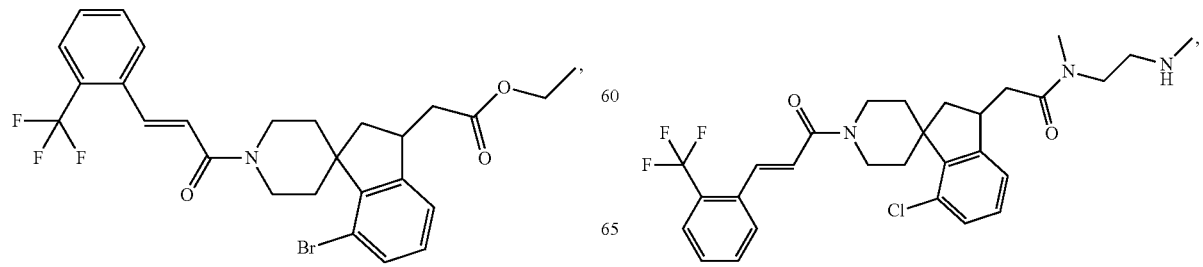

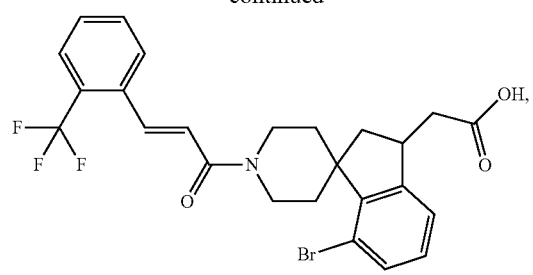

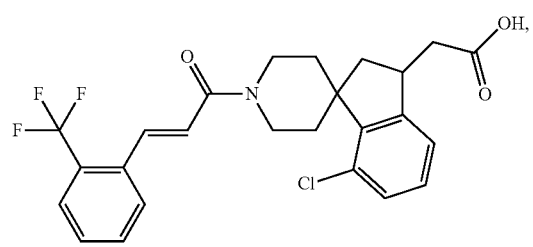

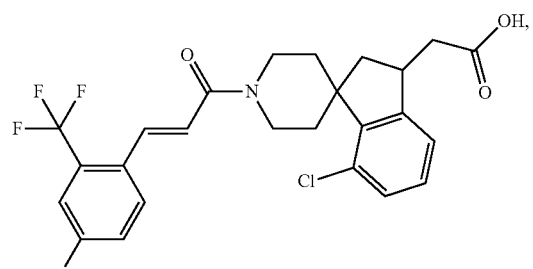

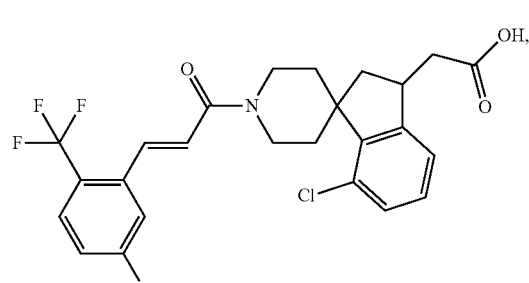

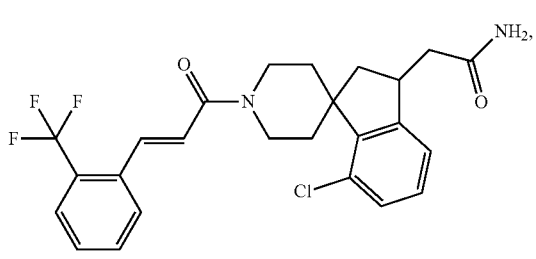

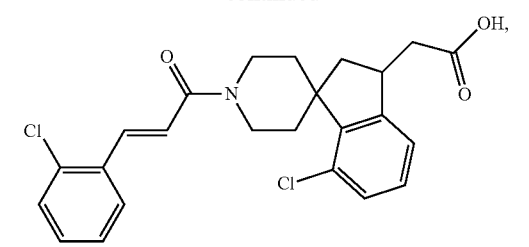
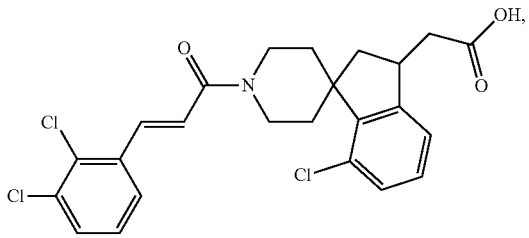
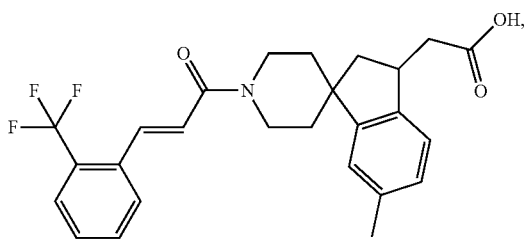
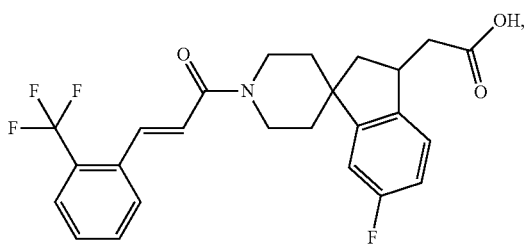
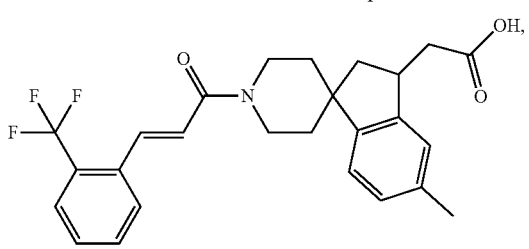
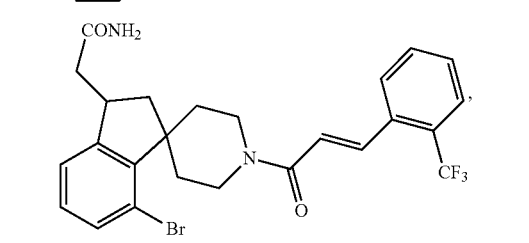
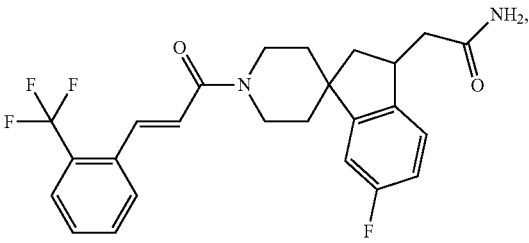
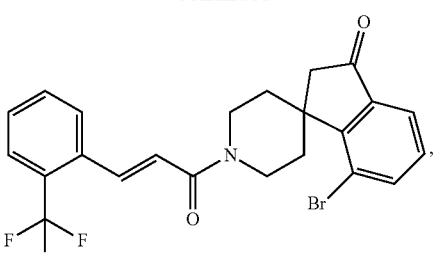
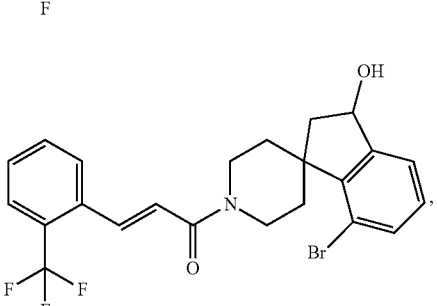
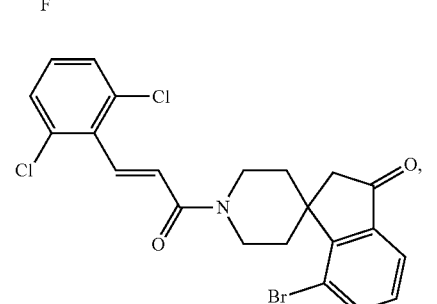
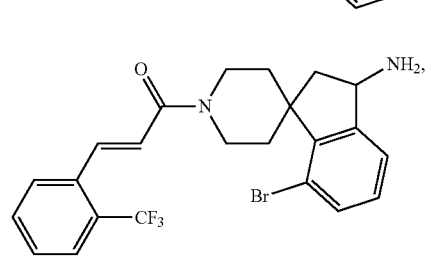
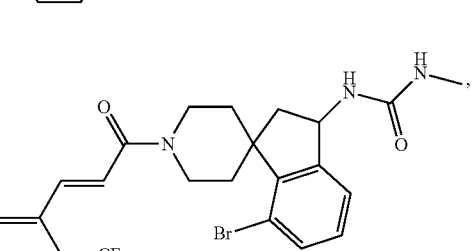
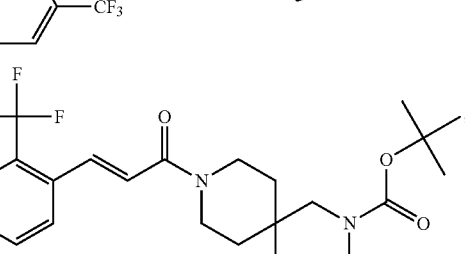

127
-continued
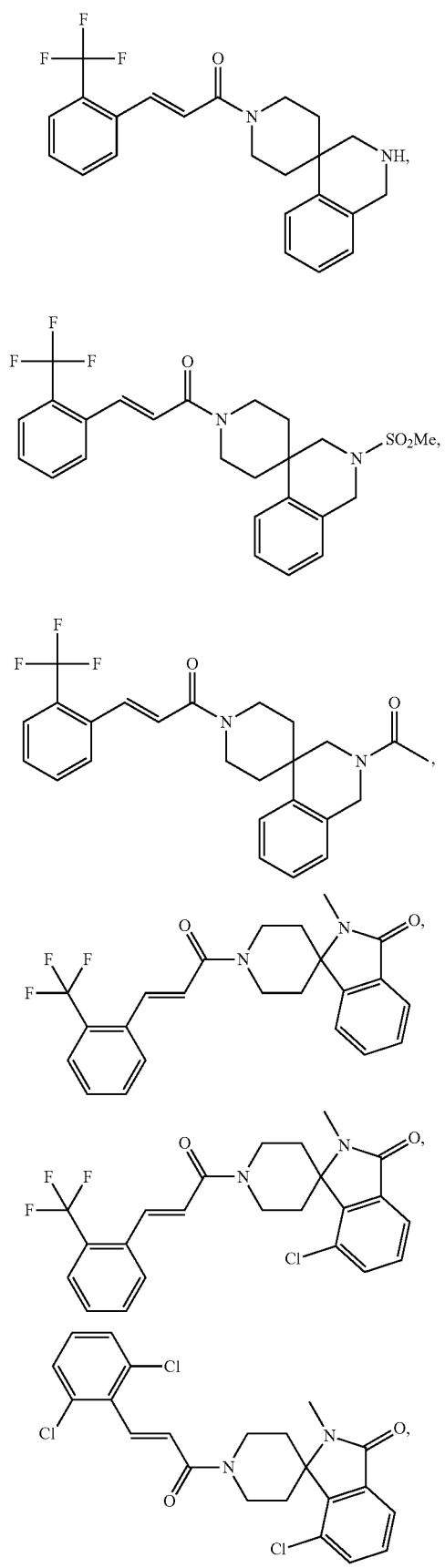
128
-continued
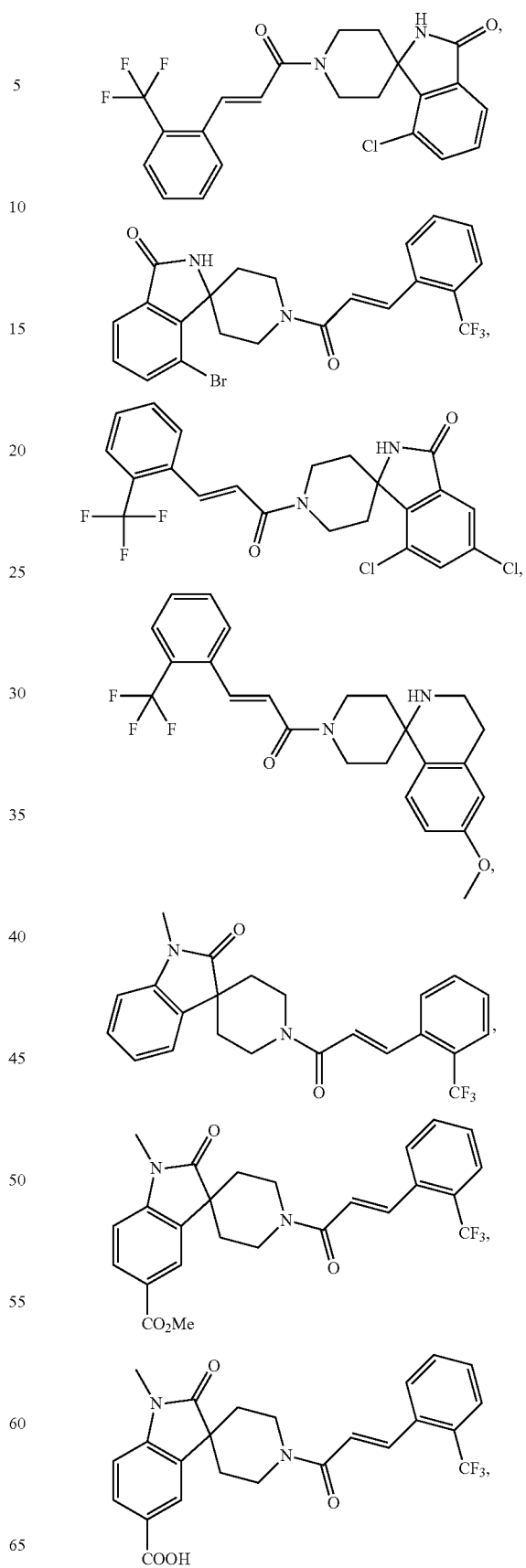

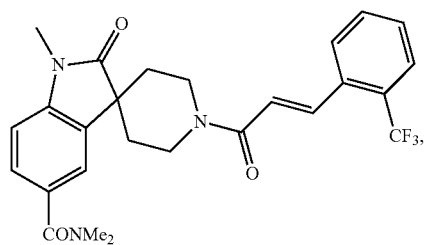
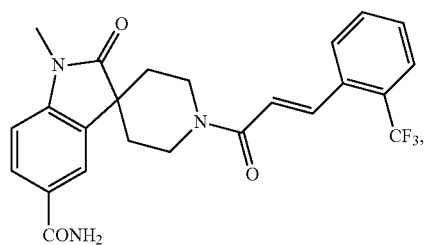
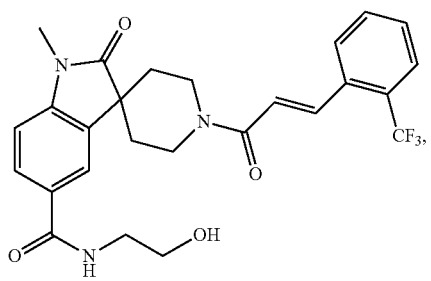
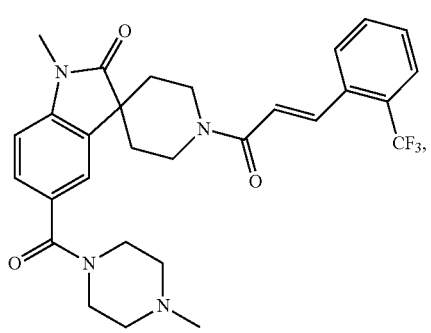
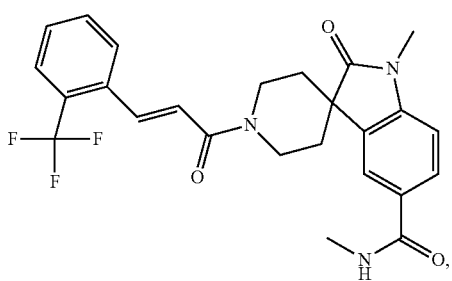
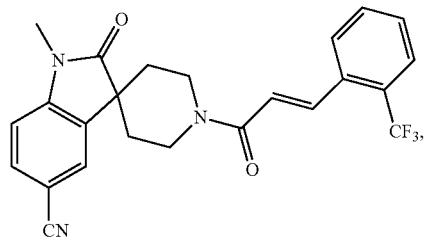
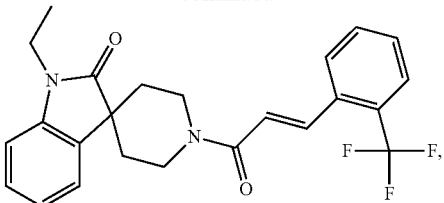
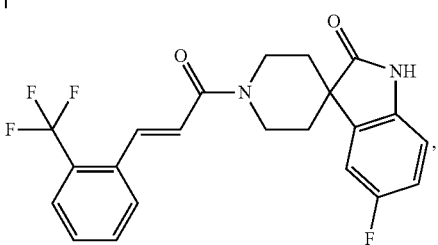
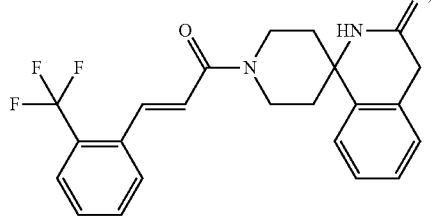
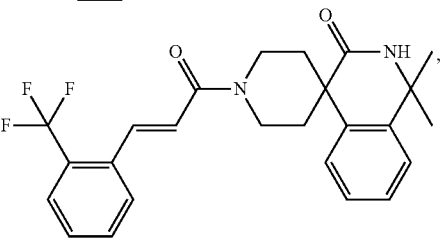
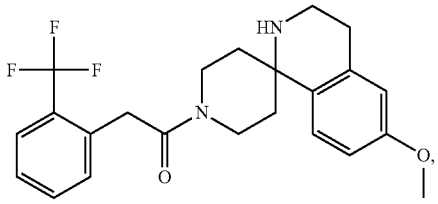
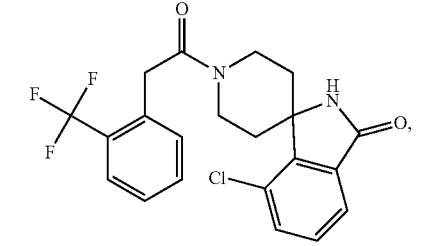
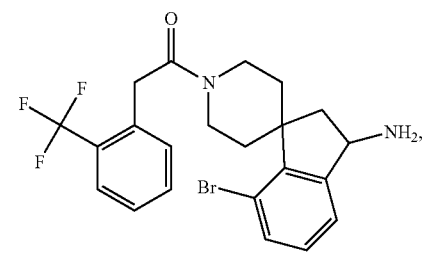

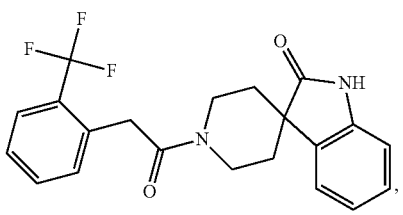
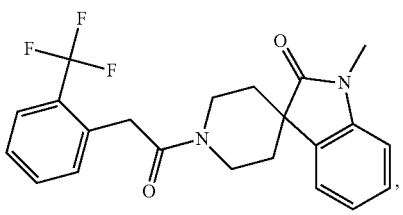
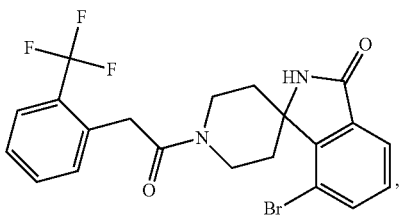
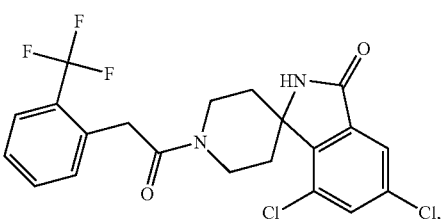
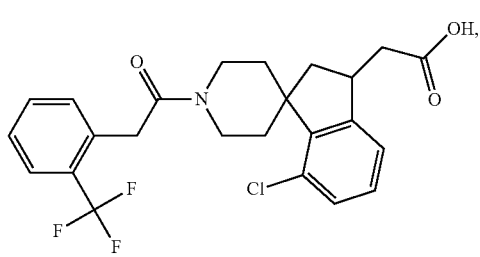
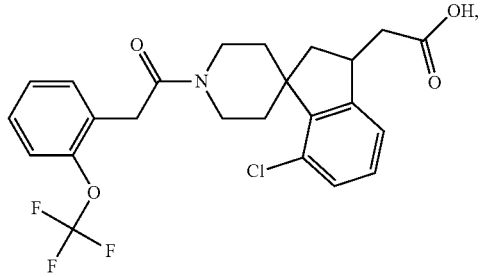
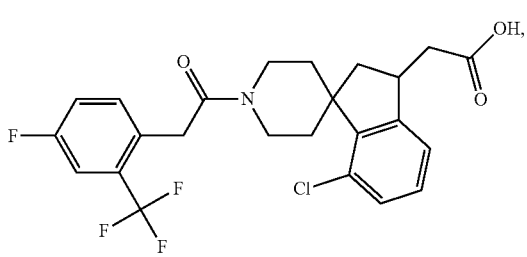
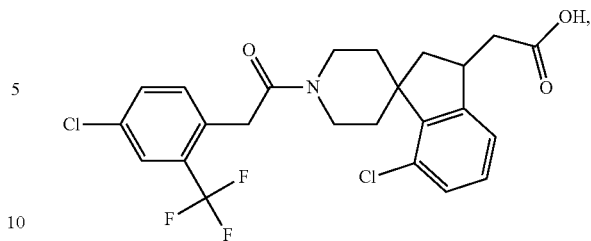
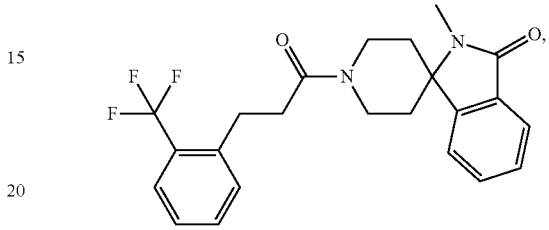
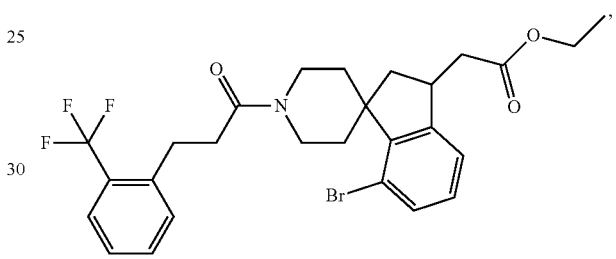
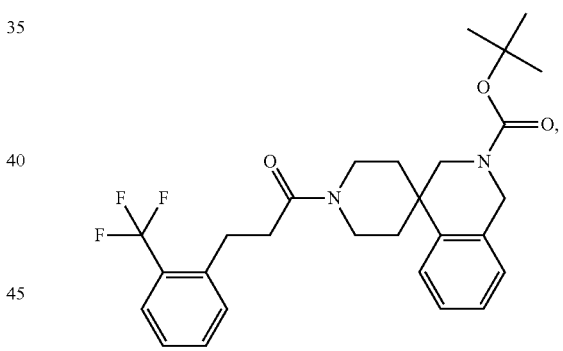
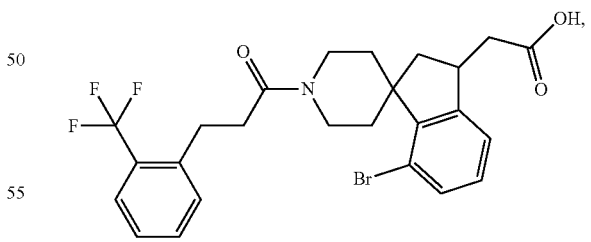
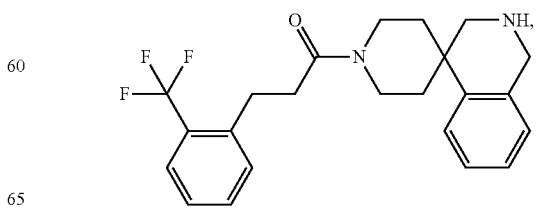

133
-continued
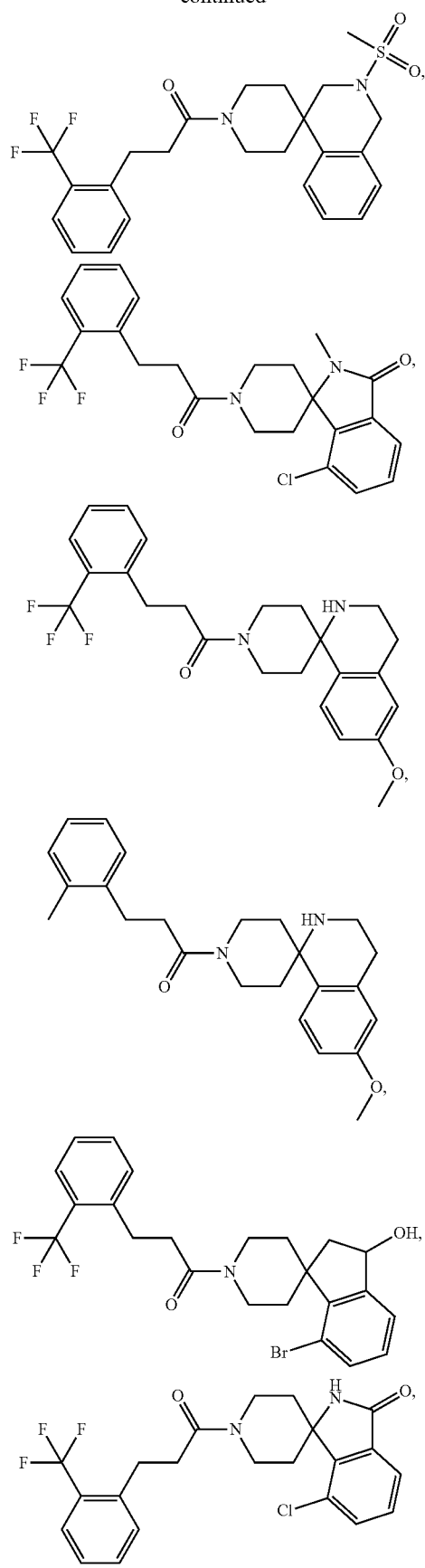
134
-continued
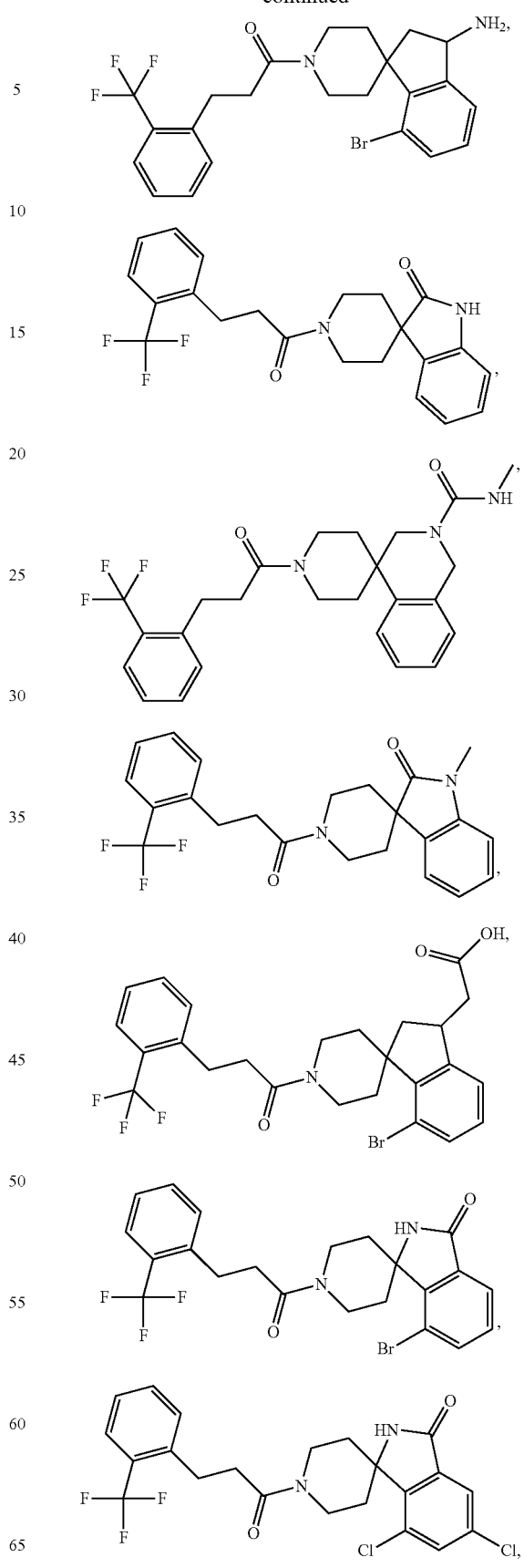

-continued
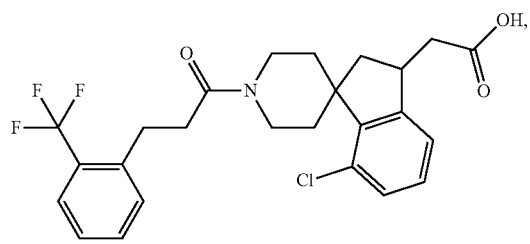
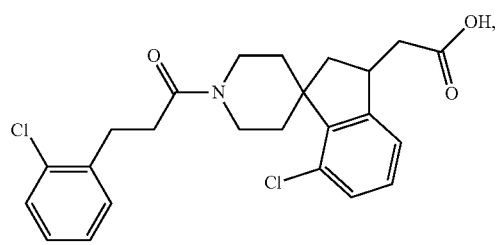
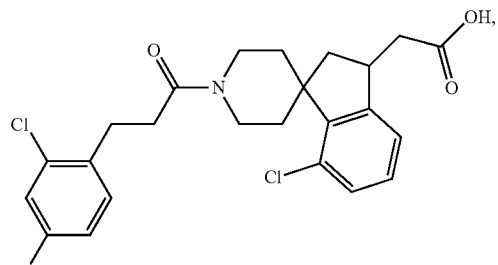
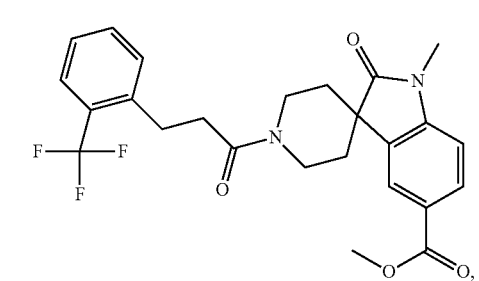
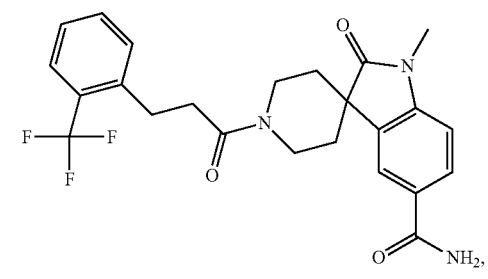
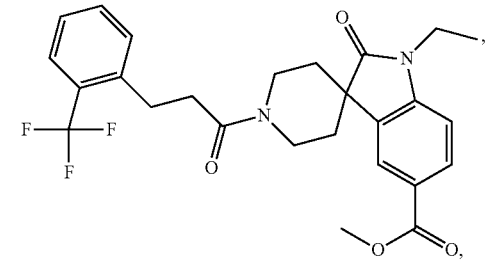
-continued
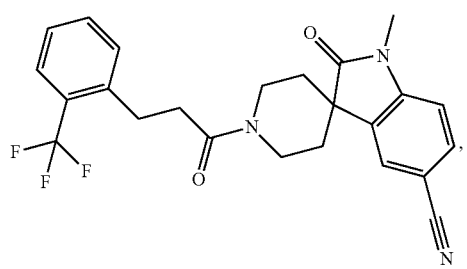
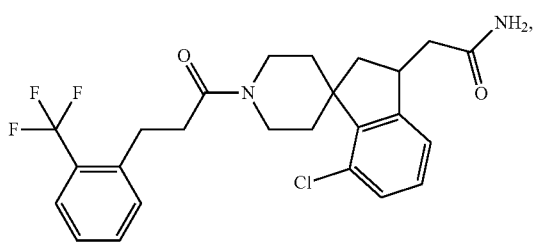
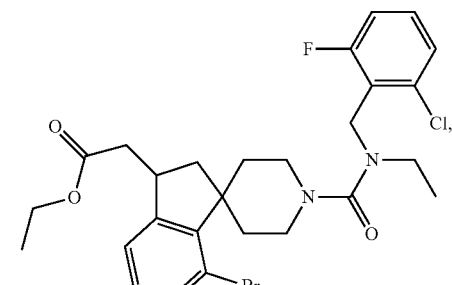
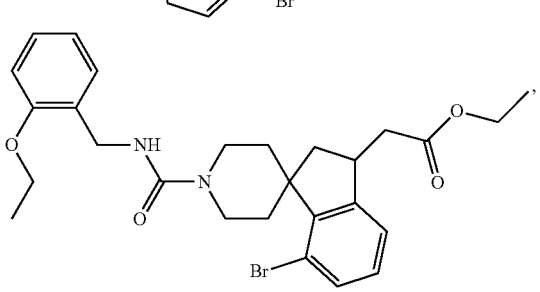
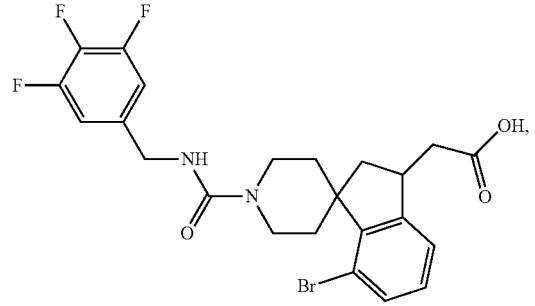
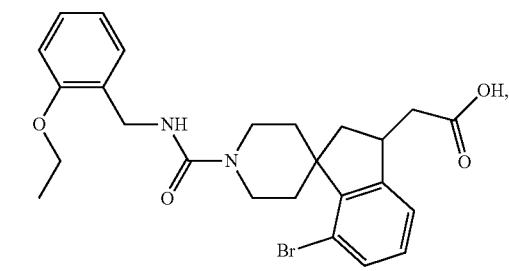

137
-continued
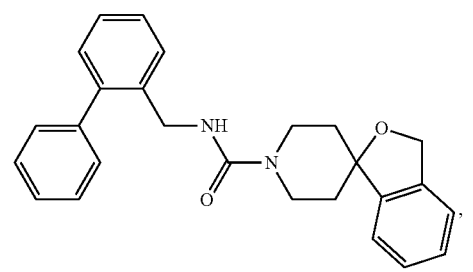
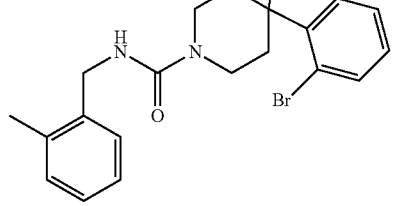
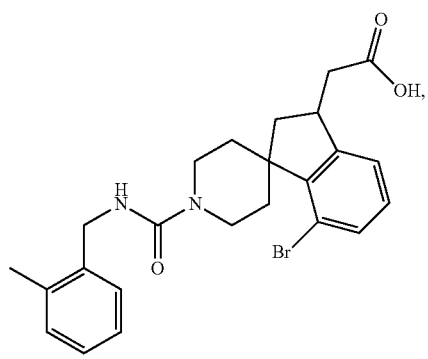
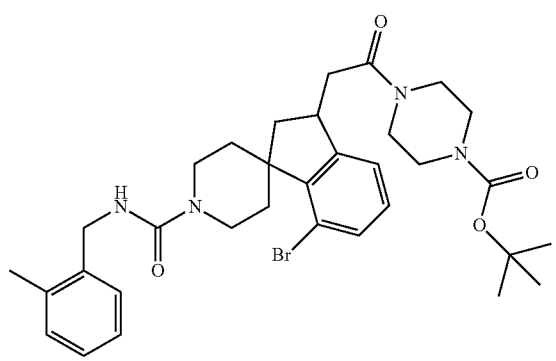
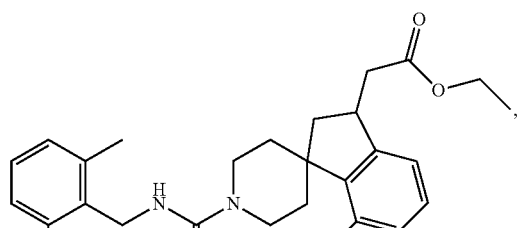
138
-continued
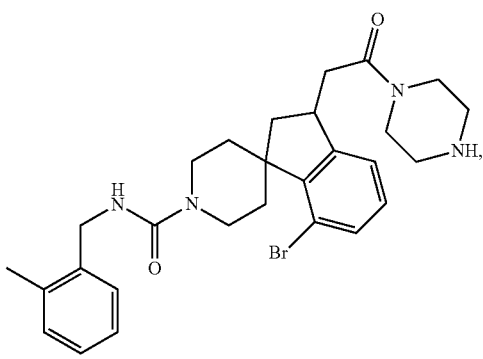
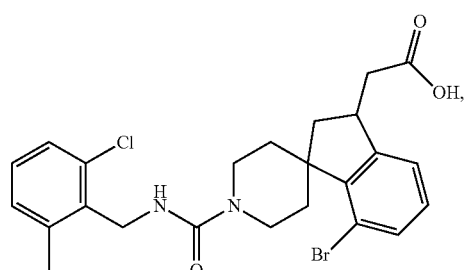
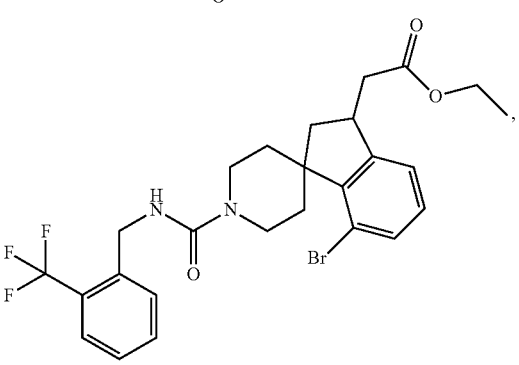
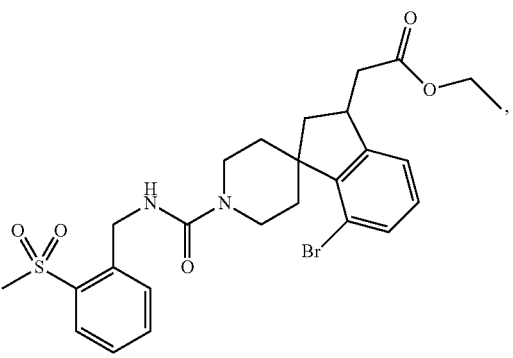
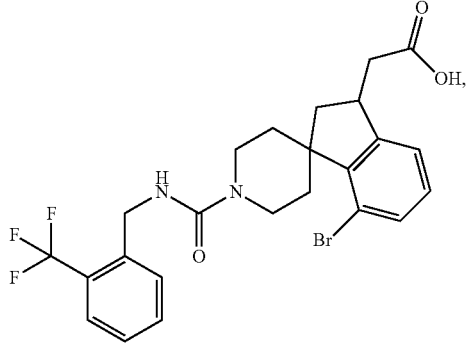

139
-continued
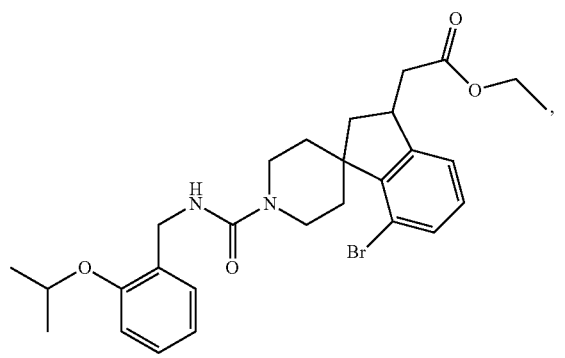
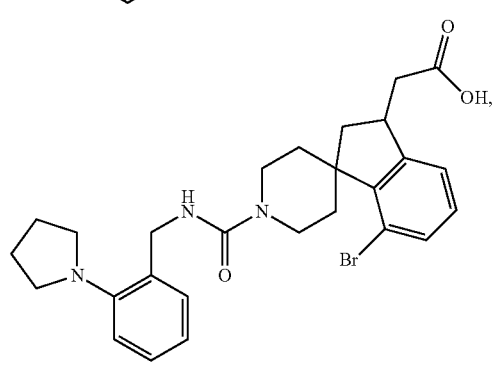
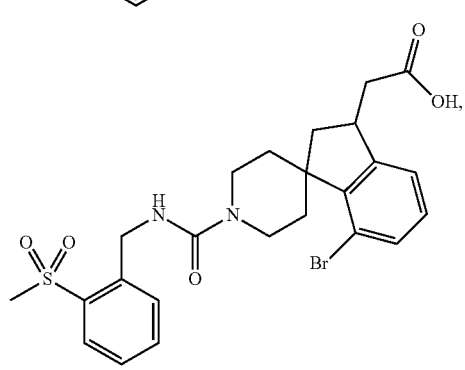
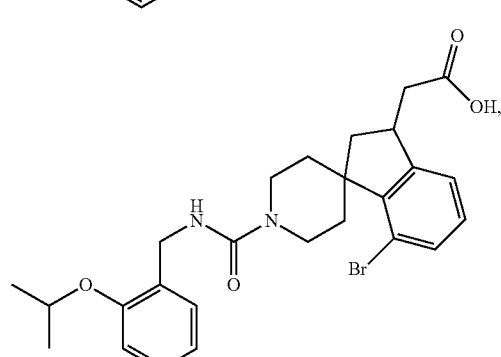
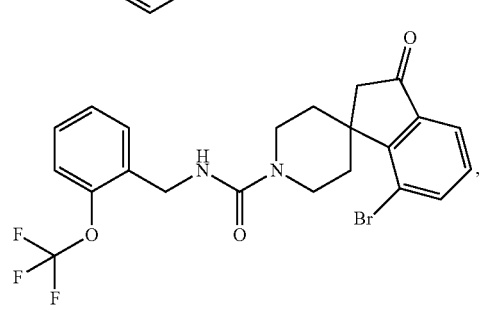
140
-continued
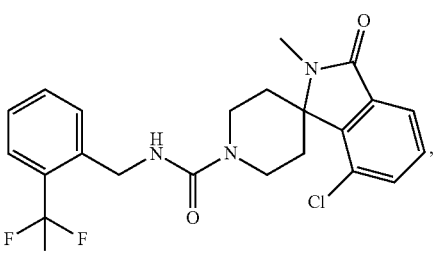
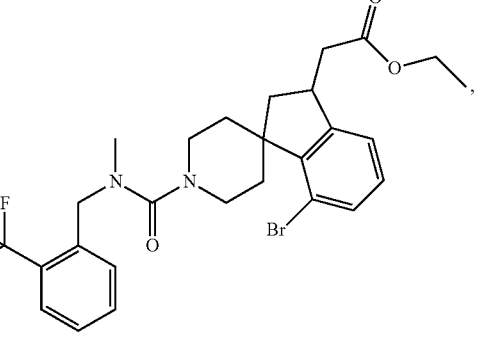
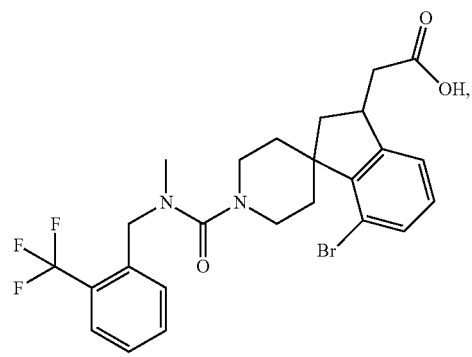
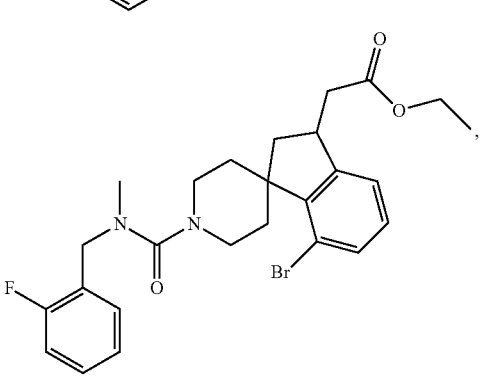
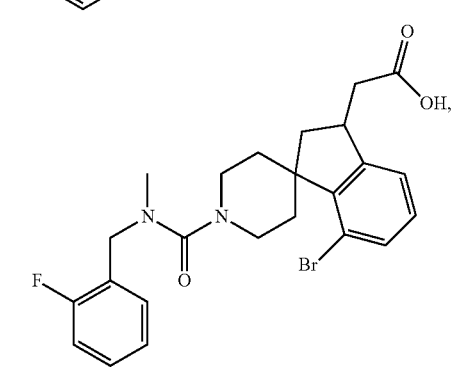

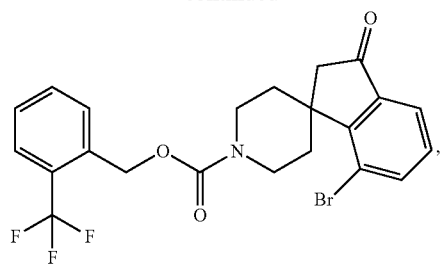

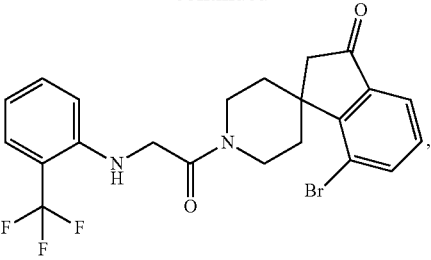

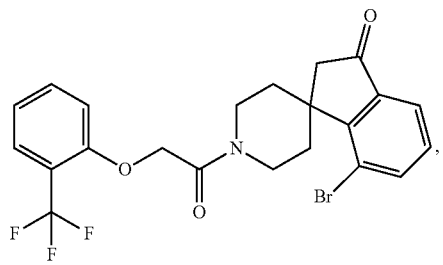

and or a pharmaceutically acceptable salt thereof.

26. A method of treating a subject with a disease selected from diabetes mellitus, metabolic syndrome, glucose intolerance, hyperglycemia, cognitive decline, hypertension, hyperlipidemia, insulin resistance, and hypertension caused by cardiovascular disease, comprising the step of administering to the subject an effective amount of the compound in claim 1.

27. The method of claim 26, wherein the disease is Type II diabetes mellitus.

\* \* \* \* \*